US007446241B2

(12) United States Patent
Rock et al.

(10) Patent No.: US 7,446,241 B2
(45) Date of Patent: Nov. 4, 2008

(54) TRANSCRIPTION FACTORS, DNA AND METHODS FOR INTRODUCTION OF VALUE-ADDED SEED TRAITS AND STRESS TOLERANCE

(75) Inventors: Christopher Dale Rock, Lubbock, TX (US); Srinivas Satyalinga Gampala, Menlo Park, CA (US)

(73) Assignee: Texas Tech University, Lubbock, TX (US)

( * ) Notice: Subject to any disclaimer, the term of this patent is extended or adjusted under 35 U.S.C. 154(b) by 318 days.

(21) Appl. No.: 10/996,058

(22) Filed: Nov. 24, 2004

(65) Prior Publication Data

US 2005/0193443 A1 Sep. 1, 2005

Related U.S. Application Data

(63) Continuation-in-part of application No. 10/629,907, filed on Jul. 30, 2003, now abandoned.

(60) Provisional application No. 60/399,565, filed on Jul. 30, 2002.

(51) Int. Cl.
*C12N 15/82* (2006.01)
*A01H 5/00* (2006.01)
(52) U.S. Cl. .................... 800/289; 800/298; 800/320.1; 435/419; 435/468; 435/320.1; 435/252.3
(58) Field of Classification Search ...................... None
See application file for complete search history.

(56) References Cited

U.S. PATENT DOCUMENTS

| | | | |
|---|---|---|---|
| 5,723,751 A | 3/1998 | Chua | |
| 5,731,419 A | 3/1998 | Sarhan et al. | |
| 5,837,545 A | 11/1998 | Guy et al. | |
| 5,891,859 A | 4/1999 | Thomashow et al. | |
| 5,981,729 A | 11/1999 | Chun et al. | |
| 5,981,842 A | 11/1999 | Wu et al. | |
| 6,160,202 A | 12/2000 | Bustos et al. | |
| 6,194,559 B1 | 2/2001 | Kim | |
| 6,218,527 B1 | 4/2001 | Kim | |
| 6,232,461 B1 | 5/2001 | Kim | |
| 6,245,905 B1 | 6/2001 | Kim | |
| 6,248,937 B1 | 6/2001 | Finkelstein et al. | |
| 6,762,348 B1 | 7/2004 | Harberd et al. | |
| 6,768,041 B2 | 7/2004 | Strabala et al. | |
| 6,781,035 B1 | 8/2004 | Harada et al. | |
| 6,784,340 B1 | 8/2004 | Aoyama et al. | |
| 6,784,343 B2 | 8/2004 | Zhu et al. | |
| 2002/0102695 A1 | 8/2002 | Silva et al. | |
| 2003/0172403 A1 | 9/2003 | Huang et al. | |
| 2004/0111768 A1 | 6/2004 | e Sliva et al. | |

OTHER PUBLICATIONS

Siberil Y. et al. Plant bZIP G-box binding factors. Modular structure and activation mechanisms. Eur J Biochem. Nov. 2001;268(22):5655-66. Review.*

Depres C. et al. The Arabidopsis NPR1/NIM1 protein enhances the DNA binding activity of a subgroup of the TGA family of bZIP transcription factors. Plant Cell. Feb. 2000;12(2):279-90.*

Tamminen I. et al. Ectopic expression of ABI3 gene enhances freezing tolerance in response to abscisic acid and low temperature in Arabidopsis thaliana. Plant J. Jan. 2001;25(1):1-8.*

Whisstock J.C. et al. Prediction of protein function from protein sequence and structure. Q Rev Biophys. Aug. 2003;36(3):307-40. Review.*

Curtis M.D. et al. (A gateway cloning vector set for high-throughput functional analysis of genes in planta. Plant Physiol. Oct. 2003;133(2):462-9.*

Finkelstein et al. Redundant and distinct functions of the ABA response loci ABA-Insensitive(ABI)5 and ABRE-Binding Factor (ABF)3. Plant Mol Biol. Sep. 2005;59(2):253-67.*

Tokunori Hobo, Yasuo Kowyama, and Tsukaho Hattori, "A bZIP factor, TRAB1, interacts with VP1 and mediates abscisic acid-induced transcription," 15348-15353 PNAS, vol. 96 (No. 26), (Dec. 21, 1999).

Joung-Youn Kang, Hyung-In Choi, Min-Young Im, and Soo Young Kim, "Arabidopsis Basic Leucine Zipper Proteins That Mediate Stress-Responsive Abscisic Acid Signaling," The Plant Cell, American Society of Plant Biologists, p. 343-357, (Feb. 2002).

Masaharu Suzuki, Chien-Yuan Kao, Suzy Cocciolone and Donald R. McCarty, "Maize VP1 complements Arabidopsis abi3 and confers a novel ABA/auxin interaction in roots," The Plant Journal, Blackwell Science Ltd, vol. 28 (No. 4), p. 409-418, (2001).

Hartmut Luerben, Viktor Kirik, Petra Hermann and Simon Misera, "FUSCA3 encodes a protein with a conserved VP1/ABI3-like B3 domain which is of functional importance for the regulation of seed maturation in Arabidopsis thaliana," The Plant Journal, Blackwell Science Ltd, vol. 15 (No. 6), p. 755-764, (1998).

Hu Yx, Wang Yx, Liu Xf, Li Jy, "Arabidopsis RAV1 is down-regulated by brassinosteroid and may act as a negative regulator during plant development," Web Article, PMID: 15040885 [PubMed—indexed for Medline].

Mendel Biotechnology Inc., "Annual Report 2002."

(Continued)

*Primary Examiner*—Cynthia Collins
(74) *Attorney, Agent, or Firm*—Jones, Tullar & Cooper, P.C.

(57) ABSTRACT

Abscisic acid-inducible gene expression in different plant tissues is enhanced synergistically by the co-expression of a B3-domain transcription factor and various bZIP-domain transcription factors, or a different B3-domain transcription factor. Using these transcription factors in novel formulations, as shown by examples, will confer value-added traits to transgenic plants, including, but not limited to, higher levels of heterologous gene expression, drought and salt tolerance, viability and productivity under stress, and enhanced nutrient reserves and seed properties.

66 Claims, 3 Drawing Sheets

OTHER PUBLICATIONS

Figure 1:
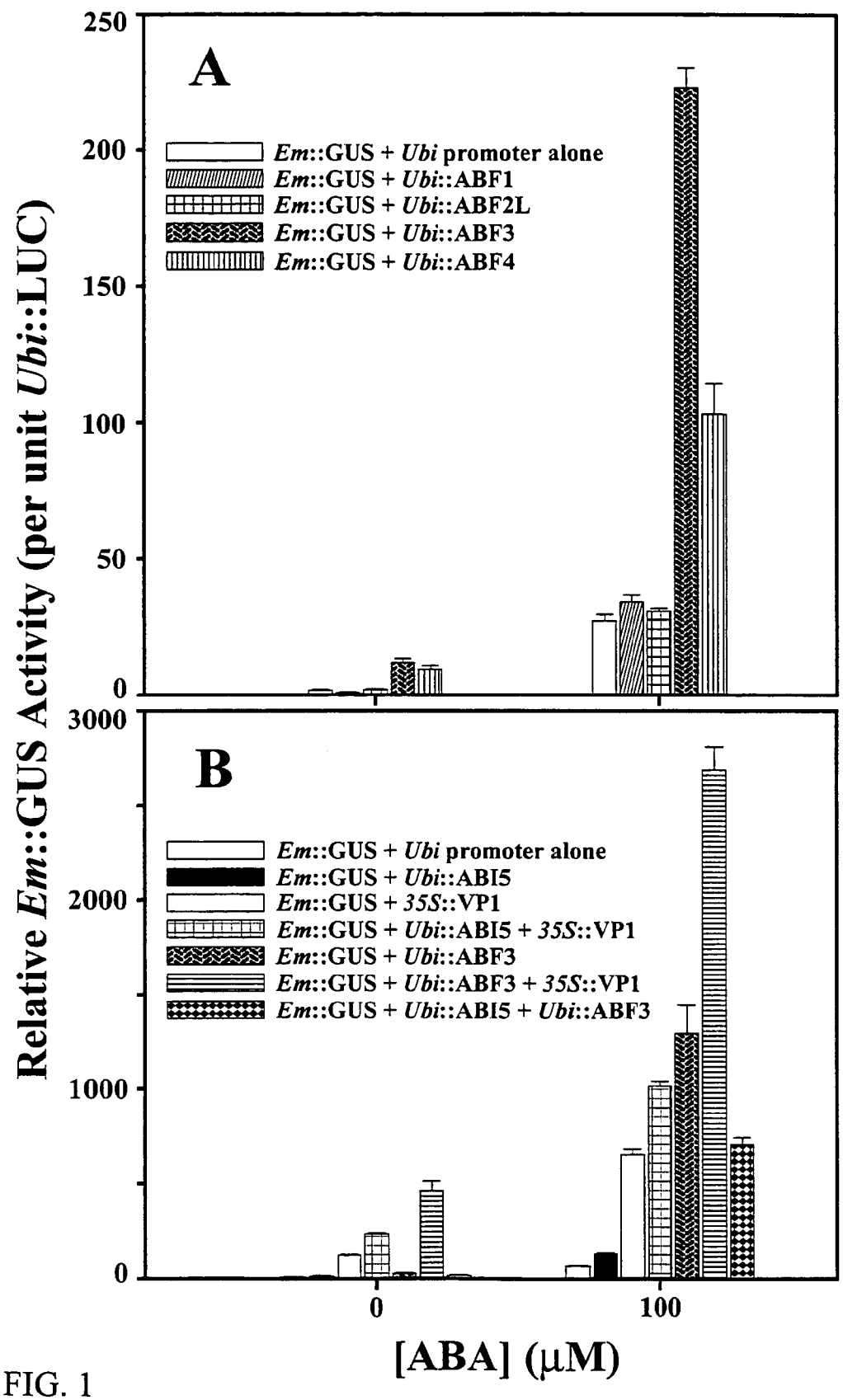

Yasuaki Kagaya, Junio Ohmiya and Tsukaho Hattori, "RAV1, a novel DNA-binding protein, binds to bipartite recognition sequence through two distinct DNA-binding domains uniquely found in higher plants," Nucleic Acids Research, Oxford Univeristy Press, vol. 27 (No. 2), p. 470-478, (1999).

Sunmi Kim, Jun-Youn Kang, Dong-Im Cho, Ji Hye Park and Soo Young Kim, "ABF2, an ABRE-binding bZIP factor, is an essential component of glucose signaling and its overexpression affects multiple stress tolerance," The Plant Journal, Blackwell Publishing Ltd, p. 75-87, (2004).

Yuichi Uno, Takashi Furihata, Hiroshi Abe, Riichiro Yoshida, Kazuo Shinozaki, and Kazuko Yamaguchi-Shinozaki, "Arabidopsis basic leucine zipper transcription factors involved in an abscisic acid-dependent signal transduction pathway under drought and high-salinity conditions," 11632-11637 PNAS, vol. 97 (No. 21), (Oct. 10, 2000).

Sandra Bensmihen, Sonia Rippa, Guillaume Lambert, Delphine Jublot, Veronique Pautot, Fabienne Granier, Jerome Giraudat, and Francois Parcy, "The Homologous ABI5 and EEL Transcirption Factors Function Antagonistically to Fine-Tune Gene Expression during Late Embryogenesis," The Plant Cell, p. 1391-1403, (Jun. 2002).

Sandra L. Stone, Linda W. Kwong, Kelly Matsudaira Yee, Julie Pelletier, Loic Lepiniec, Robert L. Fischer, Robert B. Goldberg, and John J. Harada, "Leafy Cotyledon2 encodes a B3 domain transcription factor that induces embryo development," 11806-11811 PNAS, vol. 98 (No. 20), (Sep. 25, 2001).

\* cited by examiner

SEQUENCE LISTING

<160> NUMBER OF SEQ ID NOS: 78

<210> SEQ ID NO 1
<211> LENGTH: 2076
<212> TYPE: DNA
<213> ORGANISM: Zea mays

<400> SEQUENCE: 1

| | | | | | |
|---|---|---|---|---|---|
| atggaagcct | cctccggctc | gtcgccaccg | cactcccaag | agaacccgcc | ggagcacggt | 60 |
| ggcgacatgg | gaggggcccc | cgcggaggag | atcggagggg | aggcggcgga | tgacttcatg | 120 |
| ttcgctgaag | acacgttccc | ctccctcccg | gacttccctt | gcctttcgtc | gccgtccagc | 180 |
| tccaccttct | cgtccaactc | ctcgtcaaac | tcctccagcg | cctacaccaa | cacggcagga | 240 |
| agagccggcg | gcgagccctc | cgagcctgct | tcggccggag | aagggtttga | tgcgctcgat | 300 |
| gacatcgacc | agctcctcga | cttcgcgtcg | ctttccatgc | cgtgggactc | cgagccgttc | 360 |
| ccggggggtta | gcatgatgct | agagaacgcc | atgtcggcgc | cgccgcagcc | ggtgggcgac | 420 |
| ggcatgagtg | aagagaaagc | cgtgccggaa | gggaccacgg | ggggagagga | ggcctgcatg | 480 |
| gatgcgtcgg | aggggagga | gctgccgcgg | ttcttcatgg | agtggctcac | gagcaaccgc | 540 |
| gaaaacatct | cggccgagga | tctccgcggg | atccgcctcc | gccgtccac | catcgaggcc | 600 |
| gccgccgccc | ggctcggcgg | cgggcgccag | ggcaccatgc | agctgctcaa | gctcatcctc | 660 |
| acctgggtgc | agaaccacca | cctccagagg | aagcgcccgc | gcgacgtgat | ggaggaggag | 720 |
| gcgggcctgc | acgtccagct | ccccagcccg | gtcgccaacc | caccaggata | cgagttcccc | 780 |
| gccgcggac | aggacatggc | cgcgggcggc | ggcacatctt | ggatgcccca | ccagcaggca | 840 |
| ttcacgccgc | ctgctgcgta | cggcggcgac | gcggtgtacc | cgagcgcggc | aggccaacag | 900 |
| tactctttcc | accagggccc | cagcacgagc | agcgtggtcg | tgaacagcca | accgttctcc | 960 |
| ccgccgcctg | tgggcgacat | gcacggcgcg | aacatggcct | ggccgcagca | gtacgtgccg | 1020 |
| ttcccaccgc | ctgggcttc | cacgggctct | taccctatgc | cgcagccgtt | ctccccggga | 1080 |
| ttcggcgggc | agtacgccgg | cgccggcgct | ggccacctct | cagtggcccc | ccagcgcatg | 1140 |
| gcaggcgtgg | aggcctcggc | gaccaaggag | gcccgcaaga | agcgcatggc | gagacagcgg | 1200 |
| cgcctgtcct | gcctgcagca | gcagcgcagc | cagcagctga | gcctgggcca | gatccagacc | 1260 |
| tccgtccacc | tgcaggagcc | gtcccctcgg | tccacgcact | ccggcccggt | cacgccgtca | 1320 |
| gcaggcggct | ggggattctg | gtcgccgagc | agccagcagc | aggtccagaa | cccgctctcc | 1380 |
| aagtccaatt | cctcaagggc | gccgccttcc | tcgctggaag | cggcggcggc | ggctccacag | 1440 |
| acaaagcccg | cgcctgctgg | tgctcggcag | gacgacattc | accaccgcct | cgcagcggct | 1500 |
| tcagataagc | ggcagggcgc | caaggcggac | aagaacctgc | ggttcctgct | gcagaaggtg | 1560 |
| ctgaagcaga | gcgacgtcgg | gagcctcggc | cgcatcgtg | tccccaaaaa | ggaagcggag | 1620 |
| gttcacctgc | cggagctgaa | gacgagggat | ggcatctcca | tccccatgga | ggacatcgga | 1680 |
| acgtcgcgcg | tgtggaacat | gcggtacagg | ttttggccca | acaacaagag | cagaatgtat | 1740 |
| ctgctggaaa | acacagggga | atttgttcgt | tccaacgagc | ttcaggaggg | ggatttcata | 1800 |
| gtgatctact | ccgatgtcaa | gtcgggcaaa | tatctgatac | ggggcgtgaa | ggtaaggccc | 1860 |
| ccgccggcgc | aagagcaagg | cagtggttcc | agcgggggag | gcaagcacag | gcccctctgt | 1920 |
| ccagcaggtc | cagagagagc | cgcagccgcc | ggtgctcctg | aagacgccgt | cgtcgacggg | 1980 |
| gtcagcggcg | cctgcaaggg | gaggtctccg | gaaggcgtgc | ggcgggttcg | gcagcaggga | 2040 | gccggcgcca tgagccagat ggcggtgagc atctga                                    2076

<210> SEQ ID NO 2
<211> LENGTH: 691
<212> TYPE: PRT
<213> ORGANISM: Zea mays

<400> SEQUENCE: 2

```
Met Glu Ala Ser Ser Gly Ser Ser Pro Pro His Ser Gln Glu Asn Pro
 1               5                  10                  15

Pro Glu His Gly Gly Asp Met Gly Gly Ala Pro Ala Glu Glu Ile Gly
            20                  25                  30

Gly Glu Ala Ala Asp Asp Phe Met Phe Ala Glu Asp Thr Phe Pro Ser
        35                  40                  45

Leu Pro Asp Phe Pro Cys Leu Ser Ser Pro Ser Ser Thr Phe Ser
    50                  55                  60

Ser Asn Ser Ser Ser Asn Ser Ser Ala Tyr Thr Asn Thr Ala Gly
 65                  70                  75                  80

Arg Ala Gly Gly Glu Pro Ser Glu Pro Ala Ser Ala Gly Glu Gly Phe
                85                  90                  95

Asp Ala Leu Asp Asp Ile Asp Gln Leu Leu Asp Phe Ala Ser Leu Ser
            100                 105                 110

Met Pro Trp Asp Ser Glu Pro Phe Pro Gly Val Ser Met Met Leu Glu
        115                 120                 125

Asn Ala Met Ser Ala Pro Pro Gln Pro Val Gly Asp Gly Met Ser Glu
    130                 135                 140

Glu Lys Ala Val Pro Glu Gly Thr Thr Gly Gly Glu Glu Ala Cys Met
145                 150                 155                 160

Asp Ala Ser Glu Gly Glu Glu Leu Pro Arg Phe Phe Met Glu Trp Leu
                165                 170                 175

Thr Ser Asn Arg Glu Asn Ile Ser Glu Asp Leu Arg Gly Ile Arg
            180                 185                 190

Leu Arg Arg Ser Thr Ile Glu Ala Ala Ala Arg Leu Gly Gly Gly
        195                 200                 205

Arg Gln Gly Thr Met Gln Leu Leu Lys Leu Ile Leu Thr Trp Val Gln
    210                 215                 220

Asn His His Leu Gln Arg Lys Arg Pro Arg Asp Val Met Glu Glu Glu
225                 230                 235                 240

Ala Gly Leu His Val Gln Leu Pro Ser Pro Val Ala Asn Pro Pro Gly
                245                 250                 255

Tyr Glu Phe Pro Ala Gly Gly Gln Asp Met Ala Ala Gly Gly Gly Thr
            260                 265                 270

Ser Trp Met Pro His Gln Gln Ala Phe Thr Pro Pro Ala Ala Tyr Gly
        275                 280                 285

Gly Asp Ala Val Tyr Pro Ser Ala Ala Gly Gln Gln Tyr Ser Phe His
    290                 295                 300

Gln Gly Pro Ser Thr Ser Ser Val Val Val Asn Ser Gln Pro Phe Ser
305                 310                 315                 320

Pro Pro Pro Val Gly Asp Met His Gly Ala Asn Met Ala Trp Pro Gln
                325                 330                 335

Gln Tyr Val Pro Phe Pro Pro Gly Ala Ser Thr Gly Ser Tyr Pro
            340                 345                 350

Met Pro Gln Pro Phe Ser Pro Gly Phe Gly Gly Gln Tyr Ala Gly Ala
        355                 360                 365
```

```
Gly Ala Gly His Leu Ser Val Ala Pro Gln Arg Met Ala Gly Val Glu
        370                 375                 380

Ala Ser Ala Thr Lys Glu Ala Arg Lys Lys Arg Met Ala Arg Gln Arg
385                 390                 395                 400

Arg Leu Ser Cys Leu Gln Gln Arg Ser Gln Gln Leu Ser Leu Gly
                405                 410                 415

Gln Ile Gln Thr Ser Val His Leu Gln Glu Pro Ser Pro Arg Ser Thr
                420                 425                 430

His Ser Gly Pro Val Thr Pro Ser Ala Gly Gly Trp Gly Phe Trp Ser
                435                 440                 445

Pro Ser Gln Gln Gln Val Gln Asn Pro Leu Ser Lys Ser Asn Ser
450                 455                 460

Ser Arg Ala Pro Pro Ser Ser Leu Glu Ala Ala Ala Ala Pro Gln
465                 470                 475                 480

Thr Lys Pro Ala Pro Ala Gly Ala Arg Gln Asp Asp Ile His His Arg
                485                 490                 495

Leu Ala Ala Ala Ser Asp Lys Arg Gln Gly Ala Lys Ala Asp Lys Asn
                500                 505                 510

Leu Arg Phe Leu Leu Gln Lys Val Leu Lys Gln Ser Asp Val Gly Ser
        515                 520                 525

Leu Gly Arg Ile Val Leu Pro Lys Lys Glu Ala Glu Val His Leu Pro
        530                 535                 540

Glu Leu Lys Thr Arg Asp Gly Ile Ser Ile Pro Met Glu Asp Ile Gly
545                 550                 555                 560

Thr Ser Arg Val Trp Asn Met Arg Tyr Arg Phe Trp Pro Asn Asn Lys
                565                 570                 575

Ser Arg Met Tyr Leu Leu Glu Asn Thr Gly Glu Phe Val Arg Ser Asn
                580                 585                 590

Glu Leu Gln Glu Gly Asp Phe Ile Val Ile Tyr Ser Asp Val Lys Ser
        595                 600                 605

Gly Lys Tyr Leu Ile Arg Gly Val Lys Val Arg Pro Pro Ala Gln
        610                 615                 620

Glu Gln Gly Ser Gly Ser Ser Gly Gly Lys His Arg Pro Leu Cys
625                 630                 635                 640

Pro Ala Gly Pro Glu Arg Ala Ala Ala Gly Ala Pro Glu Asp Ala
                645                 650                 655

Val Val Asp Gly Val Ser Gly Ala Cys Lys Gly Arg Ser Pro Glu Gly
                660                 665                 670

Val Arg Arg Val Arg Gln Gln Gly Ala Gly Ala Met Ser Gln Met Ala
        675                 680                 685

Val Ser Ile
    690

<210> SEQ ID NO 3
<211> LENGTH: 1059
<212> TYPE: DNA
<213> ORGANISM: Arabidopsis thaliana

<400> SEQUENCE: 3
atggattcta gttgcataga cgagataagt tcctccactt cagaatcttt ctccgccacc      60
accgccaaga agctctctcc tcctcccgcg gcggcgttac gcctctaccg gatgggaagc     120
ggcgggagca gcgtcgtgtt ggatcccgag aacggcctag agacggagtc acgaaagcta     180
ccatcttcaa aatacaaagg tgttgttcct cagcctaacg gaagatgggg agctcagatc     240
```

-continued

```
tacgagaagc accaacgagt atggctcggg actttcaacg agcaagaaga agctgctcgt      300
tcctacgaca tcgcagcttg tagattccgt ggccgcgacg ccgtcgtcaa cttcaagaac      360
gttctggaag acggcgattt agcttttctt gaagctcact caaaggccga gatcgtcgac      420
atgttgagaa acacactta cgccgacgag cttgaacaga caataaacg gcagttgttt       480 ctctccgtcg acgctaacgg aaaacgtaac ggatcgagta ctactcaaaa cgacaaagtt      540
ttaaagacgc gtgaagttct tttcgagaag gctgttacac ctagcgacgt gggaagcta       600 aaccgtctcg tgatacctaa acaacacgcc gagaaacact tccgttaccg tcaccgtca       660 ccggcagtga ctaaaggagt tttgatcaac ttcgaagacg ttaacggtaa agtgtggagg      720
ttccgttact catactggaa cagtagtcaa agttacgtgt tgaccaaggg atggagtcga      780
ttcgtcaagg agaagaatct tcgagccggt gatgttgtta ctttcgagag atcgaccgga      840
ctagagcggc agttatatat tgattggaaa gttcggtctg gtccgagaga aaacccggtt      900
caggtggtgg ttcggctttt cggagttgat atctttaatg tgaccaccgt gaagccaaac      960
gacgtcgtgg ccgtttgcgg tggaaagaga tctcgagatg ttgatgatat gtttgcgtta     1020
cggtgttcca agaagcaggc gataatcaat gctttgtga                           1059
```

<210> SEQ ID NO 4
<211> LENGTH: 352
<212> TYPE: PRT
<213> ORGANISM: Arabidopsis thaliana

<400> SEQUENCE: 4

```
Met Asp Ser Ser Cys Ile Asp Glu Ile Ser Ser Thr Ser Glu Ser
1               5                   10                  15

Phe Ser Ala Thr Thr Ala Lys Lys Leu Ser Pro Pro Ala Ala
            20                  25                  30

Leu Arg Leu Tyr Arg Met Gly Ser Gly Gly Ser Val Val Leu Asp
            35                  40                  45

Pro Glu Asn Gly Leu Glu Thr Glu Ser Arg Lys Leu Pro Ser Ser Lys
        50                  55                  60

Tyr Lys Gly Val Val Pro Gln Pro Asn Gly Arg Trp Gly Ala Gln Ile
65                  70                  75                  80

Tyr Glu Lys His Gln Arg Val Trp Leu Gly Thr Phe Asn Glu Gln Glu
                85                  90                  95

Glu Ala Ala Arg Ser Tyr Asp Ile Ala Ala Cys Arg Phe Arg Gly Arg
            100                 105                 110

Asp Ala Val Val Asn Phe Lys Asn Val Leu Glu Asp Gly Asp Leu Ala
        115                 120                 125

Phe Leu Glu Ala His Ser Lys Ala Glu Ile Val Asp Met Leu Arg Lys
130                 135                 140

His Thr Tyr Ala Asp Glu Leu Glu Gln Asn Asn Lys Arg Gln Leu Phe
145                 150                 155                 160

Leu Ser Val Asp Ala Asn Gly Lys Arg Asn Gly Ser Ser Thr Thr Gln
                165                 170                 175

Asn Asp Lys Val Leu Lys Thr Arg Glu Val Leu Phe Glu Lys Ala Val
            180                 185                 190

Thr Pro Ser Asp Val Gly Lys Leu Asn Arg Leu Val Ile Pro Lys Gln
        195                 200                 205

His Ala Glu Lys His Phe Pro Leu Pro Ser Pro Ser Pro Ala Val Thr
    210                 215                 220
```

```
Lys Gly Val Leu Ile Asn Phe Glu Asp Val Asn Gly Lys Val Trp Arg
225                 230                 235                 240

Phe Arg Tyr Ser Tyr Trp Asn Ser Ser Gln Ser Tyr Val Leu Thr Lys
            245                 250                 255

Gly Trp Ser Arg Phe Val Lys Glu Lys Asn Leu Arg Ala Gly Asp Val
        260                 265                 270

Val Thr Phe Glu Arg Ser Thr Gly Leu Glu Arg Gln Leu Tyr Ile Asp
    275                 280                 285

Trp Lys Val Arg Ser Gly Pro Arg Glu Asn Pro Val Gln Val Val Val
290                 295                 300

Arg Leu Phe Gly Val Asp Ile Phe Asn Val Thr Thr Val Lys Pro Asn
305                 310                 315                 320

Asp Val Val Ala Val Cys Gly Gly Lys Arg Ser Arg Asp Val Asp Asp
                325                 330                 335

Met Phe Ala Leu Arg Cys Ser Lys Lys Gln Ala Ile Ile Asn Ala Leu
                340                 345                 350

<210> SEQ ID NO 5
<211> LENGTH: 1329
<212> TYPE: DNA
<213> ORGANISM: Arabidopsis thaliana

<400> SEQUENCE: 5
atggtaacta gagaaacgaa gttgacgtca gagcgagaag tagagtcgtc catggcgcaa      60
gcgagacata atggaggagg tggtggtgag aatcatccgt ttacttcttt gggaagacaa     120
tcctctatct actcattgac ccttgacgag ttccaacatg ctttatgtga aacggcaag     180 aactttgggt ccatgaacat ggacgagttt cttgtctcta tttggaacgc agaggagaat     240
aataacaatc aacaacaagc agcagcagct gcaggttcac attctgttcc ggctaatcac     300
aatggtttca caacaacaa taacaatgga ggcgagggtg gtgttggtgt ctttagtggt     360
ggttctagag gcaacgaaga tgctaacaat aagagaggga tagcgaacga gtctagtctt     420
cctcgacaag gctctttgac acttccagct ccgctttgta ggaagactgt tgatgaggtt     480
tggtctgaga tacatagagg tggtggtagc ggtaatggag gagacagcaa tggacgtagt     540
agtagtagta atggacagaa caatgctcag aacggcggtg agactgcggc tagacaaccg     600
acttttggag agatgacact tgaggatttc ttggtgaagg ctggtgtggt tagagaacat     660
cccactaatc ctaaacctaa tccaaacccg aaccaaaacc aaaacccgtc tagtgtaata     720
cccgcagctg cacagcaaca gctttatggt gtgtttcaag aaccggtga tccttcattc     780 ccgggtcaag ctatgggtgt gggtgaccca tcaggttatg ctaaaaggac aggaggagga     840
gggtatcagc aggcgccacc agttcaggca ggtgtttgct atggaggtgg cgttgggttt     900
ggagcgggtg gacagcaaat gggaatggtt ggaccgttaa gcccggtgtc ttcagatgga     960
ttaggacatg gacaagtgga taacatagga ggtcagtatg gagtagatat gggagggcta    1020 agggaagga aagagtagt ggatggtcca gtggagaaag tagtggagag aagacagagg    1080
aggatgatca agaaccgcga gtctgctgct agatctagag caagaaaaca agcatataca    1140
gtggaattgg aagctgaact taaccagttg aaagaagaga atgcgcagct aaaacatgca    1200
ttggcggagt tggagaggaa gaggaagcaa cagtattttg agagtttgaa gtcaagggca    1260
caaccgaaat tgccgaaatc gaacgggaga ttgcggacat tgatgaggaa cccgagttgt    1320
ccactctaa                                                           1329
```

<210> SEQ ID NO 6
<211> LENGTH: 442
<212> TYPE: PRT
<213> ORGANISM: Arabidopsis thaliana

<400> SEQUENCE: 6

```
Met Val Thr Arg Glu Thr Lys Leu Thr Ser Glu Arg Glu Val Glu Ser
1               5                   10                  15

Ser Met Ala Gln Ala Arg His Asn Gly Gly Gly Gly Glu Asn His
            20                  25                  30

Pro Phe Thr Ser Leu Gly Arg Gln Ser Ser Ile Tyr Ser Leu Thr Leu
        35                  40                  45

Asp Glu Phe Gln His Ala Leu Cys Glu Asn Gly Lys Asn Phe Gly Ser
    50                  55                  60

Met Asn Met Asp Glu Phe Leu Val Ser Ile Trp Asn Ala Glu Glu Asn
65                  70                  75                  80

Asn Asn Asn Gln Gln Gln Ala Ala Ala Ala Gly Ser His Ser Val
                85                  90                  95

Pro Ala Asn His Asn Gly Phe Asn Asn Asn Asn Asn Gly Gly Glu
            100                 105                 110

Gly Gly Val Gly Val Phe Ser Gly Gly Ser Arg Gly Asn Glu Asp Ala
        115                 120                 125

Asn Asn Lys Arg Gly Ile Ala Asn Glu Ser Ser Leu Pro Arg Gln Gly
    130                 135                 140

Ser Leu Thr Leu Pro Ala Pro Leu Cys Arg Lys Thr Val Asp Glu Val
145                 150                 155                 160

Trp Ser Glu Ile His Arg Gly Gly Ser Gly Asn Gly Gly Asp Ser
                165                 170                 175

Asn Gly Arg Ser Ser Ser Asn Gly Gln Asn Asn Ala Gln Asn Gly
            180                 185                 190

Gly Glu Thr Ala Ala Arg Gln Pro Thr Phe Gly Glu Met Thr Leu Glu
        195                 200                 205

Asp Phe Leu Val Lys Ala Gly Val Val Arg Glu His Pro Thr Asn Pro
    210                 215                 220

Lys Pro Asn Pro Asn Pro Asn Gln Asn Gln Asn Pro Ser Ser Val Ile
225                 230                 235                 240

Pro Ala Ala Ala Gln Gln Gln Leu Tyr Gly Val Phe Gln Gly Thr Gly
                245                 250                 255

Asp Pro Ser Phe Pro Gly Gln Ala Met Gly Val Gly Asp Pro Ser Gly
            260                 265                 270

Tyr Ala Lys Arg Thr Gly Gly Gly Tyr Gln Gln Ala Pro Pro Val
        275                 280                 285

Gln Ala Gly Val Cys Tyr Gly Gly Val Gly Phe Gly Ala Gly Gly
    290                 295                 300

Gln Gln Met Gly Met Val Gly Pro Leu Ser Pro Val Ser Ser Asp Gly
305                 310                 315                 320

Leu Gly His Gly Gln Val Asp Asn Ile Gly Gly Gln Tyr Gly Val Asp
                325                 330                 335

Met Gly Gly Leu Arg Gly Arg Lys Arg Val Val Asp Gly Pro Val Glu
            340                 345                 350

Lys Val Val Glu Arg Arg Gln Arg Met Ile Lys Asn Arg Glu Ser
        355                 360                 365

Ala Ala Arg Ser Arg Ala Arg Lys Gln Ala Tyr Thr Val Glu Leu Glu
    370                 375                 380
```

```
Ala Glu Leu Asn Gln Leu Lys Glu Glu Asn Ala Gln Leu Lys His Ala
385                 390                 395                 400

Leu Ala Glu Leu Glu Arg Lys Arg Lys Gln Gln Tyr Phe Glu Ser Leu
            405                 410                 415

Lys Ser Arg Ala Gln Pro Lys Leu Pro Lys Ser Asn Gly Arg Leu Arg
        420                 425                 430

Thr Leu Met Arg Asn Pro Ser Cys Pro Leu
        435                 440

<210> SEQ ID NO 7
<211> LENGTH: 1179
<212> TYPE: DNA
<213> ORGANISM: Arabidopsis thaliana

<400> SEQUENCE: 7
atgggtactc acattgatat caacaactta ggcggcgata cttctagagg gaatgagtca      60
aagccattgg cgaggcagtc ttcgttatat tccttaacgt ttgatgagct tcagagcaca     120
ttaggtgagc cggggaaaga ttttgggtct atgaatatgg atgagttact caagaacata     180
tggactgctg aggatactca agcctttatg actactacat cttcggttgc agccccggga     240
cctagtggtt ttgttccggg aggaaatggt ttacagaggc aaggctcctt gaccttgcct     300
agaacgctta gtcagaagac tgtcgatgaa gtctggaaat acctgaattc gaagaaggt      360 agtaatggga atactggaac ggatgcgctt gagaggcaac agactttagg ggaaatgact     420
ctggaagatt tcttactccg tgctggcgtt gttaaagaag ataatactca gcagaacgaa     480
aacagtagta gcgggtttta tgctaacaac ggtgctgctg gtttggagtt tggatttggt     540
cagccgaatc aaaacagcat atcgttcaac gggaacaata gttctatgat catgaatcaa     600
gcacctggtt taggcctcaa agttggtgga accatgcagc agcagcagca gccacatcag     660
cagcagttgc agcagccaca tcagagactg cctccaacta tctttccaaa acaagcgaat     720
gtaacatttg cggcgcctgt aaatatggtc aacagggggtt tatttgagac tagcgcagat     780
ggtccagcca acagtaatat gggaggagca ggggtactg ttacagctac ttctcctggg      840
acgagcagtg cagaaaacaa tacttggtca tcaccagttc cttacgtgtt tggtcgggga     900
agaagaagca atacgggcct ggagaaggtt gttgagagaa ggcaaaagag aatgatcaag     960
aatcgggaat ccgctgctag atcaagggct cgaaaacagg cttataccttg gaactggaa    1020 gctgagattg aaagtctcaa gctagtgaat caagatttgc agaagaaaca ggctgaaata    1080
atgaaaaccc ataatagtga gctaaaggaa ttttcgaagc agcctccatt gctggccaaa    1140
agacaatgct tgagaagaac ccttaccggt ccgtggtaa                           1179

<210> SEQ ID NO 8
<211> LENGTH: 392
<212> TYPE: PRT
<213> ORGANISM: Arabidopsis thaliana

<400> SEQUENCE: 8

Met Gly Thr His Ile Asp Ile Asn Asn Leu Gly Gly Asp Thr Ser Arg
1               5                   10                  15

Gly Asn Glu Ser Lys Pro Leu Ala Arg Gln Ser Ser Leu Tyr Ser Leu
            20                  25                  30

Thr Phe Asp Glu Leu Gln Ser Thr Leu Gly Glu Pro Gly Lys Asp Phe
        35                  40                  45

Gly Ser Met Asn Met Asp Glu Leu Leu Lys Asn Ile Trp Thr Ala Glu
    50                  55                  60
```

```
Asp Thr Gln Ala Phe Met Thr Thr Thr Ser Ser Val Ala Ala Pro Gly
 65                  70                  75                  80

Pro Ser Gly Phe Val Pro Gly Gly Asn Gly Leu Gln Arg Gln Gly Ser
                 85                  90                  95

Leu Thr Leu Pro Arg Thr Leu Ser Gln Lys Thr Val Asp Glu Val Trp
            100                 105                 110

Lys Tyr Leu Asn Ser Lys Glu Gly Ser Asn Gly Asn Thr Gly Thr Asp
        115                 120                 125

Ala Leu Glu Arg Gln Gln Thr Leu Gly Glu Met Thr Leu Glu Asp Phe
    130                 135                 140

Leu Leu Arg Ala Gly Val Val Lys Glu Asp Asn Thr Gln Gln Asn Glu
145                 150                 155                 160

Asn Ser Ser Gly Phe Tyr Ala Asn Gly Ala Ala Gly Leu Glu
                165                 170                 175

Phe Gly Phe Gly Gln Pro Asn Gln Asn Ser Ile Ser Phe Asn Gly Asn
            180                 185                 190

Asn Ser Ser Met Ile Met Asn Gln Ala Pro Gly Leu Gly Leu Lys Val
        195                 200                 205

Gly Gly Thr Met Gln Gln Gln Gln Pro His Gln Gln Leu Gln
    210                 215                 220

Gln Pro His Gln Arg Leu Pro Pro Thr Ile Phe Pro Lys Gln Ala Asn
225                 230                 235                 240

Val Thr Phe Ala Ala Pro Val Asn Met Val Asn Arg Gly Leu Phe Glu
                245                 250                 255

Thr Ser Ala Asp Gly Pro Ala Asn Ser Asn Met Gly Gly Ala Gly Gly
            260                 265                 270

Thr Val Thr Ala Thr Ser Pro Gly Thr Ser Ser Ala Glu Asn Asn Thr
        275                 280                 285

Trp Ser Ser Pro Val Pro Tyr Val Phe Gly Arg Gly Arg Arg Ser Asn
    290                 295                 300

Thr Gly Leu Glu Lys Val Val Glu Arg Arg Gln Lys Arg Met Ile Lys
305                 310                 315                 320

Asn Arg Glu Ser Ala Ala Arg Ser Arg Ala Arg Lys Gln Ala Tyr Thr
                325                 330                 335

Leu Glu Leu Glu Ala Glu Ile Glu Ser Leu Lys Leu Val Asn Gln Asp
            340                 345                 350

Leu Gln Lys Lys Gln Ala Glu Ile Met Lys Thr His Asn Ser Glu Leu
        355                 360                 365

Lys Glu Phe Ser Lys Gln Pro Pro Leu Leu Ala Lys Arg Gln Cys Leu
    370                 375                 380

Arg Arg Thr Leu Thr Gly Pro Trp
385                 390

<210> SEQ ID NO 9
<211> LENGTH: 1113
<212> TYPE: DNA
<213> ORGANISM: Arabidopsis thaliana

<400> SEQUENCE: 9
atggatagtt actggagact taaaaacttg gtgaatgatt tgccagttag tacttcttta      60
agccgacaag gatcaatata ctcatggaca gtagatcagt ttcagaccag cttagggtta     120
gattgtggat caatgaacat ggatgagttg gttaagcata tatcaagtgc tgaagaaaca     180 caagagggt cgcagaggca aggctcaact actctgcctc caacacttag caaacaaaat     240
```

-continued

```
gttggtgaag tttggaaatc tatcacagag gaaaaacaca ccaataacaa tggaggagta    300
acaaacatta ctcatcttca gggacaacaa accttagggg aaatcactct tgaagagttt    360
ttcatccgtg ctggagcaag aggaggtaat accaatggtg gctccattca tgactcatcg    420
tcatcgattt ccggtaatcc acacactagt ttgggtgttc agattcagcc aaaagccatg    480
gtttctgatt ttatgaacaa tatggttcca aggagtcatg attcttattt gcatcaaaat    540
gtgaatggat ctatgtcaac atatcaacca caacaatcta tcatgtctat gccaaatggt    600
tattcttatg gaaaacaaat ccgattctca aatggttcct tgggatctgg taaccaaagt    660
ctccaagata cgaagagaag cttggtccca agtgttgcga caattccaag tgaagccata    720
acatgttcac cggttacccc atttccaaca ttaaatggga aacaaaagat taacggtgag    780
tcttcattac tctcaccatc tccatacatt agtaatggta gtactagtac aagaggtggg    840
aagattaata gtgaaattac cgcggaaaaa caattcgttg acaaaaagct taggagaaag    900
attaagaacc gagaatccgc agcgagatca cgggctcgaa agcaagctca aactatggag    960
gttgaagttg aacttgaaaa cttaaagaaa gattatgaag agctactaaa acaacatgta   1020
gagttgcgga aaagacaaat ggaaccagga atgattagcc ttcatgaacg accggagaga   1080
aagctgagga gaacgaaatc ggacatcaag tga                                1113
```

<210> SEQ ID NO 10
<211> LENGTH: 370
<212> TYPE: PRT
<213> ORGANISM: Arabidopsis thaliana

<400> SEQUENCE: 10

```
Met Asp Ser Tyr Trp Arg Leu Lys Asn Leu Val Asn Asp Leu Pro Val
1               5                   10                  15

Ser Thr Ser Leu Ser Arg Gln Gly Ser Ile Tyr Ser Trp Thr Val Asp
            20                  25                  30

Gln Phe Gln Thr Ser Leu Gly Leu Asp Cys Gly Ser Met Asn Met Asp
        35                  40                  45

Glu Leu Val Lys His Ile Ser Ser Ala Glu Glu Thr Gln Glu Gly Ser
    50                  55                  60

Gln Arg Gln Gly Ser Thr Thr Leu Pro Pro Thr Leu Ser Lys Gln Asn
65                  70                  75                  80

Val Gly Glu Val Trp Lys Ser Ile Thr Glu Glu Lys His Thr Asn Asn
                85                  90                  95

Asn Gly Gly Val Thr Asn Ile Thr His Leu Gln Gly Gln Gln Thr Leu
            100                 105                 110

Gly Glu Ile Thr Leu Glu Glu Phe Phe Ile Arg Ala Gly Ala Arg Gly
        115                 120                 125

Gly Asn Thr Asn Gly Gly Ser Ile His Asp Ser Ser Ser Ile Ser
    130                 135                 140

Gly Asn Pro His Thr Ser Leu Gly Val Gln Ile Gln Pro Lys Ala Met
145                 150                 155                 160

Val Ser Asp Phe Met Asn Asn Met Val Pro Arg Ser His Asp Ser Tyr
                165                 170                 175

Leu His Gln Asn Val Asn Gly Ser Met Ser Thr Tyr Gln Pro Gln Gln
            180                 185                 190

Ser Ile Met Ser Met Pro Asn Gly Tyr Ser Tyr Gly Lys Gln Ile Arg
        195                 200                 205

Phe Ser Asn Gly Ser Leu Gly Ser Gly Asn Gln Ser Leu Gln Asp Thr
```

```
            210                 215                 220
Lys Arg Ser Leu Val Pro Ser Val Ala Thr Ile Pro Ser Glu Ala Ile
225                 230                 235                 240

Thr Cys Ser Pro Val Thr Pro Phe Pro Thr Leu Asn Gly Lys Gln Lys
                245                 250                 255

Ile Asn Gly Glu Ser Ser Leu Leu Ser Pro Ser Pro Tyr Ile Ser Asn
            260                 265                 270

Gly Ser Thr Ser Thr Arg Gly Gly Lys Ile Asn Ser Glu Ile Thr Ala
        275                 280                 285

Glu Lys Gln Phe Val Asp Lys Lys Leu Arg Arg Lys Ile Lys Asn Arg
    290                 295                 300

Glu Ser Ala Ala Arg Ser Arg Ala Arg Lys Gln Ala Gln Thr Met Glu
305                 310                 315                 320

Val Glu Val Glu Leu Glu Asn Leu Lys Lys Asp Tyr Glu Glu Leu Leu
                325                 330                 335

Lys Gln His Val Glu Leu Arg Lys Arg Gln Met Glu Pro Gly Met Ile
            340                 345                 350

Ser Leu His Glu Arg Pro Glu Arg Lys Leu Arg Arg Thr Lys Ser Asp
        355                 360                 365

Ile Lys
    370

<210> SEQ ID NO 11
<211> LENGTH: 1251
<212> TYPE: DNA
<213> ORGANISM: Arabidopsis thaliana

<400> SEQUENCE: 11
atggatggta gtatgaattt ggggaatgag ccaccaggag atggtggtgg aggtggaggg      60
ttgactagac aaggttcgat atactcgttg acgtttgatg agtttcagag cagtgtaggg     120
aaagattttg ggtcaatgaa catggatgag ttgttaaaga atatatggag tgctgaagaa     180
acacaagcca tggctagtgg tgtggttcca gttcttggtg aggtcaaga gggtttgcag      240 ctgcagaggc aaggctcgtt gactctgcct cgaacgctta gtcagaagac ggttgatcaa     300
gtttggaaag atctatccaa agttggaagt agtggagtag ggggaagtaa cttgtctcag     360
gtggctcagg ctcagagtca gagtcagagt cagaggcagc aaacattagg tgaagtaact     420
ttggaggagt ttttggttcg tgctggtgtt gtgagagagg aagctcaggt tgctgcaaga     480
gctcagattg ctgagaacaa taaaggcggt tactttggta atgatgccaa cacaggtttc     540
tctgtcgagt ttcagcagcc ttctccacga gttgttgccg ctggtgtaat gggaaatctt     600
ggtgcagaga ctgcaaattc tttgcaggtt caaggttcta gtttgcctct gaatgtgaat     660
ggagctagaa caacatacca gcaatcgcaa cagcaacagc caatcatgcc taagcagcct     720
ggttttggtt atgaaacaca aatgggtcag cttaatagtc ctgggataag aggtggtggt     780
cttgtgggac ttggagatca gtctttaacg aacaatgtgg gctttgtcca aggtgcttct     840
gctgcaattc ctggagcttt aggcgttggt gctgtgtcgc ctgttacgcc attgtcatca     900
gaagggatag ggaagagtaa tggtgattct tcatcactct ctccgtctcc ttacatgttt     960
aatggtggtg tgagaggtag aaagagtggc actgtggaga agttgtagag agaggcaa    1020 aggagaatga taaagaaccg agaatcagct gcaaggtccc gggccaggaa acaggcttac    1080
accgtggagc ttgaagctga agttgcaaag ttaaaggaag agaatgacga gttacaacga    1140
aagcaggcaa ggatcatgga aatgcaaaag aatcaggaga cggagatgag gaatcttctg    1200
```
caaggaggtc caaagaaaaa gctgaggagg acagagtcgg gaccttggtg a         1251

<210> SEQ ID NO 12
<211> LENGTH: 416
<212> TYPE: PRT
<213> ORGANISM: Arabidopsis thaliana

<400> SEQUENCE: 12

Met Asp Gly Ser Met Asn Leu Gly Asn Glu Pro Gly Asp Gly Gly
1               5                   10                  15

Gly Gly Gly Gly Leu Thr Arg Gln Gly Ser Ile Tyr Ser Leu Thr Phe
            20                  25                  30

Asp Glu Phe Gln Ser Ser Val Gly Lys Asp Phe Gly Ser Met Asn Met
        35                  40                  45

Asp Glu Leu Leu Lys Asn Ile Trp Ser Ala Glu Glu Thr Gln Ala Met
    50                  55                  60

Ala Ser Gly Val Val Pro Val Leu Gly Gly Gln Glu Gly Leu Gln
65                  70                  75                  80

Leu Gln Arg Gln Gly Ser Leu Thr Leu Pro Arg Thr Leu Ser Gln Lys
                85                  90                  95

Thr Val Asp Gln Val Trp Lys Asp Leu Ser Lys Val Gly Ser Ser Gly
            100                 105                 110

Val Gly Gly Ser Asn Leu Ser Gln Val Ala Gln Ala Gln Ser Gln Ser
        115                 120                 125

Gln Ser Gln Arg Gln Gln Thr Leu Gly Glu Val Thr Leu Glu Glu Phe
    130                 135                 140

Leu Val Arg Ala Gly Val Val Arg Glu Glu Ala Gln Val Ala Ala Arg
145                 150                 155                 160

Ala Gln Ile Ala Glu Asn Asn Lys Gly Gly Tyr Phe Gly Asn Asp Ala
                165                 170                 175

Asn Thr Gly Phe Ser Val Glu Phe Gln Gln Pro Ser Pro Arg Val Val
            180                 185                 190

Ala Ala Gly Val Met Gly Asn Leu Gly Ala Glu Thr Ala Asn Ser Leu
        195                 200                 205

Gln Val Gln Gly Ser Ser Leu Pro Leu Asn Val Asn Gly Ala Arg Thr
    210                 215                 220

Thr Tyr Gln Gln Ser Gln Gln Gln Pro Ile Met Pro Lys Gln Pro
225                 230                 235                 240

Gly Phe Gly Tyr Gly Thr Gln Met Gly Gln Leu Asn Ser Pro Gly Ile
                245                 250                 255

Arg Gly Gly Gly Leu Val Gly Leu Gly Asp Gln Ser Leu Thr Asn Asn
            260                 265                 270

Val Gly Phe Val Gln Gly Ala Ser Ala Ala Ile Pro Gly Ala Leu Gly
        275                 280                 285

Val Gly Ala Val Ser Pro Val Thr Pro Leu Ser Ser Glu Gly Ile Gly
    290                 295                 300

Lys Ser Asn Gly Asp Ser Ser Leu Ser Pro Ser Pro Tyr Met Phe
305                 310                 315                 320

Asn Gly Gly Val Arg Gly Arg Lys Ser Gly Thr Val Glu Lys Val Val
                325                 330                 335

Glu Arg Arg Gln Arg Arg Met Ile Lys Asn Arg Glu Ser Ala Ala Arg
            340                 345                 350

Ser Arg Ala Arg Lys Gln Ala Tyr Thr Val Glu Leu Glu Ala Glu Val
        355                 360                 365

```
Ala Lys Leu Lys Glu Glu Asn Asp Glu Leu Gln Arg Lys Gln Ala Arg
        370                 375                 380

Ile Met Glu Met Gln Lys Asn Gln Glu Thr Glu Met Arg Asn Leu Leu
385                 390                 395                 400

Gln Gly Gly Pro Lys Lys Leu Arg Arg Thr Glu Ser Gly Pro Trp
                405                 410                 415

<210> SEQ ID NO 13
<211> LENGTH: 1365
<212> TYPE: DNA
<213> ORGANISM: Arabidopsis thaliana

<400> SEQUENCE: 13
atggggtcta gattaaactt caagagcttt gttgatggtg tgagtgagca gcagccaacg     60
gtggggacta gtcttccatt gactaggcag aactctgtgt tctcgttaac ctttgatgag    120
tttcagaact catggggtgg tggaattggg aaagattttg gtctatgaa catggatgag     180 ctcttgaaga acatttggac tgcagaggaa agtcattcaa tgatgggaaa caataccagt    240
tacaccaaca tcagcaatgg taatagtgga aacactgtta ttaacggcgg tggtaacaac    300
attggtgggt tagctgttgg tgtgggagga gaaagtggtg ttttttcac tggtgggagt     360 ttgcagagac aaggttcact taccttgcct cggacgatta gtcagaaaag ggttgatgat    420
gtctggaagg agctgatgaa ggaggatgac attggaaatg tgttgttaa tggtgggaca     480 agcggaattc cgcagaggca acaaacgctg gagagatga cttttggagga gttttttggtc    540 agggctggtg tggttaggga agaacctcaa ccggtggaga gtgtaactaa cttcaatggc    600
ggattctatg gatttggcag taatggaggt cttgggacag ctagtaatgg gtttgttgca    660
aaccaacctc aagatttgtc aggaaatgga gtagcggtga caggatct gctgactgct     720 caaactcagc cactacagat gcagcagcca cagatggtgc agcagccaca gatggtgcag    780
cagccgcaac aactgataca gacgcaggag aggcctttc ccaaacagac cactatagca    840
ttttccaaca ctgttgatgt ggttaaccgt tctcaacctg caacacagtg ccaggaagtg    900
aagccttcaa tacttggaat tcataaccat cctatgaaca caatctact gcaagctgtc    960 gattttaaaa caggagtaac ggttgcagca gtatctcctg gaagccagat gtcacctgat   1020
ctgactccaa agagcgccct ggatgcatct ttgtcccctg ttccttacat gtttgggcga   1080
gtgagaaaaa caggtgcagt tctggagaaa gtgattgaga gaaggcaaaa aaggatgata   1140 aagaatagggg aatcagctgc aagatcccgc gctcgcaagc aagcttatac gatggaactg   1200
gaagcagaaa ttgcgcaact caaagaattg aatgaagagt tgcagaagaa acaagttgaa   1260
atcatggaaa agcagaaaaa tcagcttctg gagcctctgc gccagccatg gggaatggga   1320
tgcaaaaggc aatgcttgcg aaggacattg acgggtccct ggtag                   1365

<210> SEQ ID NO 14
<211> LENGTH: 454
<212> TYPE: PRT
<213> ORGANISM: Arabidopsis thaliana

<400> SEQUENCE: 14

Met Gly Ser Arg Leu Asn Phe Lys Ser Phe Val Asp Gly Val Ser Glu
1               5                   10                  15

Gln Gln Pro Thr Val Gly Thr Ser Leu Pro Leu Thr Arg Gln Asn Ser
            20                  25                  30

Val Phe Ser Leu Thr Phe Asp Glu Phe Gln Asn Ser Trp Gly Gly Gly
```

```
                  35                  40                  45
Ile Gly Lys Asp Phe Gly Ser Met Asn Met Asp Glu Leu Leu Lys Asn
 50                  55                  60

Ile Trp Thr Ala Glu Glu Ser His Ser Met Met Gly Asn Asn Thr Ser
 65                  70                  75                  80

Tyr Thr Asn Ile Ser Asn Gly Asn Ser Gly Asn Thr Val Ile Asn Gly
                 85                  90                  95

Gly Gly Asn Asn Ile Gly Gly Leu Ala Val Gly Val Gly Gly Glu Ser
                100                 105                 110

Gly Gly Phe Phe Thr Gly Gly Ser Leu Gln Arg Gln Gly Ser Leu Thr
                115                 120                 125

Leu Pro Arg Thr Ile Ser Gln Lys Arg Val Asp Asp Val Trp Lys Glu
130                 135                 140

Leu Met Lys Glu Asp Asp Ile Gly Asn Gly Val Val Asn Gly Gly Thr
145                 150                 155                 160

Ser Gly Ile Pro Gln Arg Gln Gln Thr Leu Gly Glu Met Thr Leu Glu
                165                 170                 175

Glu Phe Leu Val Arg Ala Gly Val Val Arg Glu Glu Pro Gln Pro Val
                180                 185                 190

Glu Ser Val Thr Asn Phe Asn Gly Gly Phe Tyr Gly Phe Gly Ser Asn
                195                 200                 205

Gly Gly Leu Gly Thr Ala Ser Asn Gly Phe Val Ala Asn Gln Pro Gln
                210                 215                 220

Asp Leu Ser Gly Asn Gly Val Ala Val Arg Gln Asp Leu Leu Thr Ala
225                 230                 235                 240

Gln Thr Gln Pro Leu Gln Met Gln Gln Pro Gln Met Val Gln Gln Pro
                245                 250                 255

Gln Met Val Gln Gln Pro Gln Leu Ile Gln Thr Gln Glu Arg Pro
                260                 265                 270

Phe Pro Lys Gln Thr Thr Ile Ala Phe Ser Asn Thr Val Asp Val Val
                275                 280                 285

Asn Arg Ser Gln Pro Ala Thr Gln Cys Gln Glu Val Lys Pro Ser Ile
290                 295                 300

Leu Gly Ile His Asn His Pro Met Asn Asn Leu Leu Gln Ala Val
305                 310                 315                 320

Asp Phe Lys Thr Gly Val Thr Val Ala Ala Val Ser Pro Gly Ser Gln
                325                 330                 335

Met Ser Pro Asp Leu Thr Pro Lys Ser Ala Leu Asp Ala Ser Leu Ser
                340                 345                 350

Pro Val Pro Tyr Met Phe Gly Arg Val Arg Lys Thr Gly Ala Val Leu
                355                 360                 365

Glu Lys Val Ile Glu Arg Arg Gln Lys Arg Met Ile Lys Asn Arg Glu
                370                 375                 380

Ser Ala Ala Arg Ser Arg Ala Arg Lys Gln Ala Tyr Thr Met Glu Leu
385                 390                 395                 400

Glu Ala Glu Ile Ala Gln Leu Lys Glu Leu Asn Glu Glu Leu Gln Lys
                405                 410                 415

Lys Gln Val Glu Ile Met Glu Lys Gln Lys Asn Gln Leu Leu Glu Pro
                420                 425                 430

Leu Arg Gln Pro Trp Gly Met Gly Cys Lys Arg Gln Cys Leu Arg Arg
                435                 440                 445

Thr Leu Thr Gly Pro Trp
450
```

<210> SEQ ID NO 15
<211> LENGTH: 1350
<212> TYPE: DNA
<213> ORGANISM: Arabidopsis thaliana

<400> SEQUENCE: 15

```
atgggtcta gattaaactt caagagcttt gttgatggtg tgagtgagca gcagccaacg      60
gtggggacta gtcttccatt gactaggcag aactctgtgt tctcgttaac ctttgatgag     120
tttcagaact catggggtgg tggaattggg aaagattttg gtctatgaa catggatgag      180
ctcttgaaga acatttggac tgcagaggaa agtcattcaa tgatgggaaa caataccagt     240
tacaccaaca tcagcaatgg taatagtgga aacactgtta ttaacggcgg tggtaacaac     300
attggtgggt tagctgttgg tgtgggagga gaaagtggtg gttttttcac tggtgggagt     360
ttgcagagac aaggttcact taccttgcct cggacgatta gtcagaaaag ggttgatgat     420
gtctggaagg agctgatgaa ggaggatgac attggaaatg tgttgttaa tggtgggaca      480
agcggaattc cgcagaggca acaaacgctg gagagatga cttggagga gttttttggtc     540
agggctggtg tggttaggga agaacctcaa ccggtggaga gtgtaactaa cttcaatggc     600
ggattctatg gatttggcag taatggaggt cttgggacag ctagtaatgg gtttgttgca     660
aaccaacctc aagatttgtc aggaaatgga gtagcggtga cacaggatct gctgactgct     720
caaactcagc cactacagat gcagcagcca cagatggtgc agcagccaca gatggtgcag     780
cagccgcaac aactgataca gacgcaggag aggccttttc ccaaacagac cactatagca     840
ttttccaaca ctgttgatgt ggttaaccgt tctcaacctg caacacagtg ccaggaagtg     900
aagccttcaa acttggaat tcataaccat cctatgaaca caatctact gcaagctgtc      960
gattttaaaa caggagtaac ggttgcagca gtatctcctg gaagccagat gtcacctgat    1020
ctgactccaa agagcgccct ggatgcatct ttgtccctg ttccttacat gtttgggcga    1080
gtgagaaaaa caggtgcagt tctggagaaa gtgattgaga aaggcaaaa aaggatgata    1140
aagaataggg aatcagctgc aagatcccgc gctcgcaagc aagcttatac gatggaactg    1200
gaagcagaaa ttgcgcaact caaagaattg aatgaagagt tgcagaagaa acaagtgtgt    1260
ctcgcttctt ccctatcaca attaagaatc tcgagatttt catatttctc tgaggttgta    1320
ttcactgacc aaatgtttca tgcaggttga                                    1350
```

<210> SEQ ID NO 16
<211> LENGTH: 449
<212> TYPE: PRT
<213> ORGANISM: Arabidopsis thaliana

<400> SEQUENCE: 16

```
Met Gly Ser Arg Leu Asn Phe Lys Ser Phe Val Asp Gly Val Ser Glu
1               5                   10                  15

Gln Gln Pro Thr Val Gly Thr Ser Leu Pro Leu Thr Arg Gln Asn Ser
            20                  25                  30

Val Phe Ser Leu Thr Phe Asp Glu Phe Gln Asn Ser Trp Gly Gly Gly
        35                  40                  45

Ile Gly Lys Asp Phe Gly Ser Met Asn Met Asp Glu Leu Leu Lys Asn
    50                  55                  60

Ile Trp Thr Ala Glu Glu Ser His Ser Met Met Gly Asn Asn Thr Ser
65                  70                  75                  80

Tyr Thr Asn Ile Ser Asn Gly Asn Ser Gly Asn Thr Val Ile Asn Gly
```

```
                    85                  90                  95
Gly Gly Asn Asn Ile Gly Gly Leu Ala Val Gly Val Gly Gly Glu Ser
            100                 105                 110
Gly Gly Phe Phe Thr Gly Gly Ser Leu Gln Arg Gln Gly Ser Leu Thr
        115                 120                 125
Leu Pro Arg Thr Ile Ser Gln Lys Arg Val Asp Asp Val Trp Lys Glu
    130                 135                 140
Leu Met Lys Glu Asp Asp Ile Gly Asn Gly Val Val Asn Gly Gly Thr
145                 150                 155                 160
Ser Gly Ile Pro Gln Arg Gln Gln Thr Leu Gly Glu Met Thr Leu Glu
                165                 170                 175
Glu Phe Leu Val Arg Ala Gly Val Val Arg Glu Glu Pro Gln Pro Val
            180                 185                 190
Glu Ser Val Thr Asn Phe Asn Gly Gly Phe Tyr Gly Phe Gly Ser Asn
        195                 200                 205
Gly Gly Leu Gly Thr Ala Ser Asn Gly Phe Val Ala Asn Gln Pro Gln
    210                 215                 220
Asp Leu Ser Gly Asn Gly Val Ala Val Arg Gln Asp Leu Leu Thr Ala
225                 230                 235                 240
Gln Thr Gln Pro Leu Gln Met Gln Gln Pro Gln Met Val Gln Gln Pro
                245                 250                 255
Gln Met Val Gln Gln Pro Gln Leu Ile Gln Thr Gln Glu Arg Pro
            260                 265                 270
Phe Pro Lys Gln Thr Thr Ile Ala Phe Ser Asn Thr Val Asp Val Val
        275                 280                 285
Asn Arg Ser Gln Pro Ala Thr Gln Cys Gln Glu Val Lys Pro Ser Ile
    290                 295                 300
Leu Gly Ile His Asn His Pro Met Asn Asn Asn Leu Leu Gln Ala Val
305                 310                 315                 320
Asp Phe Lys Thr Gly Val Thr Val Ala Ala Val Ser Pro Gly Ser Gln
                325                 330                 335
Met Ser Pro Asp Leu Thr Pro Lys Ser Ala Leu Asp Ala Ser Leu Ser
            340                 345                 350
Pro Val Pro Tyr Met Phe Gly Arg Val Arg Lys Thr Gly Ala Val Leu
        355                 360                 365
Glu Lys Val Ile Glu Arg Arg Gln Lys Arg Met Ile Lys Asn Arg Glu
    370                 375                 380
Ser Ala Ala Arg Ser Arg Ala Arg Lys Gln Ala Tyr Thr Met Glu Leu
385                 390                 395                 400
Glu Ala Glu Ile Ala Gln Leu Lys Glu Leu Asn Glu Glu Leu Gln Lys
                405                 410                 415
Lys Gln Val Cys Leu Ala Ser Ser Leu Ser Gln Leu Arg Ile Ser Arg
            420                 425                 430
Phe Ser Tyr Phe Leu Glu Val Val Phe Thr Asp Gln Met Phe His Ala
        435                 440                 445
Gly
```

<210> SEQ ID NO 17
<211> LENGTH: 1296
<212> TYPE: DNA
<213> ORGANISM: Arabidopsis thaliana

<400> SEQUENCE: 17
atgggaactc acatcaattt caacaactta ggaggtggtg gtcatcctgg aggggaaggg    60

```
agtagtaacc agatgaagcc aacgggtagt gtcatgccct tggctaggca gtcctcggtc      120
tactccctta cctttgatga gttacagaac acactaggtg gaccgggaaa agatttcggg      180
tcgatgaaca tggatgaact cctgaagagc atatggactg ctgaggaagc tcaggccatg      240
gccatgactt ctgcgccagc tgctacagcg gtagcgcaac ctggtgctgg tatcccaccc      300
ccaggtggga atctccagag gcaaggttcg ttgacgttgc ctagaacaat tagtcagaag      360
actgttgatg aggtgtggaa atgtttgatc accaaggatg gtaatatgga aggtagcagc      420
ggaggcggtg gtgagtcgaa tgtgcctcct ggaaggcaac agactttagg ggaaatgaca      480
cttgaagaat ttctgttccg tgctggggtt gtaagagaag ataactgtgt tcaacagatg      540
ggtcaggtca acggaaacaa taacaatggg ttttatggta acagcactgc tgctggcggc      600
ttaggttttg gatttggtca gccaaatcaa aacagcataa cattcaatgg tactaatgat      660
tctatgatct tgaatcagcc acctggttta gggctcaaaa tgggtggaac aatgcagcag      720
caacaacaac aacagcagtt gcttcagcag caacaacagc agatgcagca gctgaatcag      780
cctcatccac agcagcggct gcctcaaacc attttttccta acaagcaaa cgtagcattt      840 tctgcgcctg tgaatataac caacaagggt tttgctgggg ctgcaaataa ttctatcaac      900
aataataatg gattagctag ttacggagga accggggtca ctgttgcagc aacttctcca      960
ggaacaagca gcgcagaaaa taattcttta tcaccagttc cgtatgtgct taatcgagga     1020
cgaagaagca atacaggtct agagaaggtt atcgagagga ggcaaaggag aatgatcaag     1080
aatcgggaat cagctgctag atcaagagct cgaaagcagg cttatacatt ggaactgaaa     1140
gccgaaattg aaaagctcaa gaaaacgaat caagaactgc agaaaaaaca ggctgaaatg     1200
gtggaaatgc agaagaatga gctgaaagaa acgtcgaagc gaccgtgggg cagcaaaagg     1260
caatgcttga gaaggacatt aaccggacca tggtga                              1296
```

<210> SEQ ID NO 18
<211> LENGTH: 431
<212> TYPE: PRT
<213> ORGANISM: Arabidopsis thaliana

<400> SEQUENCE: 18

```
Met Gly Thr His Ile Asn Phe Asn Asn Leu Gly Gly Gly His Pro
1               5                   10                  15

Gly Gly Glu Gly Ser Ser Asn Gln Met Lys Pro Thr Gly Ser Val Met
            20                  25                  30

Pro Leu Ala Arg Gln Ser Ser Val Tyr Ser Leu Thr Phe Asp Glu Leu
        35                  40                  45

Gln Asn Thr Leu Gly Gly Pro Gly Lys Asp Phe Gly Ser Met Asn Met
    50                  55                  60

Asp Glu Leu Leu Lys Ser Ile Trp Thr Ala Glu Glu Ala Gln Ala Met
65                  70                  75                  80

Ala Met Thr Ser Ala Pro Ala Ala Thr Ala Val Ala Gln Pro Gly Ala
                85                  90                  95

Gly Ile Pro Pro Pro Gly Gly Asn Leu Gln Arg Gln Gly Ser Leu Thr
            100                 105                 110

Leu Pro Arg Thr Ile Ser Gln Lys Thr Val Asp Glu Val Trp Lys Cys
        115                 120                 125

Leu Ile Thr Lys Asp Gly Asn Met Glu Gly Ser Ser Gly Gly Gly Gly
    130                 135                 140

Glu Ser Asn Val Pro Pro Gly Arg Gln Gln Thr Leu Gly Glu Met Thr
```

|     |     |     |     | 145 |     |     |     | 150 |     |     |     | 155 |     |     |     | 160 |
| --- | --- | --- | --- | --- | --- | --- | --- | --- | --- | --- | --- | --- | --- | --- | --- | --- |

Leu Glu Glu Phe Leu Phe Arg Ala Gly Val Val Arg Glu Asp Asn Cys
                165                 170                 175

Val Gln Gln Met Gly Gln Val Asn Gly Asn Asn Asn Gly Phe Tyr
            180                 185                 190

Gly Asn Ser Thr Ala Ala Gly Gly Leu Gly Phe Gly Phe Gly Gln Pro
            195                 200                 205

Asn Gln Asn Ser Ile Thr Phe Asn Gly Thr Asn Asp Ser Met Ile Leu
        210                 215                 220

Asn Gln Pro Pro Gly Leu Gly Leu Lys Met Gly Gly Thr Met Gln Gln
225                 230                 235                 240

Gln Gln Gln Gln Gln Gln Leu Leu Gln Gln Gln Gln Gln Met Gln
                245                 250                 255

Gln Leu Asn Gln Pro His Pro Gln Gln Arg Leu Pro Gln Thr Ile Phe
            260                 265                 270

Pro Lys Gln Ala Asn Val Ala Phe Ser Ala Pro Val Asn Ile Thr Asn
            275                 280                 285

Lys Gly Phe Ala Gly Ala Ala Asn Asn Ser Ile Asn Asn Asn Asn Gly
            290                 295                 300

Leu Ala Ser Tyr Gly Gly Thr Gly Val Thr Val Ala Ala Thr Ser Pro
305                 310                 315                 320

Gly Thr Ser Ser Ala Glu Asn Asn Ser Leu Ser Pro Val Pro Tyr Val
            325                 330                 335

Leu Asn Arg Gly Arg Arg Ser Asn Thr Gly Leu Glu Lys Val Ile Glu
            340                 345                 350

Arg Arg Gln Arg Arg Met Ile Lys Asn Arg Glu Ser Ala Ala Arg Ser
            355                 360                 365

Arg Ala Arg Lys Gln Ala Tyr Thr Leu Glu Leu Glu Ala Glu Ile Glu
            370                 375                 380

Lys Leu Lys Lys Thr Asn Gln Glu Leu Gln Lys Lys Gln Ala Glu Met
385                 390                 395                 400

Val Glu Met Gln Lys Asn Glu Leu Lys Glu Thr Ser Lys Arg Pro Trp
            405                 410                 415

Gly Ser Lys Arg Gln Cys Leu Arg Arg Thr Leu Thr Gly Pro Trp
            420                 425                 430

<210> SEQ ID NO 19
<211> LENGTH: 894
<212> TYPE: DNA
<213> ORGANISM: Arabidopsis thaliana

<400> SEQUENCE: 19

| | |
|---|---|
| atggattctc agaggggtat tgttgaacaa gctaaatctc agtccttgaa taggcaaagc | 60 |
| tctctttaca gcttaacact tgatgaggtt caaaatcact ggggagttc tggtaaagct | 120 |
| ctgggaagca tgaaccttga tgagcttttg aagagtgtct gttctgttga agctaatcag | 180 |
| ccatcgtcta tggctgtcaa tggtggagca gctgctcagg gggtctttc tcgccagggg | 240 |
| agtttgactt tgcctcggga tctcagcaaa aagactgttg atgaggtttg gaaagacatt | 300 |
| cagcagaata agaatggagg tagtgctcat gagaggaggg ataagcagcc tacacttggg | 360 |
| gaaatgacgc ttgaagacct gttgttgaaa gcaggagtgg tcactgagac tatccctggt | 420 |
| tcgaaccatg atggtcctgt tggtggtggt agtgctggtt caggtgctgg tttagggcaa | 480 |
| aacattactc aagttggccc atggattcaa tatcatcagc tcccatcaat gccacagcct | 540 |

```
caagcattta tgccctatcc ggtttcagat atgcaagcaa tggtgtctca gtcttctttg    600
atgggtggtt tgtcagatac acaaactcct ggaaggaaga gggtagcttc aggagaagtt    660
gtagagaaga ctgtagagag gaggcagaag agaatgataa agaacagaga gtctgctgct    720
cgttcccgag ctaggaaaca ggcttacact catgagctag agatcaaagt ttcacggtta    780
gaagaagaaa acgaaagact caggaagcaa aaggaggtgg aaaaaatcct cccaagtgta    840
ccaccgcctg atcccaagcg gcagctccga cggacaagct cggctccttt ctga          894
```

<210> SEQ ID NO 20
<211> LENGTH: 297
<212> TYPE: PRT
<213> ORGANISM: Arabidopsis thaliana

<400> SEQUENCE: 20

```
Met Asp Ser Gln Arg Gly Ile Val Glu Gln Ala Lys Ser Gln Ser Leu
1               5                   10                  15

Asn Arg Gln Ser Ser Leu Tyr Ser Leu Thr Leu Asp Glu Val Gln Asn
            20                  25                  30

His Leu Gly Ser Ser Gly Lys Ala Leu Gly Ser Met Asn Leu Asp Glu
        35                  40                  45

Leu Leu Lys Ser Val Cys Ser Val Glu Ala Asn Gln Pro Ser Ser Met
    50                  55                  60

Ala Val Asn Gly Gly Ala Ala Gln Glu Gly Leu Ser Arg Gln Gly
65                  70                  75                  80

Ser Leu Thr Leu Pro Arg Asp Leu Ser Lys Lys Thr Val Asp Glu Val
                85                  90                  95

Trp Lys Asp Ile Gln Gln Asn Lys Asn Gly Gly Ser Ala His Glu Arg
            100                 105                 110

Arg Asp Lys Gln Pro Thr Leu Gly Glu Met Thr Leu Glu Asp Leu Leu
        115                 120                 125

Leu Lys Ala Gly Val Val Thr Glu Thr Ile Pro Gly Ser Asn His Asp
    130                 135                 140

Gly Pro Val Gly Gly Gly Ser Ala Gly Ser Gly Ala Gly Leu Gly Gln
145                 150                 155                 160

Asn Ile Thr Gln Val Gly Pro Trp Ile Gln Tyr His Gln Leu Pro Ser
                165                 170                 175

Met Pro Gln Pro Gln Ala Phe Met Pro Tyr Pro Val Ser Asp Met Gln
            180                 185                 190

Ala Met Val Ser Gln Ser Ser Leu Met Gly Gly Leu Ser Asp Thr Gln
        195                 200                 205

Thr Pro Gly Arg Lys Arg Val Ala Ser Gly Glu Val Val Glu Lys Thr
    210                 215                 220

Val Glu Arg Arg Gln Lys Arg Met Ile Lys Asn Arg Glu Ser Ala Ala
225                 230                 235                 240

Arg Ser Arg Ala Arg Lys Gln Ala Tyr Thr His Glu Leu Glu Ile Lys
                245                 250                 255

Val Ser Arg Leu Glu Glu Glu Asn Glu Arg Leu Arg Lys Gln Lys Glu
            260                 265                 270

Val Glu Lys Ile Leu Pro Ser Val Pro Pro Asp Pro Lys Arg Gln
        275                 280                 285

Leu Arg Arg Thr Ser Ser Ala Pro Phe
    290                 295
```

<210> SEQ ID NO 21

<211> LENGTH: 996
<212> TYPE: DNA
<213> ORGANISM: Arabidopsis thaliana

<400> SEQUENCE: 21

```
atgtcggttt tcgaatcgga gacttcgaac ttccacgtct acaacaacca cgaaatccaa    60
acgcaaccgc aaatgcaaac gtttctgtcg gaggaggaac cggtagggag acagaactcg   120
attttgtcac taactcttga cgaaattcag atgaaaagcg gtaagagctt ggagcgatg    180
aacatggacg agttcctagc gaacttgtgg acaaccgttg aagaaaacga caacgaagga   240
ggtgggctc acaacgacgg agagaagccg gcggtgctgc cacgtcaagg gtcgttgtcc   300
ctccctgtgc ctttatgcaa gaaaacggtc gacgaggttt ggctcgagat acaaaacggt   360
gtacaacaac atccaccgtc gtcgaattcc ggtcaaaact ccgccgaaaa tattcgccgg   420
caacaaaccc ttggtgagat cactctcgag gattttcttg ttaaggctgg tgttgtacaa   480
gaaccgttga agacaacgat gaggatgtcg agttctgatt ttggttataa ccccgagttt   540
ggagttggtt tacattgtca gaaccaaaac aattatggtg ataaccggtc ggtttatagt   600
gaaaaccgac cgttttactc ggttttggga gaatcttcaa gctgtatgac cgggaatggg   660
aggagtaatc agtatctgac cggtttagat gcttttcgga tcaagaaacg gataattgat   720
ggtccacctg aaattttgat ggagcggaga caacggcgaa tgattaaaaa ccgcgaatct   780
gcggctcggt ctcgagcccg agacaagct tatactgtgg aactggagtt ggaattgaac   840
aacctcacgg aagaaaacac gaagctgaag gaaattgtgg aggaaaatga aagaaaaga   900
agacaagaga taataagtag aagcaaacaa gtgactaaag agaagagcgg agacaaattg   960
agaaagattc ggaggatggc cagtgccggg tggtaa                             996
```

<210> SEQ ID NO 22
<211> LENGTH: 331
<212> TYPE: PRT
<213> ORGANISM: Arabidopsis thaliana

<400> SEQUENCE: 22

```
Met Ser Val Phe Glu Ser Glu Thr Ser Asn Phe His Val Tyr Asn Asn
 1               5                  10                  15

His Glu Ile Gln Thr Gln Pro Gln Met Gln Thr Phe Leu Ser Glu Glu
            20                  25                  30

Glu Pro Val Gly Arg Gln Asn Ser Ile Leu Ser Leu Thr Leu Asp Glu
        35                  40                  45

Ile Gln Met Lys Ser Gly Lys Ser Phe Gly Ala Met Asn Met Asp Glu
    50                  55                  60

Phe Leu Ala Asn Leu Trp Thr Thr Val Glu Glu Asn Asp Asn Glu Gly
65                  70                  75                  80

Gly Gly Ala His Asn Asp Gly Glu Lys Pro Ala Val Leu Pro Arg Gln
                85                  90                  95

Gly Ser Leu Ser Leu Pro Val Pro Leu Cys Lys Lys Thr Val Asp Glu
            100                 105                 110

Val Trp Leu Glu Ile Gln Asn Gly Val Gln Gln His Pro Pro Ser Ser
        115                 120                 125

Asn Ser Gly Gln Asn Ser Ala Glu Asn Ile Arg Arg Gln Gln Thr Leu
    130                 135                 140

Gly Glu Ile Thr Leu Glu Asp Phe Leu Val Lys Ala Gly Val Val Gln
145                 150                 155                 160

Glu Pro Leu Lys Thr Thr Met Arg Met Ser Ser Ser Asp Phe Gly Tyr
```

165                 170                 175
Asn Pro Glu Phe Gly Val Gly Leu His Cys Gln Asn Gln Asn Asn Tyr
                180                 185                 190

Gly Asp Asn Arg Ser Val Tyr Ser Glu Asn Arg Pro Phe Tyr Ser Val
            195                 200                 205

Leu Gly Glu Ser Ser Ser Cys Met Thr Gly Asn Gly Arg Ser Asn Gln
        210                 215                 220

Tyr Leu Thr Gly Leu Asp Ala Phe Arg Ile Lys Lys Arg Ile Ile Asp
225                 230                 235                 240

Gly Pro Pro Glu Ile Leu Met Glu Arg Gln Arg Arg Met Ile Lys
                245                 250                 255

Asn Arg Glu Ser Ala Ala Arg Ser Arg Ala Arg Arg Gln Ala Tyr Thr
                260                 265                 270

Val Glu Leu Glu Leu Glu Leu Asn Asn Leu Thr Glu Glu Asn Thr Lys
                275                 280                 285

Leu Lys Glu Ile Val Glu Asn Glu Lys Lys Arg Arg Gln Glu Ile
            290                 295                 300

Ile Ser Arg Ser Lys Gln Val Thr Lys Glu Lys Ser Gly Asp Lys Leu
305                 310                 315                 320

Arg Lys Ile Arg Arg Met Ala Ser Ala Gly Trp
                325                 330

<210> SEQ ID NO 23
<211> LENGTH: 789
<212> TYPE: DNA
<213> ORGANISM: Arabidopsis thaliana

<400> SEQUENCE: 23

| | | |
|---|---|---|
| atgggttcta ttagaggaaa cattgaagag cctatatctc agtcattaac gaggcagaac | 60 |
| tctctctata gcttaaagct ccatgaggtt caaacccact taggaagttc tggaaaacca | 120 |
| ctaggaagca tgaaccttga tgagcttctc aagactgtct tgccaccagc tgaggaaggg | 180 |
| cttgttcgtc agggaagctt gacgttacct cgagatctca gtaaaaagac agttgatgag | 240 |
| gtctggagag atatccaaca ggacaagaat ggaaacggta ctagtactac tactactcat | 300 |
| aagcagccta cactcggtga ataacactt gaggatttgt tgttgagagc tggtgtagtg | 360 |
| actgagacag tagtccctca agaaaatgtt gttaacatag cttcaaatgg caatgggtt | 420 |
| gagtatcatc atcagcctca acaacaacaa gggtttatga catatccggt tgcgagatg | 480 |
| caagatatgg tgatgatggg tggattatcg gatacaccac aagcgcctgg gaggaaaaga | 540 |
| gtagctggag agattgtgga agactgtt gagaggagac agaagaggat gatcaagaac | 600 |
| agagaatctg cagcacgttc acgagctagg aacaggctt atacacatga attagagatc | 660 |
| aaggtttcaa ggttagaaga agaaaacgaa aaacttcgga ggctaaagga ggtggagaag | 720 |
| atcctaccaa gtgaaccacc accagatcct aagtggaagc tccggcgaac aaactctgct | 780 |
| tctctctga | 789 |

<210> SEQ ID NO 24
<211> LENGTH: 262
<212> TYPE: PRT
<213> ORGANISM: Arabidopsis thaliana

<400> SEQUENCE: 24

Met Gly Ser Ile Arg Gly Asn Ile Glu Glu Pro Ile Ser Gln Ser Leu
1               5                   10                  15

```
Thr Arg Gln Asn Ser Leu Tyr Ser Leu Lys Leu His Glu Val Gln Thr
             20                  25                  30
His Leu Gly Ser Ser Gly Lys Pro Leu Gly Ser Met Asn Leu Asp Glu
         35                  40                  45
Leu Leu Lys Thr Val Leu Pro Pro Ala Glu Glu Gly Leu Val Arg Gln
     50                  55                  60
Gly Ser Leu Thr Leu Pro Arg Asp Leu Ser Lys Lys Thr Val Asp Glu
65                  70                  75                  80
Val Trp Arg Asp Ile Gln Gln Asp Lys Asn Gly Asn Gly Thr Ser Thr
                 85                  90                  95
Thr Thr Thr His Lys Gln Pro Thr Leu Gly Glu Ile Thr Leu Glu Asp
            100                 105                 110
Leu Leu Leu Arg Ala Gly Val Val Thr Glu Thr Val Val Pro Gln Glu
        115                 120                 125
Asn Val Val Asn Ile Ala Ser Asn Gly Gln Trp Val Glu Tyr His His
    130                 135                 140
Gln Pro Gln Gln Gln Gly Phe Met Thr Tyr Pro Val Cys Glu Met
145                 150                 155                 160
Gln Asp Met Val Met Met Gly Gly Leu Ser Asp Thr Pro Gln Ala Pro
                165                 170                 175
Gly Arg Lys Arg Val Ala Gly Glu Ile Val Glu Lys Thr Val Glu Arg
            180                 185                 190
Arg Gln Lys Arg Met Ile Lys Asn Arg Glu Ser Ala Ala Arg Ser Arg
        195                 200                 205
Ala Arg Lys Gln Ala Tyr Thr His Glu Leu Glu Ile Lys Val Ser Arg
    210                 215                 220
Leu Glu Glu Glu Asn Glu Lys Leu Arg Arg Leu Lys Glu Val Glu Lys
225                 230                 235                 240
Ile Leu Pro Ser Glu Pro Pro Asp Pro Lys Trp Lys Leu Arg Arg
                245                 250                 255
Thr Asn Ser Ala Ser Leu
            260

<210> SEQ ID NO 25
<211> LENGTH: 813
<212> TYPE: DNA
<213> ORGANISM: Arabidopsis thaliana

<400> SEQUENCE: 25
atggcgtcct tcaagttgat gtcttcttcc aattccgact tgtctcgccg taattcttct      60
tctgcttcat cttccccttc tataagatca tcgcaccatc tccgaccaaa tcctcacgcc     120
gatcactcca gaatcagttt cgcttacggc ggaggagtca acgattacac tttcgcgtct     180
gattcaaagc ccttcgagat ggcgattgat gttgatcgga gtatcggaga tcggaacagc     240
gttaacaacg gaaagagtgt tgacgatgtt tggaaagaga ttgtatctgg agagcaaaag     300
acgatcatga tgaaggaaga agaaccagaa gatataatga cacttgagga tttcttagcg     360
aaagcagaaa tggacgaggg agcttcgat  gaaatcgatg tgaagattcc aacggagaga     420
ctcaacaacg acggtagcta tacatttgat tttccgatgc agcgacacag ttcgttccag     480
atggttgaag atcaatggg  tgagggagta acgagaggaa agagagggag agtgatgatg     540
gaggcaatgg ataaagctgc agctcagaga cagaagagga tgatcaagaa ccgtgaatcc     600
gctgctaggt ctcgagagag gaaacaggct tatcaggttg agttagagac tttggctgcc     660
aagttagagg aggagaatga gcagcttttg aaggagattg aagagagcac taaagagaga     720
```

```
tacaagaagc tcatggaggt tctgattccg gtcgatgaga aaccaaggcc accgtcgagg    780
cccttaagca ggagccattc cttggaatgg tga                                813

<210> SEQ ID NO 26
<211> LENGTH: 270
<212> TYPE: PRT
<213> ORGANISM: Arabidopsis thaliana

<400> SEQUENCE: 26

Met Ala Ser Phe Lys Leu Met Ser Ser Asn Ser Asp Leu Ser Arg
1               5                   10                  15

Arg Asn Ser Ser Ser Ala Ser Ser Pro Ser Ile Arg Ser Ser His
                20                  25                  30

His Leu Arg Pro Asn Pro His Ala Asp His Ser Arg Ile Ser Phe Ala
                35                  40                  45

Tyr Gly Gly Gly Val Asn Asp Tyr Thr Phe Ala Ser Asp Ser Lys Pro
        50                  55                  60

Phe Glu Met Ala Ile Asp Val Asp Arg Ser Ile Gly Asp Arg Asn Ser
65              70                  75                  80

Val Asn Asn Gly Lys Ser Val Asp Asp Val Trp Lys Glu Ile Val Ser
                85                  90                  95

Gly Glu Gln Lys Thr Ile Met Met Lys Glu Glu Pro Glu Asp Ile
                100                 105                 110

Met Thr Leu Glu Asp Phe Leu Ala Lys Ala Glu Met Asp Glu Gly Ala
        115                 120                 125

Ser Asp Glu Ile Asp Val Lys Ile Pro Thr Glu Arg Leu Asn Asn Asp
    130                 135                 140

Gly Ser Tyr Thr Phe Asp Phe Pro Met Gln Arg His Ser Ser Phe Gln
145                 150                 155                 160

Met Val Glu Gly Ser Met Gly Gly Gly Val Thr Arg Gly Lys Arg Gly
                165                 170                 175

Arg Val Met Met Glu Ala Met Asp Lys Ala Ala Ala Gln Arg Gln Lys
            180                 185                 190

Arg Met Ile Lys Asn Arg Glu Ser Ala Ala Arg Ser Arg Glu Arg Lys
        195                 200                 205

Gln Ala Tyr Gln Val Glu Leu Glu Thr Leu Ala Ala Lys Leu Glu Glu
    210                 215                 220

Glu Asn Glu Gln Leu Leu Lys Glu Ile Glu Glu Ser Thr Lys Glu Arg
225                 230                 235                 240

Tyr Lys Lys Leu Met Glu Val Leu Ile Pro Val Asp Glu Lys Pro Arg
                245                 250                 255

Pro Pro Ser Arg Pro Leu Ser Arg Ser His Ser Leu Glu Trp
            260                 265                 270

<210> SEQ ID NO 27
<211> LENGTH: 948
<212> TYPE: DNA
<213> ORGANISM: Arabidopsis thaliana

<400> SEQUENCE: 27
atgacgtcgt ttcaggtgat gcgttcttca aattcgagaa actcggatct atctcgtcgc    60
atctcttctg cttctacttc ttcttcgtct ataagacctc aacaacagtt ccggcgagat   120
ctaacaagtg tcggttacgg cggaagaaac gacggattat acagttcaaa ttcgatgacg   180
gtcgaaggga ttttacacga tactttcgca tcagatccac cagcaccaac ggaatcttca   240
```

```
ctcttagatg cgtcgataaa tctgatggat gcttctccag caccaatgga gataacaaca    300
acgacggctt ctgatgttgt ggatcacggc ggaggaacgg agacgacgcg tggtgggaag    360
agtgttgatg agatttggag agagatggta tcaggagaag gtaaagggat gaaggaagag    420
acgtcggaag agataatgac gttagaggat tttctagcga aagctgcggt ggaagacgaa    480
acagcggtga cggcgtcggc ggaggatttg gatgtgaaga ttccggtgac gaattacgga    540
ttcgatcatt ctgcaccgcc gcataatccg tttcagatga ttgataaagt agaaggatca    600
atagttgcgt ttgggaatgg tttagatgtt tacggaggag gagctagagg gaagagagcg    660
agagtgatgg ttgagccatt ggataaagca gctgcacaga gacagagaag gatgattaag    720
aatcgtgaat ctgcagctag gtctagagag aggaaacaag cttatcaagt tgagttagaa    780
gctttggctg cgaagcttga ggaagagaat gagttgcttt ctaaggagat tgaagataag    840
aggaaagaga gataccagaa gttgatggag tttgtgattc ctgttgttga gaaaccgaag    900
cagcagccac cacggttttt acgcaggatt cggtctttgg aatggtga                 948
```

<210> SEQ ID NO 28
<211> LENGTH: 315
<212> TYPE: PRT
<213> ORGANISM: Arabidopsis thaliana

<400> SEQUENCE: 28

```
Met Thr Ser Phe Gln Val Met Arg Ser Ser Asn Ser Arg Asn Ser Asp
1               5                   10                  15

Leu Ser Arg Arg Ile Ser Ser Ala Ser Thr Ser Ser Ser Ser Ile Arg
                20                  25                  30

Pro Gln Gln Gln Phe Arg Arg Asp Leu Thr Ser Val Gly Tyr Gly Gly
            35                  40                  45

Arg Asn Asp Gly Leu Tyr Ser Ser Asn Ser Met Thr Val Glu Gly Ile
        50                  55                  60

Leu His Asp Thr Phe Ala Ser Asp Pro Pro Ala Pro Thr Glu Ser Ser
65                  70                  75                  80

Leu Leu Asp Ala Ser Ile Asn Leu Met Asp Ala Ser Pro Ala Pro Met
                85                  90                  95

Glu Ile Thr Thr Thr Thr Ala Ser Asp Val Val Asp His Gly Gly Gly
            100                 105                 110

Thr Glu Thr Thr Arg Gly Gly Lys Ser Val Asp Glu Ile Trp Arg Glu
        115                 120                 125

Met Val Ser Gly Glu Gly Lys Gly Met Lys Glu Glu Thr Ser Glu Glu
130                 135                 140

Ile Met Thr Leu Glu Asp Phe Leu Ala Lys Ala Val Glu Asp Glu
145                 150                 155                 160

Thr Ala Val Thr Ala Ser Ala Glu Asp Leu Asp Val Lys Ile Pro Val
                165                 170                 175

Thr Asn Tyr Gly Phe Asp His Ser Ala Pro His Asn Pro Phe Gln
            180                 185                 190

Met Ile Asp Lys Val Glu Gly Ser Ile Val Ala Phe Gly Asn Gly Leu
        195                 200                 205

Asp Val Tyr Gly Gly Gly Ala Arg Gly Lys Arg Ala Arg Val Met Val
    210                 215                 220

Glu Pro Leu Asp Lys Ala Ala Ala Gln Arg Gln Arg Arg Met Ile Lys
225                 230                 235                 240

Asn Arg Glu Ser Ala Ala Arg Ser Arg Glu Arg Lys Gln Ala Tyr Gln
```

|  |  | 245 |  |  | 250 |  |  | 255 |  |  |  |
|---|---|---|---|---|---|---|---|---|---|---|---|

Val Glu Leu Glu Ala Leu Ala Ala Lys Leu Glu Glu Asn Glu Leu
            260                 265                 270

Leu Ser Lys Glu Ile Glu Asp Lys Arg Lys Glu Arg Tyr Gln Lys Leu
        275                 280                 285

Met Glu Phe Val Ile Pro Val Val Glu Lys Pro Lys Gln Gln Pro Pro
    290                 295                 300

Arg Phe Leu Arg Arg Ile Arg Ser Leu Glu Trp
305                 310                 315

<210> SEQ ID NO 29
<211> LENGTH: 2163
<212> TYPE: DNA
<213> ORGANISM: Arabidopsis thaliana

<400> SEQUENCE: 29

| atgaaaagct | tgcatgtggc | ggccaacgcc | ggagatctgg | ctgaggattg | tggaatactc | 60 |
| ggtggagacg | ctgatgatac | tgttttgatg | gatggaattg | atgaagttgg | tagagagatc | 120 |
| tggttagatg | accatggagg | agataataat | catgttcatg | gtcatcaaga | tgatgatttg | 180 |
| attgttcatc | atgacccttc | aatcttctat | ggagatctcc | caacgcttcc | tgatttccca | 240 |
| tgcatgtcgt | cttcatcatc | gtcttcaaca | tctccagctc | ctgtcaacgc | aatcgtctcc | 300 |
| tcagcctctt | cttcttcggc | agcttcttcc | tccacttcct | cagctgcttc | ttgggctata | 360 |
| ttgagatcag | atggagaaga | tccgactcca | aaccaaaacc | aatacgcatc | aggaaactgt | 420 |
| gacgactctt | ctggtgcatt | gcaatccaca | gcttccatgg | agattccatt | agacagcagt | 480 |
| caaggttttg | gttgcggcga | aggcggtggt | gattgcattg | atatgatgga | gactttcggg | 540 |
| tacatggatc | tacttgatag | caacgagttc | tttgacacct | cagctatatt | tagccaagac | 600 |
| gacgacacgc | aaaaccctaa | cttgatggac | caaaccctag | agagacaaga | agaccaggtc | 660 |
| gttgttccga | tgatggagaa | taacagtggt | ggagacatgc | aaatgatgaa | ttcttccttg | 720 |
| gaacaggacg | atgatctcgc | tgctgtgttt | tggagtggc | taagaacaa | caaggagact | 780 |
| gtgtcggctg | aggatttgag | gaaagtaaag | ataaagaaag | ctacgattga | atcagcggca | 840 |
| agaagactag | gcggtggtaa | agaagcgatg | aagcagcttt | taaagctgat | tcttgaatgg | 900 |
| gtccaaacta | atcacttaca | agaagacgc | accaccacca | ccaccaccaa | cctctcttat | 960 |
| caacaatcat | tccaacaaga | tccatttcaa | accctaacc | taataacaa | caacctaatc | 1020 |
| ccaccgtccg | accaaacctg | tttctcacct | tcaacatggg | ttcctccacc | accacaacaa | 1080 |
| caagcttttg | tctcggaccc | gggttttgga | tacatgcctg | ctccaaacta | tccgccacag | 1140 |
| ccagagttcc | ttcctttact | tgaatctcca | ccgtcatggc | caccaccacc | acagtctggt | 1200 |
| cccatgccac | atcaacaatt | ccccatgccg | ccaacctcgc | agtataatca | atttggagat | 1260 |
| ccaacaggtt | tcaatggata | caacatgaat | ccgtaccaat | atccttatgt | tcctgcagga | 1320 |
| caaatgagag | atcagagatt | actccgtttg | tgttcctcag | caactaaaga | ggcaagaaag | 1380 |
| aaacggatgg | cgagacagag | gaggttcttg | tctcatcacc | acagacataa | caacaacaac | 1440 |
| aacaacaaca | acaataatca | gcagaaccaa | acccaaatcg | agaaacctg | tgccgcggtg | 1500 |
| gctccacaac | ttaaccccgt | ggccacaacc | gccacgggag | ggacctggat | gtattggcct | 1560 |
| aatgtcccgg | cagtgccgcc | tcaattaccg | ccagtgatgg | agactcagtt | acctaccatg | 1620 |
| gaccgagctg | gctcagcttc | tgctatgcca | cgtcagcagg | tggtaccaga | tcgccggcag | 1680 |
| ggatggaaac | cagaaaagaa | tttgcggttt | ctcttgcaga | aagtcttgaa | gcaaagcgac | 1740 |

```
gtgggtaacc tcggaaggat cgttttgcca aaaaaagaag ctgagacaca cttgccggag      1800
ctagaggcaa gagacggcat ctctctggcc atggaagaca tcggaacctc tcgtgtttgg      1860
aacatgcgct acaggttttg gcctaacaac aaaagcagga tgtatctcct cgagaacacc      1920
ggcgattttg tgaaaaccaa tgggctccaa gaaggtgatt tcatagtcat atactccgac      1980
gtcaaatgtg gcaaatattt gatacgaggg gttaaagtaa gacaaccgag cggacaaaag      2040
ccggaggccc caccgtcgtc agcagctacg aagagacaaa acaagtcgca aaggaacata      2100
aacaataact ctccgtcggc gaatgtggtg gtcgcttcac caacttctca aactgttaaa      2160
tga                                                                   2163

<210> SEQ ID NO 30
<211> LENGTH: 720
<212> TYPE: PRT
<213> ORGANISM: Arabidopsis thaliana

<400> SEQUENCE: 30

Met Lys Ser Leu His Val Ala Ala Asn Ala Gly Asp Leu Ala Glu Asp
1               5                   10                  15

Cys Gly Ile Leu Gly Gly Asp Ala Asp Thr Val Leu Met Asp Gly
                20                  25                  30

Ile Asp Glu Val Gly Arg Glu Ile Trp Leu Asp His Gly Gly Asp
            35                  40                  45

Asn Asn His Val His Gly His Gln Asp Asp Leu Ile Val His His
        50                  55                  60

Asp Pro Ser Ile Phe Tyr Gly Asp Leu Pro Thr Leu Pro Asp Phe Pro
65                  70                  75                  80

Cys Met Ser Ser Ser Ser Ser Ser Thr Ser Pro Ala Pro Val Asn
                85                  90                  95

Ala Ile Val Ser Ser Ala Ser Ser Ser Ala Ala Ser Ser Ser Thr
            100                 105                 110

Ser Ser Ala Ala Ser Trp Ala Ile Leu Arg Ser Asp Gly Glu Asp Pro
        115                 120                 125

Thr Pro Asn Gln Asn Gln Tyr Ala Ser Gly Asn Cys Asp Asp Ser Ser
    130                 135                 140

Gly Ala Leu Gln Ser Thr Ala Ser Met Glu Ile Pro Leu Asp Ser Ser
145                 150                 155                 160

Gln Gly Phe Gly Cys Gly Glu Gly Gly Asp Cys Ile Asp Met Met
                165                 170                 175

Glu Thr Phe Gly Tyr Met Asp Leu Leu Asp Ser Asn Glu Phe Phe Asp
            180                 185                 190

Thr Ser Ala Ile Phe Ser Gln Asp Asp Asp Thr Gln Asn Pro Asn Leu
        195                 200                 205

Met Asp Gln Thr Leu Glu Arg Gln Glu Asp Gln Val Val Pro Met
    210                 215                 220

Met Glu Asn Asn Ser Gly Gly Asp Met Gln Met Met Asn Ser Ser Leu
225                 230                 235                 240

Glu Gln Asp Asp Asp Leu Ala Ala Val Phe Leu Glu Trp Leu Lys Asn
                245                 250                 255

Asn Lys Glu Thr Val Ser Ala Glu Asp Leu Arg Lys Val Lys Ile Lys
            260                 265                 270

Lys Ala Thr Ile Glu Ser Ala Ala Arg Arg Leu Gly Gly Gly Lys Glu
        275                 280                 285
```

-continued

```
Ala Met Lys Gln Leu Leu Lys Leu Ile Leu Glu Trp Val Gln Thr Asn
    290                 295                 300

His Leu Gln Arg Arg Arg Thr Thr Thr Thr Thr Asn Leu Ser Tyr
305                 310                 315                 320

Gln Gln Ser Phe Gln Gln Asp Pro Phe Gln Asn Pro Asn Pro Asn Asn
                325                 330                 335

Asn Asn Leu Ile Pro Pro Ser Asp Gln Thr Cys Phe Ser Pro Ser Thr
            340                 345                 350

Trp Val Pro Pro Pro Gln Gln Gln Ala Phe Val Ser Asp Pro Gly
            355                 360                 365

Phe Gly Tyr Met Pro Ala Pro Asn Tyr Pro Pro Gln Pro Glu Phe Leu
    370                 375                 380

Pro Leu Leu Glu Ser Pro Pro Ser Trp Pro Pro Pro Gln Ser Gly
385                 390                 395                 400

Pro Met Pro His Gln Gln Phe Pro Met Pro Pro Thr Ser Gln Tyr Asn
                405                 410                 415

Gln Phe Gly Asp Pro Thr Gly Phe Asn Gly Tyr Asn Met Asn Pro Tyr
            420                 425                 430

Gln Tyr Pro Tyr Val Pro Ala Gly Gln Met Arg Asp Gln Arg Leu Leu
        435                 440                 445

Arg Leu Cys Ser Ser Ala Thr Lys Glu Ala Arg Lys Lys Arg Met Ala
450                 455                 460

Arg Gln Arg Arg Phe Leu Ser His His Arg His Asn Asn Asn
465                 470                 475                 480

Asn Asn Asn Asn Asn Asn Gln Gln Asn Gln Thr Gln Ile Gly Glu Thr
                485                 490                 495

Cys Ala Ala Val Ala Pro Gln Leu Asn Pro Val Ala Thr Thr Ala Thr
            500                 505                 510

Gly Gly Thr Trp Met Tyr Trp Pro Asn Val Pro Ala Val Pro Pro Gln
        515                 520                 525

Leu Pro Pro Val Met Glu Thr Gln Leu Pro Thr Met Asp Arg Ala Gly
530                 535                 540

Ser Ala Ser Ala Met Pro Arg Gln Gln Val Val Pro Asp Arg Arg Gln
545                 550                 555                 560

Gly Trp Lys Pro Glu Lys Asn Leu Arg Phe Leu Leu Gln Lys Val Leu
                565                 570                 575

Lys Gln Ser Asp Val Gly Asn Leu Gly Arg Ile Val Leu Pro Lys Lys
            580                 585                 590

Glu Ala Glu Thr His Leu Pro Glu Leu Glu Ala Arg Asp Gly Ile Ser
        595                 600                 605

Leu Ala Met Glu Asp Ile Gly Thr Ser Arg Val Trp Asn Met Arg Tyr
    610                 615                 620

Arg Phe Trp Pro Asn Asn Lys Ser Arg Met Tyr Leu Leu Glu Asn Thr
625                 630                 635                 640

Gly Asp Phe Val Lys Thr Asn Gly Leu Gln Glu Gly Asp Phe Ile Val
                645                 650                 655

Ile Tyr Ser Asp Val Lys Cys Gly Lys Tyr Leu Ile Arg Gly Val Lys
            660                 665                 670

Val Arg Gln Pro Ser Gly Gln Lys Pro Glu Ala Pro Ser Ser Ala
        675                 680                 685

Ala Thr Lys Arg Gln Asn Lys Ser Gln Arg Asn Ile Asn Asn Asn Ser
    690                 695                 700

Pro Ser Ala Asn Val Val Val Ala Ser Pro Thr Ser Gln Thr Val Lys
```

<210> SEQ ID NO 31
<211> LENGTH: 942
<212> TYPE: DNA
<213> ORGANISM: Arabidopsis thaliana

<400> SEQUENCE: 31

```
atgatggttg atgaaaatgt ggaaaccaag gcctctactt tagtggcaag tgttgatcat      60
gggtttggat ccgggtcggg tcatgatcat catgggttat cggcgtctgt gcctcttctt     120
ggtgttaact ggaagaagag aaggatgcct agacagagac gatcttcttc ttcctttaac     180
cttctctctt tccctcctcc tatgcctcct atttcccacg tgccaactcc tctccccgca     240
cgtaaaattg acccaagaaa gctaagattc ctcttccaaa aggaactcaa gaacagtgac     300
gtcagctctc tccgacgtat gatactcccg aagaaagccg cggaggctca cttgccggca     360
cttgaatgca aggaagggat tcctataaga atggaagatt tggacggttt tcacgtttgg     420
accttcaagt ataggtactg gccaaacaac aatagcagaa tgtacgtgct agaaaacaca     480
ggcgattttg tgaatgctca tggtctgcag ctaggtgact tcatcatggt ttaccaagat     540
ctctactcaa acaattacgt tatacaagca agaaaagcat cggaagaaga agaagtagac     600
gtaatcaatc ttgaagaaga cgacgtttac acaaacttaa caaggatcga aaacactgtg     660
gttaacgatc ttctcctcca agattttaat catcacaaca acaacaacaa caacaacagc     720
aacagcaaca gcaacaaatg ttcttactat tatccagtca tagatgatgt caccacaaac     780
acagagtctt ttgtctacga cacgacggct cttacctcca acgatactcc tctcgatttt     840
ttgggtggac atacgacgac tactaataat tattactcca agttcggaac attcgatggt     900
ttgggctccg ttgagaatat ctctctcgat gacttctact ag                       942
```

<210> SEQ ID NO 32
<211> LENGTH: 313
<212> TYPE: PRT
<213> ORGANISM: Arabidopsis thaliana

<400> SEQUENCE: 32

```
Met Met Val Asp Glu Asn Val Glu Thr Lys Ala Ser Thr Leu Val Ala
  1               5                  10                  15

Ser Val Asp His Gly Phe Gly Ser Gly Ser Gly His Asp His His Gly
                 20                  25                  30

Leu Ser Ala Ser Val Pro Leu Leu Gly Val Asn Trp Lys Lys Arg Arg
             35                  40                  45

Met Pro Arg Gln Arg Arg Ser Ser Ser Phe Asn Leu Leu Ser Phe
         50                  55                  60

Pro Pro Pro Met Pro Pro Ile Ser His Val Pro Thr Pro Leu Pro Ala
 65                  70                  75                  80

Arg Lys Ile Asp Pro Arg Lys Leu Arg Phe Leu Gln Lys Glu Leu
                 85                  90                  95

Lys Asn Ser Asp Val Ser Ser Leu Arg Arg Met Ile Leu Pro Lys Lys
                100                 105                 110

Ala Ala Glu Ala His Leu Pro Ala Leu Glu Cys Lys Glu Gly Ile Pro
            115                 120                 125

Ile Arg Met Glu Asp Leu Asp Gly Phe His Val Trp Thr Phe Lys Tyr
        130                 135                 140

Arg Tyr Trp Pro Asn Asn Asn Ser Arg Met Tyr Val Leu Glu Asn Thr
145                 150                 155                 160
```

Gly Asp Phe Val Asn Ala His Gly Leu Gln Leu Gly Asp Phe Ile Met
            165                 170                 175

Val Tyr Gln Asp Leu Tyr Ser Asn Asn Tyr Val Ile Gln Ala Arg Lys
        180                 185                 190

Ala Ser Glu Glu Glu Val Asp Val Ile Asn Leu Glu Glu Asp Asp
    195                 200                 205

Val Tyr Thr Asn Leu Thr Arg Ile Glu Asn Thr Val Val Asn Asp Leu
        210                 215                 220

Leu Leu Gln Asp Phe Asn His His Asn Asn Asn Asn Asn Asn Asn Ser
225                 230                 235                 240

Asn Ser Asn Ser Asn Lys Cys Ser Tyr Tyr Tyr Pro Val Ile Asp Asp
            245                 250                 255

Val Thr Thr Asn Thr Glu Ser Phe Val Tyr Asp Thr Thr Ala Leu Thr
                260                 265                 270

Ser Asn Asp Thr Pro Leu Asp Phe Leu Gly Gly His Thr Thr Thr Thr
            275                 280                 285

Asn Asn Tyr Tyr Ser Lys Phe Gly Thr Phe Asp Gly Leu Gly Ser Val
        290                 295                 300

Glu Asn Ile Ser Leu Asp Asp Phe Tyr
305                 310

<210> SEQ ID NO 33
<211> LENGTH: 1092
<212> TYPE: DNA
<213> ORGANISM: Arabidopsis thaliana

<400> SEQUENCE: 33

```
atggataact tcttacccct tccctcttct aacgcaaact ctgtccaaga actctctatg      60
gatcctaaca caatcgctc gcacttcaca acagtcccta cttatgatca tcatcaggct     120
cagcctcatc acttcttgcc tccgttttca tacccggtgg agcagatggc ggcggtgatg     180
aatcctcagc cggtttactt atcggagtgt tatcctcaga tcccggttac gcaaaccgga     240
agtgaattcg gttctctggt tggtaatcct tgtttgtggc aagagagagg tggttttctt     300
gatccgcgta tgacgaagat ggcaaggatc aacaggaaaa acgccatgat gagatcaaga     360
aacaactcta gccctaattc tagtccaagt gagttggttg attcaaagag acagctgatg     420
atgcttaact tgaaaaataa cgtgcagatc tccgacaaga agatagcta ccaacagtcc      480
acatttgata caagaagct tagggttttg tgtgagaagg aattgaagaa cagcgatgtt      540
gggtcactcg ggaggatagt tctaccaaag agagatgcag aagcaaatct tccgaagcta     600
tctgataaag aaggaatcgt tgtacagatg agagatgttt tctctatgca gtcttggtct     660
ttcaaataca gttttggtc caataacaag agcagaatgt atgtcctcga gaacacagga     720
gaatttgtga gcaaaatgg agctgagata ggagactttt taacaatata cgaggacgaa     780
agcaagaatc tctacttcgc catgaatgga aattcgggaa acaaaatga aggaagagaa     840
aatgagtcga gggaaaggaa ccactacgaa gaggcaatgc ttgattacat accaagagac     900
gaagaggaag cttccattgc aatgctcatc ggaaatctaa acgatcacta tcccatccct     960
aacgatctca tggacctcac cactgacctt cagcaccatc aagccacgtc ctcatcaatg    1020
ccacctgagg atcacgcgta cgtgggttca tccgatgatc aggtgagctt taacgacttt    1080
gagtggtggt ga                                                        1092
```

<210> SEQ ID NO 34

<211> LENGTH: 363
<212> TYPE: PRT
<213> ORGANISM: Arabidopsis thaliana

<400> SEQUENCE: 34

```
Met Asp Asn Phe Leu Pro Phe Pro Ser Ser Asn Ala Asn Ser Val Gln
1               5                   10                  15

Glu Leu Ser Met Asp Pro Asn Asn Arg Ser His Phe Thr Thr Val
            20                  25                  30

Pro Thr Tyr Asp His His Gln Ala Gln Pro His His Phe Leu Pro Pro
                35                  40                  45

Phe Ser Tyr Pro Val Glu Gln Met Ala Ala Val Met Asn Pro Gln Pro
    50                  55                  60

Val Tyr Leu Ser Glu Cys Tyr Pro Gln Ile Pro Val Thr Gln Thr Gly
65                  70                  75                  80

Ser Glu Phe Gly Ser Leu Val Gly Asn Pro Cys Leu Trp Gln Glu Arg
                85                  90                  95

Gly Gly Phe Leu Asp Pro Arg Met Thr Lys Met Ala Arg Ile Asn Arg
            100                 105                 110

Lys Asn Ala Met Met Arg Ser Arg Asn Asn Ser Ser Pro Asn Ser Ser
        115                 120                 125

Pro Ser Glu Leu Val Asp Ser Lys Arg Gln Leu Met Met Leu Asn Leu
130                 135                 140

Lys Asn Asn Val Gln Ile Ser Asp Lys Lys Asp Ser Tyr Gln Gln Ser
145                 150                 155                 160

Thr Phe Asp Asn Lys Lys Leu Arg Val Leu Cys Glu Lys Glu Leu Lys
                165                 170                 175

Asn Ser Asp Val Gly Ser Leu Gly Arg Ile Val Leu Pro Lys Arg Asp
            180                 185                 190

Ala Glu Ala Asn Leu Pro Lys Leu Ser Asp Lys Glu Gly Ile Val Val
        195                 200                 205

Gln Met Arg Asp Val Phe Ser Met Gln Ser Trp Ser Phe Lys Tyr Lys
210                 215                 220

Phe Trp Ser Asn Asn Lys Ser Arg Met Tyr Val Leu Glu Asn Thr Gly
225                 230                 235                 240

Glu Phe Val Lys Gln Asn Gly Ala Glu Ile Gly Asp Phe Leu Thr Ile
                245                 250                 255

Tyr Glu Asp Glu Ser Lys Asn Leu Tyr Phe Ala Met Asn Gly Asn Ser
            260                 265                 270

Gly Lys Gln Asn Glu Gly Arg Glu Asn Glu Ser Arg Glu Arg Asn His
        275                 280                 285

Tyr Glu Glu Ala Met Leu Asp Tyr Ile Pro Arg Asp Glu Glu Glu Ala
290                 295                 300

Ser Ile Ala Met Leu Ile Gly Asn Leu Asn Asp His Tyr Pro Ile Pro
305                 310                 315                 320

Asn Asp Leu Met Asp Leu Thr Thr Asp Leu Gln His Gln Ala Thr
                325                 330                 335

Ser Ser Ser Met Pro Pro Glu Asp His Ala Tyr Val Gly Ser Ser Asp
            340                 345                 350

Asp Gln Val Ser Phe Asn Asp Phe Glu Trp Trp
        355                 360
```

<210> SEQ ID NO 35
<211> LENGTH: 1035
<212> TYPE: DNA

<213> ORGANISM: Arabidopsis thaliana

<400> SEQUENCE: 35

```
atggaatcga gtagcgttga tgagagtact acaagtacag gttccatctg tgaaaccccg    60
gcgataactc cggcgaaaaa gtcgtcggta ggtaacttat acaggatggg aagcggatca   120
agcgttgtgt tagattcaga gaacggcgta gaagctgaat ctaggaagct tccgtcgtca   180
aaatacaaag gtgtggtgcc acaaccaaac ggaagatggg gagctcagat ttacgagaaa   240
caccagcgcg tgtggctcgg gacattcaac gaagaagacg aagccgctcg tgcctacgac   300
gtcgcggttc acaggttccg tcgccgtgac gccgtcacaa atttcaaaga cgtgaagatg   360
gacgaagacg aggtcgattt cttgaattct cattcgaaat ctgagatcgt tgatatgttg   420
aggaaacata cttataacga agagttagag cagagtaaac ggcgtcgtaa tggtaacgga   480
aacatgacta ggacgttgtt aacgtcgggg ttgagtaatg atggtgtttc tacgacgggg   540
tttagatcgg cggaggcact gtttgagaaa gcggtaacgc caagcgacgt tgggaagcta   600
aaccgtttgg ttataccgaa acatcacgca gagaaacatt ttccgttacc gtcaagtaac   660
gtttccgtga aaggagtgtt gttgaacttt gaggacgtta acgggaaagt gtggaggttc   720
cgttactcgt attggaacag tagtcagagt tatgttttga ctaaaggttg gagcaggttc   780
gttaaggaga gaatctacg tgctggtgac gtggttagtt tcagtagatc taacggtcag   840
gatcaacagt tgtacattgg gtggaagtcg agatccgggt cagatttaga tgcgggtcgg   900
gttttgagat tgttcggagt taacatttca ccggagagtt caagaaacga cgtcgtagga   960
aacaaaagag tgaacgatac tgagatgtta tcgttggtgt gtagcaagaa gcaacgcatc  1020
tttcacgcct cgtaa                                                   1035
```

<210> SEQ ID NO 36
<211> LENGTH: 344
<212> TYPE: PRT
<213> ORGANISM: Arabidopsis thaliana

<400> SEQUENCE: 36

```
Met Glu Ser Ser Ser Val Asp Glu Ser Thr Thr Ser Thr Gly Ser Ile
1               5                   10                  15

Cys Glu Thr Pro Ala Ile Thr Pro Ala Lys Lys Ser Ser Val Gly Asn
            20                  25                  30

Leu Tyr Arg Met Gly Ser Gly Ser Val Val Leu Asp Ser Glu Asn
        35                  40                  45

Gly Val Glu Ala Glu Ser Arg Lys Leu Pro Ser Ser Lys Tyr Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Val His Arg Phe Arg Arg Arg Asp Ala Val
            100                 105                 110

Thr Asn Phe Lys Asp Val Lys Met Asp Glu Asp Glu Val Asp Phe Leu
        115                 120                 125

Asn Ser His Ser Lys Ser Glu Ile Val Asp Met Leu Arg Lys His Thr
    130                 135                 140

Tyr Asn Glu Glu Leu Glu Gln Ser Lys Arg Arg Arg Asn Gly Asn Gly
145                 150                 155                 160

Asn Met Thr Arg Thr Leu Leu Thr Ser Gly Leu Ser Asn Asp Gly Val
```

```
                165                 170                 175
Ser Thr Thr Gly Phe Arg Ser Ala Glu Ala Leu Phe Glu Lys Ala Val
            180                 185                 190

Thr Pro Ser Asp Val Gly Lys Leu Asn Arg Leu Val Ile Pro Lys His
        195                 200                 205

His Ala Glu Lys His Phe Pro Leu Pro Ser Ser Asn Val Ser Val Lys
    210                 215                 220

Gly Val Leu Leu Asn Phe Glu Asp Val Asn Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Val Val
            260                 265                 270

Ser Phe Ser Arg Ser Asn Gly Gln Asp Gln Leu Tyr Ile Gly Trp
        275                 280                 285

Lys Ser Arg Ser Gly Ser Asp Leu Asp Ala Gly Arg Val Leu Arg Leu
    290                 295                 300

Phe Gly Val Asn Ile Ser Pro Glu Ser Ser Arg Asn Asp Val Val Gly
305                 310                 315                 320

Asn Lys Arg Val Asn Asp Thr Glu Met Leu Ser Leu Val Cys Ser Lys
                325                 330                 335

Lys Gln Arg Ile Phe His Ala Ser
            340
```

<210> SEQ ID NO 37
<211> LENGTH: 1002
<212> TYPE: DNA
<213> ORGANISM: Arabidopsis thaliana

<400> SEQUENCE: 37

```
atggatgcca tgagtagcgt agacgagagc tctacaacta cagattccat tccggcgaga     60
aagtcatcgt ctccggcgag tttactatat agaatgggaa gcggaacaag cgtggtactt    120
gattcagaga cggtgtcga agtcgaagtc gaagccgaat caagaaagct tccttcttca    180
agattcaaag gtgttgttcc tcaaccaaat ggaagatggg gagctcagat ttacgagaaa    240
catcaacgcg tgtggcttgg tactttcaac gaggaagacg aagcagctcg tgcttacgac    300
gtcgcggctc accgtttccg tggccgcgat gccgttacta atttcaaaga cacgacgttc    360
gaagaagagg ttgagttctt aaacgcgcat tcgaaatcag agatcgtaga tatgttgaga    420
aaacacactt acaaagaaga gttagaccaa aggaaacgta accgtgacgg taacggaaaa    480
gagacgacgg cgtttgcttt ggcttcgatg gtggttatga cggggtttaa acgcggag     540
ttactgtttg agaaaacggt aacgccaagt gacgtcggga actaaaccg tttagttata    600
ccaaaacacc aagcggagaa acattttccg ttaccgttag gtaataataa cgtctccgtt    660
aaaggtatgc tgttgaattt cgaagacgtt aacgggaaag tgtggaggtt ccgttactct    720
tattggaata gtagtcaaag ttatgtgttg accaaaggtt ggagtagatt cgttaaagag    780
aagagacttt gtgctggtga tttgatcagt tttaaagat ccaacgatca agatcaaaaa    840
ttctttatcg gtggaaatc gaatccggg ttggatctag agacgggtcg ggttatgaga    900
ttgtttgggg ttgatatttc tttaaacgcc gtcgttgtag tgaaggaaac aacggaggtg    960
ttaatgtcgt cgttaaggtg taagaagcaa cgagttttgt aa                      1002
```

<210> SEQ ID NO 38

<211> LENGTH: 333
<212> TYPE: PRT
<213> ORGANISM: Arabidopsis thaliana

<400> SEQUENCE: 38

```
Met Asp Ala Met Ser Ser Val Asp Glu Ser Thr Thr Thr Asp Ser
1               5                   10                  15

Ile Pro Ala Arg Lys Ser Ser Pro Ala Ser Leu Leu Tyr Arg Met
            20                  25                  30

Gly Ser Gly Thr Ser Val Val Leu Asp Ser Glu Asn Gly Val Glu Val
                35                  40                  45

Glu Val Glu Ala Glu Ser Arg Lys Leu Pro Ser Ser Arg Phe Lys Gly
    50                  55                  60

Val Val Pro Gln Pro Asn Gly Arg Trp Gly Ala Gln Ile Tyr Glu Lys
65              70                  75                  80

His Gln Arg Val Trp Leu Gly Thr Phe Asn Glu Glu Asp Glu Ala Ala
                85                  90                  95

Arg Ala Tyr Asp Val Ala Ala His Arg Phe Arg Gly Arg Asp Ala Val
            100                 105                 110

Thr Asn Phe Lys Asp Thr Thr Phe Glu Glu Val Glu Phe Leu Asn
            115                 120                 125

Ala His Ser Lys Ser Glu Ile Val Asp Met Leu Arg Lys His Thr Tyr
    130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                165                 170                 175

Lys Thr Ala Glu Leu Leu Phe Glu Lys Thr Val Thr Pro Ser Asp Val
            180                 185                 190

Gly Lys Leu Asn Arg Leu Val Ile Pro Lys His Gln Ala Glu Lys His
        195                 200                 205

Phe Pro Leu Pro Leu Gly Asn Asn Val Ser Val Lys Gly Met Leu
210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
            245                 250                 255

Phe Val Lys Glu Lys Arg Leu Cys Ala Gly Asp Leu Ile Ser Phe Lys
            260                 265                 270

Arg Ser Asn Asp Gln Asp Gln Lys Phe Phe Ile Gly Trp Lys Ser Lys
        275                 280                 285

Ser Gly Leu Asp Leu Glu Thr Gly Arg Val Met Arg Leu Phe Gly Val
    290                 295                 300

Asp Ile Ser Leu Asn Ala Val Val Val Val Lys Glu Thr Thr Glu Val
305                 310                 315                 320

Leu Met Ser Ser Leu Arg Cys Lys Lys Gln Arg Val Leu
                325                 330
```

<210> SEQ ID NO 39
<211> LENGTH: 1086
<212> TYPE: DNA
<213> ORGANISM: Arabidopsis thaliana

<400> SEQUENCE: 39
atggaataca gctgtgtaga cgacagtagt acaacgtcag aatctctctc catctctact    60

```
actccaaagc cgacaacgac gacggagaag aaactctctt ctccgccggc gacgtcgatg    120
cgtctctaca gaatgggaag cggcggaagc agcgtcgttg tggattcaga gaacggcgtc    180
gagaccgagt cacgtaagct tccttcgtcg aaatataaag gcgttgtgcc tcagcctaac    240
ggaagatggg gagctcagat ttacgagaag catcagcgag tttggctcgg tactttcaac    300
gaggaagaag aagctgcgtc ttcttacgac atcgccgtga ggagattccg cggccgcgac    360
gccgtcacta acttcaaatc tcaagttgat ggaaacgacg ccgaatcggc ttttcttgac    420
gctcattcta aagctgagat cgtggatatg ttgaggaaac acacttacgc cgatgagttt    480
gagcagagta cacggaagtt tgttaacggc gacggaaaac gctctgggtt ggagacggcg    540
acgtacggaa acgacgctgt tttgagagcg cgtgaggttt tgttcgagaa gactgttacg    600
ccgagcgacg tcgggaagct gaaccgttta gtgataccga acaacacgc ggagaagcat    660 tttccgttac cggcgatgac gacggcgatg gggatgaatc cgtctccgac gaaaggcgtt    720
ttgattaact tggaagatag aacagggaaa gtgtggcggt tccgttacag ttactggaac    780
agcagtcaaa gttacgtgtt gaccaagggc tggagccggt tcgttaaaga aagaatctt    840 cgagccggtg atgtggtttg tttcgagaga tcaaccggac cagaccggca attgtatatc    900
cactggaaag tccggtctag tccggttcag actgtggtta ggctattcgg agtcaacatt    960
ttcaatgtga gtaacgagaa accaaacgac gtcgcagtag agtgtgttgg caagaagaga   1020
tctcgggaag atgatttgtt ttcgttaggg tgttccaaga agcaggcgat tatcaacatc   1080
ttgtga                                                              1086
```

<210> SEQ ID NO 40
<211> LENGTH: 361
<212> TYPE: PRT
<213> ORGANISM: Arabidopsis thaliana

<400> SEQUENCE: 40

```
Met Glu Tyr Ser Cys Val Asp Asp Ser Ser Thr Thr Ser Glu Ser Leu
1               5                   10                  15

Ser Ile Ser Thr Thr Pro Lys Pro Thr Thr Thr Thr Glu Lys Lys Leu
            20                  25                  30

Ser Ser Pro Pro Ala Thr Ser Met Arg Leu Tyr Arg Met Gly Ser Gly
        35                  40                  45

Gly Ser Ser Val Val Leu Asp Ser Glu Asn Gly Val Glu Thr Glu Ser
    50                  55                  60

Arg Lys Leu Pro Ser Ser Lys Tyr Lys Gly Val Pro Gln Pro Asn
65                  70                  75                  80

Gly Arg Trp Gly Ala Gln Ile Tyr Glu Lys His Gln Arg Val Trp Leu
                85                  90                  95

Gly Thr Phe Asn Glu Glu Glu Glu Ala Ala Ser Ser Tyr Asp Ile Ala
            100                 105                 110

Val Arg Arg Phe Arg Gly Arg Asp Ala Val Thr Asn Phe Lys Ser Gln
        115                 120                 125

Val Asp Gly Asn Asp Ala Glu Ser Ala Phe Leu Asp Ala His Ser Lys
    130                 135                 140

Ala Glu Ile Val Asp Met Leu Arg Lys His Thr Tyr Ala Asp Glu Phe
145                 150                 155                 160

Glu Gln Ser Arg Arg Lys Phe Val Asn Gly Asp Gly Lys Arg Ser Gly
                165                 170                 175

Leu Glu Thr Ala Thr Tyr Gly Asn Asp Ala Val Leu Arg Ala Arg Glu
            180                 185                 190
```

```
Val Leu Phe Glu Lys Thr Val Thr Pro Ser Asp Val Gly Lys Leu Asn
        195                 200                 205

Arg Leu Val Ile Pro Lys Gln His Ala Glu Lys His Phe Pro Leu Pro
        210                 215                 220

Ala Met Thr Thr Ala Met Gly Met Asn Pro Ser Pro Thr Lys Gly Val
225                 230                 235                 240

Leu Ile Asn Leu Glu Asp Arg Thr Gly Lys Val Trp Arg Phe Arg Tyr
                245                 250                 255

Ser Tyr Trp Asn Ser Ser Gln Ser Tyr Val Leu Thr Lys Gly Trp Ser
                260                 265                 270

Arg Phe Val Lys Glu Lys Asn Leu Arg Ala Gly Asp Val Val Cys Phe
            275                 280                 285

Glu Arg Ser Thr Gly Pro Asp Arg Gln Leu Tyr Ile His Trp Lys Val
        290                 295                 300

Arg Ser Ser Pro Val Gln Thr Val Val Arg Leu Phe Gly Val Asn Ile
305                 310                 315                 320

Phe Asn Val Ser Asn Glu Lys Pro Asn Asp Val Ala Val Glu Cys Val
                325                 330                 335

Gly Lys Lys Arg Ser Arg Glu Asp Asp Leu Phe Ser Leu Gly Cys Ser
                340                 345                 350

Lys Lys Gln Ala Ile Ile Asn Ile Leu
            355                 360

<210> SEQ ID NO 41
<211> LENGTH: 2373
<212> TYPE: DNA
<213> ORGANISM: Arabidopsis thaliana

<400> SEQUENCE: 41
atgtttgaag tcaaaatggg gtcaaagatg tgcatgaacg cttcatgtgg tacgacttct      60
actgttgaat ggaagaaagg ttggcctctt cgatctggtc ttctcgctga tctctgttat     120
cgttgcggat ctgcgtatga gagttctcta ttctgtgaac aatttcataa ggaccaatct     180
ggttggaggg aatgctattt gtgtagcaag agactacatt gtggatgcat tgcttctaag     240
gtaacgattg agttaatgga ctatggtggt gttggttgta gtacatgtgc ttgctgccat     300
caactcaatt tgaacacaag gggtgagaat ccaggtgttt ttagcagatt gccaatgaaa     360
acgttagctg ataggcaaca tgtaaatggc gaaagcggag gaagaaacga aggcgatctc     420
ttttctcagc cactagtcat gggcggagat aaaagggaag agttcatgcc tcaccgtggg     480
tttggtaagc taatgagtcc agaaagtaca accaccgggc ataggctgga tgctgctggg     540
gaaatgcatg aatcatcacc tttacagcca tcttttaaata tgggtttggc tgtgaatccg     600
tttagcccat cttttgcaac cgaggctgtc gagggaatga acacatcag tccttctcag      660 tccaacatgg tccattgctc tgcttctaat atactgcaaa agccatcaag acctgctatt     720
tcaactcctc ctgtggctag taaatccgct caggcgcgga ttggaaggcc tcctgtcgaa     780
gggcgaggga gaggccactt gcttccgcgg tattggccaa aatatacgga taaagaggtt     840
cagcagatct ctggaaattt gaatttgaac attgtacctc tctttgagaa aactcttagt     900
gccagtgatg ctggtcgcat tggtcgtcta gttcttccaa aagcctgtgc agaggcatat     960
tttcctccga ttagtcaatc cgaaggcatt cctttgaaaa tccaagatgt gaggggtagg    1020
gagtggacgt tccagttcag atattggccc aataacaata gtagaatgta tgttttagaa    1080
ggtgtcactc catgcataca gtccatgatg ctacaggctg gtgatacagt aactttcagt    1140
```

```
cgggttgatc ctggcggaaa actaatcatg ggttccagga aggcagctaa tgctggagac    1200
atgcagggtt gtgggctcac caacggaaca tcaactgagg acacatcatc gtctggtgta    1260
acagaaaacc caccctccat aaatggttcc tcgtgtattt cactaatacc gaaagagttg    1320
aatggtatgc ctgagaattt gaacagtgag actaacgggg caggatagg tgatgatcct     1380 acacgagtta agagaagaa gagaactcga accattggtg caaaaaataa gagacttctt     1440
ttgcatagtg aagaatctat ggagctgaga ctcacttggg aagaagctca ggacttgctt    1500
cgtccctctc ctagtgtaaa gcctaccatc gttgtcattg aggagcaaga aattgaagaa    1560
tatgacgaac ctcctgtctt tggaaagagg actatagtca ctacaaaacc ttcaggtgaa    1620
caggaacgat gggcaacttg cgacgactgc tctaaatgga aaggttacc tgtagatgct     1680 cttctttcct ttaaatggac atgtatagac aatgtttggg atgtgagtag gtgttcatgt    1740
tctgcaccgg aggagagtct gaaggaactt gagaatgttc ttaaagtagg aagagagcac    1800
aagaagagaa gaactgggga agccaggca gcaaaaagtc agcaagaacc gtgtggtttg     1860
gacgcactgg cgagtgcagc agtcttagga gacacaatag cgagccaga ggtagcgacc     1920 acgaccagac atccaaggca cagggctgga tgctcttgca tcgtgtgcat tcagccacca    1980
agtgggaaag gtaggcacaa gcctacatgt ggctgcactg tgtgtagcac cgtgaagaga    2040
aggttcaaga cgcttatgat gaggaggaag aagaagcagt ggagcgcga tgtaacagca    2100 gcagaagata agaagaagaa ggacatggaa ctggctgagt ctgataagag taaggaggag    2160
aaggaagtga acacagcgag aatagacctg aacagtgatc catacaataa agaagatgtt    2220
gaagctgttg cggtggagaa agaagagagt cgaaaaagag caataggaca gtgttcgggc    2280
gtggtggctc aagacgccag tgatgtttta ggagttacag agttagaagg agagggtaag    2340
aatgttcgtg aagagccgag agtttcaagc tga                                2373

<210> SEQ ID NO 42
<211> LENGTH: 790
<212> TYPE: PRT
<213> ORGANISM: Arabidopsis thaliana

<400> SEQUENCE: 42

Met Phe Glu Val Lys Met Gly Ser Lys Met Cys Met Asn Ala Ser Cys
1               5                   10                  15

Gly Thr Thr Ser Thr Val Glu Trp Lys Lys Gly Trp Pro Leu Arg Ser
            20                  25                  30

Gly Leu Leu Ala Asp Leu Cys Tyr Arg Cys Gly Ser Ala Tyr Glu Ser
        35                  40                  45

Ser Leu Phe Cys Glu Gln Phe His Lys Asp Gln Ser Gly Trp Arg Glu
    50                  55                  60

Cys Tyr Leu Cys Ser Lys Arg Leu His Cys Gly Cys Ile Ala Ser Lys
65                  70                  75                  80

Val Thr Ile Glu Leu Met Asp Tyr Gly Gly Val Gly Cys Ser Thr Cys
                85                  90                  95

Ala Cys Cys His Gln Leu Asn Leu Asn Thr Arg Gly Glu Asn Pro Gly
            100                 105                 110

Val Phe Ser Arg Leu Pro Met Lys Thr Leu Ala Asp Arg Gln His Val
        115                 120                 125

Asn Gly Glu Ser Gly Gly Arg Asn Glu Gly Asp Leu Phe Ser Gln Pro
    130                 135                 140

Leu Val Met Gly Gly Asp Lys Arg Glu Glu Phe Met Pro His Arg Gly
```

```
                                      -continued
145                 150                 155                 160

Phe Gly Lys Leu Met Ser Pro Glu Ser Thr Thr Gly His Arg Leu
                165                 170                 175

Asp Ala Ala Gly Glu Met His Glu Ser Ser Pro Leu Gln Pro Ser Leu
            180                 185                 190

Asn Met Gly Leu Ala Val Asn Pro Phe Ser Pro Ser Phe Ala Thr Glu
            195                 200                 205

Ala Val Glu Gly Met Lys His Ile Ser Pro Ser Gln Ser Asn Met Val
            210                 215                 220

His Cys Ser Ala Ser Asn Ile Leu Gln Lys Pro Ser Arg Pro Ala Ile
225                 230                 235                 240

Ser Thr Pro Pro Val Ala Ser Lys Ser Ala Gln Ala Arg Ile Gly Arg
                245                 250                 255

Pro Pro Val Glu Gly Arg Gly Arg Gly His Leu Leu Pro Arg Tyr Trp
                260                 265                 270

Pro Lys Tyr Thr Asp Lys Glu Val Gln Gln Ile Ser Gly Asn Leu Asn
                275                 280                 285

Leu Asn Ile Val Pro Leu Phe Glu Lys Thr Leu Ser Ala Ser Asp Ala
            290                 295                 300

Gly Arg Ile Gly Arg Leu Val Leu Pro Lys Ala Cys Ala Glu Ala Tyr
305                 310                 315                 320

Phe Pro Pro Ile Ser Gln Ser Glu Gly Ile Pro Leu Lys Ile Gln Asp
                325                 330                 335

Val Arg Gly Arg Glu Trp Thr Phe Gln Phe Arg Tyr Trp Pro Asn Asn
                340                 345                 350

Asn Ser Arg Met Tyr Val Leu Glu Gly Val Thr Pro Cys Ile Gln Ser
                355                 360                 365

Met Met Leu Gln Ala Gly Asp Thr Val Thr Phe Ser Arg Val Asp Pro
        370                 375                 380

Gly Gly Lys Leu Ile Met Gly Ser Arg Lys Ala Asn Ala Gly Asp
385                 390                 395                 400

Met Gln Gly Cys Gly Leu Thr Asn Gly Thr Ser Thr Glu Asp Thr Ser
                405                 410                 415

Ser Ser Gly Val Thr Glu Asn Pro Pro Ser Ile Asn Gly Ser Ser Cys
            420                 425                 430

Ile Ser Leu Ile Pro Lys Glu Leu Asn Gly Met Pro Glu Asn Leu Asn
            435                 440                 445

Ser Glu Thr Asn Gly Gly Arg Ile Gly Asp Asp Pro Thr Arg Val Lys
    450                 455                 460

Glu Lys Lys Arg Thr Arg Thr Ile Gly Ala Lys Asn Lys Arg Leu Leu
465                 470                 475                 480

Leu His Ser Glu Glu Ser Met Glu Leu Arg Leu Thr Trp Glu Glu Ala
                485                 490                 495

Gln Asp Leu Leu Arg Pro Ser Pro Ser Val Lys Pro Thr Ile Val Val
            500                 505                 510

Ile Glu Glu Gln Glu Ile Glu Glu Tyr Asp Glu Pro Pro Val Phe Gly
            515                 520                 525

Lys Arg Thr Ile Val Thr Thr Lys Pro Ser Gly Glu Gln Glu Arg Trp
        530                 535                 540

Ala Thr Cys Asp Asp Cys Ser Lys Trp Arg Arg Leu Pro Val Asp Ala
545                 550                 555                 560

Leu Leu Ser Phe Lys Trp Thr Cys Ile Asp Asn Val Trp Asp Val Ser
                565                 570                 575
```

Arg Cys Ser Cys Ser Ala Pro Glu Glu Ser Leu Lys Glu Leu Glu Asn
            580                 585                 590

Val Leu Lys Val Gly Arg Glu His Lys Lys Arg Arg Thr Gly Glu Ser
            595                 600                 605

Gln Ala Ala Lys Ser Gln Gln Glu Pro Cys Gly Leu Asp Ala Leu Ala
            610                 615                 620

Ser Ala Ala Val Leu Gly Asp Thr Ile Gly Pro Glu Val Ala Thr
625                 630                 635                 640

Thr Thr Arg His Pro Arg His Arg Ala Gly Cys Ser Cys Ile Val Cys
            645                 650                 655

Ile Gln Pro Pro Ser Gly Lys Gly Arg His Lys Pro Thr Cys Gly Cys
            660                 665                 670

Thr Val Cys Ser Thr Val Lys Arg Phe Lys Thr Leu Met Met Arg
            675                 680                 685

Arg Lys Lys Lys Gln Leu Glu Arg Asp Val Thr Ala Ala Glu Asp Lys
            690                 695                 700

Lys Lys Lys Asp Met Glu Leu Ala Glu Ser Asp Lys Ser Lys Glu Glu
705                 710                 715                 720

Lys Glu Val Asn Thr Ala Arg Ile Asp Leu Asn Ser Asp Pro Tyr Asn
            725                 730                 735

Lys Glu Asp Val Glu Ala Val Ala Val Glu Lys Glu Glu Ser Arg Lys
            740                 745                 750

Arg Ala Ile Gly Gln Cys Ser Gly Val Val Ala Gln Asp Ala Ser Asp
            755                 760                 765

Val Leu Gly Val Thr Glu Leu Glu Gly Glu Gly Lys Asn Val Arg Glu
            770                 775                 780

Glu Pro Arg Val Ser Ser
785                 790

<210> SEQ ID NO 43
<211> LENGTH: 2343
<212> TYPE: DNA
<213> ORGANISM: Arabidopsis thaliana

<400> SEQUENCE: 43
atggagtcaa taaaggtttg catgaacgca ctgtgcggag cggcctctac gtcgggcgag      60
tggaaaaaag ctggcctat gcgatccggt gatttagctt ctctctgcga taagtgtggg     120
tgtgcatacg agcaatccat attctgtgaa gtgttccatg caaggaatc tggttggaga     180
gagtgtaatt catgtgacaa cgtcttcac tgtggatgca ttgcttctag atttatgatg     240
gagcttctag agaatggtgg tgttacctgt ataagttgcg ccaagaaatc cggactaatt     300
tctatgaatg tgagccatga atctaacggt aaggacttcc cctcatttgc ttcagcagag     360
catgtaggca gtgttcttga gaggacaaat ctcaagcact tgcttcactt tcaaagaatc     420
gaccccactc attcttctct tcaaatgaaa caagaagaat cgctgcttcc ttccagccta     480
gatgctctta gacacaaaac tgaaggaaa gaattgtctg cacagccaaa cttgagcatt     540
tcacttggac ctacgcttat gacaagccca tttcatgatg ctgctgttga tgacagaagt     600
aagactaatt cgattttcca actggcccct cggtccaggc agctgcttcc aaaacctgca     660
aattcagctc ccattgctgc tggcatggag cctagtggga gcctggtgtc acagattcat     720
gtcgctcggc ctcctccaga aggtcgcggg aagacccaat tgcttccccg ttactggcct     780
aggattactg accaagagct gctgcaatta tctggacagt atcctcatct ctcaaattcc     840

```
aaaattatac cactctttga aaaagttctg agtgcgagcg atgcgggtcg tattggtcga      900
ctggttcttc cgaaagcatg tgcagaggca tatttccccc ctatatctct acccgagggt      960
ctcccgttaa agatacaaga cataaaaggg aaagaatggg tgttccagtt caggttttgg     1020
cctaataata acagcaggat gtacgttttg gagggtgtga ctccttgcat acagtccatg     1080
cagttgcaag ctggtgacac tgtaacattc agccgtacag aacctgaagg aaaactcgta     1140
atgggatacc gtaaagcgac gaactctaca gcgacacaga tgttcaaggg aagcagtgaa     1200
cccaatctga acatgttttc caacagcttg aatccgggat gtggtgacat caattggtct     1260
aaactagaga agtctgagga catggcaaag ataacttat ttcttcagtc gtccttaact      1320
tctgctagga acgggttcg gaacattggg actaagagca agcgtctgct cattgatagc     1380
gtagatgttc tggaactgaa ataacttgg gaggaggcac aggagctgtt gcggcctccc     1440
caatccacca aacccagcat ctttacgctg aaaatcaag attttgaaga atatgacgaa     1500
ccaccagttt cgggaagag dacccttttt gtctcacgtc aaacagggga acaagagcaa     1560
tgggtgcagt gtgatgcttg tgggaaatgg cgacagctgc cggtggatat tcttcttcca     1620
ccaaagtggt cgtgctctga taatctcttg gatcctggca ggtcttcatg ttccgcacct     1680
gatgaactct ctccaagaga acaggataca cttgtccggc agagcaaaga gttcaaaagg     1740
aggagactgg catcatcaaa cgaaaagcta accagtcgc aggatgcatc tgctctgaat     1800
agtttaggaa atgcaggcat caccacaacc ggtgaacagg gggaaatcac ggttgcagcc     1860
acgaccaagc atccaagaca ccgggcaggg tgttcgtgca tcgtctgcag ccaaccaccg     1920
agcggaaaag gcaaacacaa gccgtcatgc acttgcactg tgtgcgaggc agtgaagaga     1980
cgattcagga cgctcatgct gcggaagcgg aacaaaggag aggcaggaca ggcaagccag     2040
caggcgcagt cacagtcaga gtgcagggac gagacagaag tggagagcat ccagcggtt      2100
gaactagccg caggggaaaa catcgacttg aactcagacc cggggggcttc ccgagtaagc     2160
atgatgaggc ttctccaagc tgcagcgttt cctctggaag catatctgaa acaaaaggct     2220
atttccaata cagcaggaga acagcaaagc agtgatatgg tcagcacaga acacggttcg     2280
tcctcagccg cacaagaaac tgagaaagac acaacaaatg gagctcatga tcctgtgaac     2340
taa                                                                    2343

<210> SEQ ID NO 44
<211> LENGTH: 780
<212> TYPE: PRT
<213> ORGANISM: Arabidopsis thaliana

<400> SEQUENCE: 44

Met Glu Ser Ile Lys Val Cys Met Asn Ala Leu Cys Gly Ala Ala Ser
1               5                   10                  15

Thr Ser Gly Glu Trp Lys Lys Gly Trp Pro Met Arg Ser Gly Asp Leu
            20                  25                  30

Ala Ser Leu Cys Asp Lys Cys Gly Cys Ala Tyr Glu Gln Ser Ile Phe
        35                  40                  45

Cys Glu Val Phe His Ala Lys Glu Ser Gly Trp Arg Glu Cys Asn Ser
    50                  55                  60

Cys Asp Lys Arg Leu His Cys Gly Cys Ile Ala Ser Arg Phe Met Met
65                  70                  75                  80

Glu Leu Leu Glu Asn Gly Gly Val Thr Cys Ile Ser Cys Ala Lys Lys
                85                  90                  95

Ser Gly Leu Ile Ser Met Asn Val Ser His Glu Ser Asn Gly Lys Asp
```

-continued

```
            100                 105                 110
Phe Pro Ser Phe Ala Ser Ala Glu His Val Gly Ser Val Leu Glu Arg
            115                 120                 125
Thr Asn Leu Lys His Leu Leu His Phe Gln Arg Ile Asp Pro Thr His
        130                 135                 140
Ser Ser Leu Gln Met Lys Gln Glu Glu Ser Leu Leu Pro Ser Ser Leu
145                 150                 155                 160
Asp Ala Leu Arg His Lys Thr Glu Arg Lys Glu Leu Ser Ala Gln Pro
                165                 170                 175
Asn Leu Ser Ile Ser Leu Gly Pro Thr Leu Met Thr Ser Pro Phe His
            180                 185                 190
Asp Ala Ala Val Asp Asp Arg Ser Lys Thr Asn Ser Ile Phe Gln Leu
        195                 200                 205
Ala Pro Arg Ser Arg Gln Leu Leu Pro Lys Pro Ala Asn Ser Ala Pro
    210                 215                 220
Ile Ala Ala Gly Met Glu Pro Ser Gly Ser Leu Val Ser Gln Ile His
225                 230                 235                 240
Val Ala Arg Pro Pro Pro Glu Gly Arg Gly Lys Thr Gln Leu Leu Pro
                245                 250                 255
Arg Tyr Trp Pro Arg Ile Thr Asp Gln Glu Leu Leu Gln Leu Ser Gly
            260                 265                 270
Gln Tyr Pro His Leu Ser Asn Ser Lys Ile Ile Pro Leu Phe Glu Lys
        275                 280                 285
Val Leu Ser Ala Ser Asp Ala Gly Arg Ile Gly Arg Leu Val Leu Pro
    290                 295                 300
Lys Ala Cys Ala Glu Ala Tyr Phe Pro Pro Ile Ser Leu Pro Glu Gly
305                 310                 315                 320
Leu Pro Leu Lys Ile Gln Asp Ile Lys Gly Lys Glu Trp Val Phe Gln
                325                 330                 335
Phe Arg Phe Trp Pro Asn Asn Asn Ser Arg Met Tyr Val Leu Glu Gly
            340                 345                 350
Val Thr Pro Cys Ile Gln Ser Met Gln Leu Gln Ala Gly Asp Thr Val
        355                 360                 365
Thr Phe Ser Arg Thr Glu Pro Glu Gly Lys Leu Val Met Gly Tyr Arg
    370                 375                 380
Lys Ala Thr Asn Ser Thr Ala Thr Gln Met Phe Lys Gly Ser Ser Glu
385                 390                 395                 400
Pro Asn Leu Asn Met Phe Ser Asn Ser Leu Asn Pro Gly Cys Gly Asp
                405                 410                 415
Ile Asn Trp Ser Lys Leu Glu Lys Ser Glu Asp Met Ala Lys Asp Asn
            420                 425                 430
Leu Phe Leu Gln Ser Ser Leu Thr Ser Ala Arg Lys Arg Val Arg Asn
        435                 440                 445
Ile Gly Thr Lys Ser Lys Arg Leu Leu Ile Asp Ser Val Asp Val Leu
    450                 455                 460
Glu Leu Lys Ile Thr Trp Glu Glu Ala Gln Glu Leu Leu Arg Pro Pro
465                 470                 475                 480
Gln Ser Thr Lys Pro Ser Ile Phe Thr Leu Glu Asn Gln Asp Phe Glu
                485                 490                 495
Glu Tyr Asp Glu Pro Pro Val Phe Gly Lys Arg Thr Leu Phe Val Ser
            500                 505                 510
Arg Gln Thr Gly Glu Gln Glu Gln Trp Val Gln Cys Asp Ala Cys Gly
        515                 520                 525
```

```
Lys Trp Arg Gln Leu Pro Val Asp Ile Leu Leu Pro Pro Lys Trp Ser
    530                 535                 540

Cys Ser Asp Asn Leu Leu Asp Pro Gly Arg Ser Ser Cys Ser Ala Pro
545                 550                 555                 560

Asp Glu Leu Ser Pro Arg Glu Gln Asp Thr Leu Val Arg Gln Ser Lys
                565                 570                 575

Glu Phe Lys Arg Arg Leu Ala Ser Ser Asn Glu Lys Leu Asn Gln
                580                 585                 590

Ser Gln Asp Ala Ser Ala Leu Asn Ser Leu Gly Asn Ala Gly Ile Thr
        595                 600                 605

Thr Thr Gly Glu Gln Gly Glu Ile Thr Val Ala Ala Thr Thr Lys His
    610                 615                 620

Pro Arg His Arg Ala Gly Cys Ser Cys Ile Val Cys Ser Gln Pro Pro
625                 630                 635                 640

Ser Gly Lys Gly Lys His Lys Pro Ser Cys Thr Cys Thr Val Cys Glu
                645                 650                 655

Ala Val Lys Arg Arg Phe Arg Thr Leu Met Leu Arg Lys Arg Asn Lys
                660                 665                 670

Gly Glu Ala Gly Gln Ala Ser Gln Gln Ala Gln Ser Gln Ser Glu Cys
        675                 680                 685

Arg Asp Glu Thr Glu Val Glu Ser Ile Pro Ala Val Glu Leu Ala Ala
    690                 695                 700

Gly Glu Asn Ile Asp Leu Asn Ser Asp Pro Gly Ala Ser Arg Val Ser
705                 710                 715                 720

Met Met Arg Leu Leu Gln Ala Ala Ala Phe Pro Leu Glu Ala Tyr Leu
                725                 730                 735

Lys Gln Lys Ala Ile Ser Asn Thr Ala Gly Glu Gln Gln Ser Ser Asp
                740                 745                 750

Met Val Ser Thr Glu His Gly Ser Ser Ser Ala Ala Gln Glu Thr Glu
        755                 760                 765

Lys Asp Thr Thr Asn Gly Ala His Asp Pro Val Asn
    770                 775                 780

<210> SEQ ID NO 45
<211> LENGTH: 2166
<212> TYPE: DNA
<213> ORGANISM: Arabidopsis thaliana

<400> SEQUENCE: 45
atgagatact tttgctcttta ctacttcttg attgtaaaca tgcatacatg tgttctgtct      60
ttgatgggtt tatttttgga aaacatctct gcgtatgaac aaggaaagtt ttgtgacgta     120
tttcaccaaa gggcttctgg atggaggtgt tgtgagtcat gtggaaagca tttcgtgcag     180
cgaattcatt gtggatgtat tgcgtctgct tctgcttata cgttaatgga tgctggagga     240
attgagtgtt tggcttgcgc aagaaaaaag tttgctttgt ctccaatttc tgagaaattc     300
aaggacttgt cgatcaactg gagttcttca actagatcaa atcagataag ctaccagcct     360
cctagttgtt tagatccttc agttctgcag tttgattttc gtaatcgtgg aggtaataat     420
gaatttagtc aacctgcttc taaagaaagg gtcactgcat gtaccatgga gaaaaaagg      480 ggaatgaatg acatgatagg gaaattaatg agtgaaaact cgaaacatta tagagtatct     540
ccttttccaa atgtcaatgt atatcaccca ctgatctcac taaaggaggg tccatgtggg     600
acacagcttg cgtttcctgt gccaattaca acaccaattg agaaaactgg tcactctaga     660
```

-continued

```
ctagatggaa gtaatttatg gcacacacgt aattcttctc cgctaagtcg cttacacaat    720
gacttgaatg gtggagcaga ctcgccattc gaaagcaaaa gtcgtaatgt gatggctcat    780
cttgagacgc caggaaaata tcaggtggtt ccacgatttt ggcccaaggt ttcatataaa    840
aaccaagttc tgcagaatca atcaaaagag tatccttctt ctcttataga tactacattg    900
gaatataact ttaagatcct gagtgcaact gatactggaa agcggctggt cctgccaaag    960
aaatatgcag aggctttctt gccccaactt ccccacacca aggtgtgcc tctcacagta   1020
caggacccaa tgggtaaaga gtggagattt cagtttcgct tttggcccag cagcaaaggc   1080
agaatatatg ttctagaggg agtaactcca ttcatacaga ccttgcagtt gcaggctggt   1140
gatacagtca tattcagtcg attagatcca gaaggaagt taattttggg attcagaaag    1200
gcttcgatta ctcaatcgtc tgatcaggct gatccggctg atatgcattc accgtttgaa   1260
gttaagaagt ctgcttatat aactaaagaa accccaggag tagaatgttc ctctggtaag   1320
aagaaaagca gcatgatgat tacaagaagt aaacgtcaaa aagttgaaaa gggagacgac   1380
aacttgctga agctaacatg ggaagaagct caaggatttc tcctgcctcc tcccaacctc   1440
actccatcta gagttgtgat agaggattac gagtttgagg agtatgagga tttggctgta   1500
gtttctcaag tttcttctgg aatacaagat tatttcatga tattaaaaat aacctgttgt   1560
tcatatacac attgggtgct agaagttgag gctccaatca tcgggaagcc tactgatgtt   1620
gcaggatcaa cgtgcactga agttgaagga ctgttgatat caccaacaac cacaaagcac   1680
ccacgacata gagatggctg tacttgcatc atttgcatac aatccccaag tgggataggt   1740
cctaaacacg accgatgctg ttcttgtgca gtctgcgaca ctaacaaacg ccgtaggcgt   1800
tccctgttgc tacggaggga aaagaagcag atggagaaag aagacaatgc gcgcaagttg   1860
ctcgagcaac tgaattctga taatggactt caccaatctg ctaacaacag tgagaatcat   1920
gagcgtcatg cttcgccttt gaaagttcaa ttagatttga acttcaaacc agaaaaggac   1980
gaagaatctc tccctggttc taacaaaact accaagagcg agactctgcc tcatgatgac   2040
acagtaaagt ctagcttcac gtcaccaagc tcatcaagtg ctcatagcca aaataacaag   2100
gaagatgaag gaaaactcaa gacaaccaca gaaattgcag acaccaccac cacaagctcc   2160
atgtag                                                              2166
```

<210> SEQ ID NO 46
<211> LENGTH: 721
<212> TYPE: PRT
<213> ORGANISM: Arabidopsis thaliana

<400> SEQUENCE: 46

```
Met Arg Tyr Phe Cys Ser Tyr Tyr Phe Leu Ile Val Asn Met His Thr
1               5                   10                  15

Cys Val Leu Ser Leu Met Gly Leu Phe Leu Glu Asn Ile Ser Ala Tyr
            20                  25                  30

Glu Gln Gly Lys Phe Cys Asp Val Phe His Gln Arg Ala Ser Gly Trp
        35                  40                  45

Arg Cys Cys Glu Ser Cys Gly Lys His Phe Val Gln Arg Ile His Cys
    50                  55                  60

Gly Cys Ile Ala Ser Ala Ser Ala Tyr Thr Leu Met Asp Ala Gly Gly
65                  70                  75                  80

Ile Glu Cys Leu Ala Cys Ala Arg Lys Lys Phe Ala Leu Ser Pro Ile
                85                  90                  95

Ser Glu Lys Phe Lys Asp Leu Ser Ile Asn Trp Ser Ser Ser Thr Arg
```

-continued

```
                100                 105                 110
Ser Asn Gln Ile Ser Tyr Gln Pro Pro Ser Cys Leu Asp Pro Ser Val
            115                 120                 125

Leu Gln Phe Asp Phe Arg Asn Arg Gly Gly Asn Asn Glu Phe Ser Gln
130                 135                 140

Pro Ala Ser Lys Glu Arg Val Thr Ala Cys Thr Met Glu Lys Lys Arg
145                 150                 155                 160

Gly Met Asn Asp Met Ile Gly Lys Leu Met Ser Glu Asn Ser Lys His
                165                 170                 175

Tyr Arg Val Ser Pro Phe Pro Asn Val Asn Val Tyr His Pro Leu Ile
            180                 185                 190

Ser Leu Lys Glu Gly Pro Cys Gly Thr Gln Leu Ala Phe Pro Val Pro
        195                 200                 205

Ile Thr Thr Pro Ile Glu Lys Thr Gly His Ser Arg Leu Asp Gly Ser
    210                 215                 220

Asn Leu Trp His Thr Arg Asn Ser Ser Pro Leu Ser Arg Leu His Asn
225                 230                 235                 240

Asp Leu Asn Gly Gly Ala Asp Ser Pro Phe Glu Ser Lys Ser Arg Asn
                245                 250                 255

Val Met Ala His Leu Glu Thr Pro Gly Lys Tyr Gln Val Val Pro Arg
            260                 265                 270

Phe Trp Pro Lys Val Ser Tyr Lys Asn Gln Val Leu Gln Asn Gln Ser
        275                 280                 285

Lys Glu Tyr Pro Ser Ser Leu Ile Asp Thr Thr Leu Glu Tyr Asn Phe
    290                 295                 300

Lys Ile Leu Ser Ala Thr Asp Thr Gly Lys Arg Leu Val Leu Pro Lys
305                 310                 315                 320

Lys Tyr Ala Glu Ala Phe Leu Pro Gln Leu Ser His Thr Lys Gly Val
                325                 330                 335

Pro Leu Thr Val Gln Asp Pro Met Gly Lys Glu Trp Arg Phe Gln Phe
            340                 345                 350

Arg Phe Trp Pro Ser Ser Lys Gly Arg Ile Tyr Val Leu Glu Gly Val
        355                 360                 365

Thr Pro Phe Ile Gln Thr Leu Gln Leu Gln Ala Gly Asp Thr Val Ile
    370                 375                 380

Phe Ser Arg Leu Asp Pro Glu Arg Lys Leu Ile Leu Gly Phe Arg Lys
385                 390                 395                 400

Ala Ser Ile Thr Gln Ser Ser Asp Gln Ala Asp Pro Ala Asp Met His
                405                 410                 415

Ser Pro Phe Glu Val Lys Lys Ser Ala Tyr Ile Thr Lys Glu Thr Pro
            420                 425                 430

Gly Val Glu Cys Ser Ser Gly Lys Lys Lys Ser Ser Met Met Ile Thr
        435                 440                 445

Arg Ser Lys Arg Gln Lys Val Glu Lys Gly Asp Asp Asn Leu Leu Lys
    450                 455                 460

Leu Thr Trp Glu Glu Ala Gln Gly Phe Leu Leu Pro Pro Asn Leu
465                 470                 475                 480

Thr Pro Ser Arg Val Val Ile Glu Asp Tyr Glu Phe Glu Glu Tyr Glu
                485                 490                 495

Asp Leu Ala Val Val Ser Gln Val Ser Ser Gly Ile Gln Asp Tyr Phe
            500                 505                 510

Met Ile Leu Lys Ile Thr Cys Cys Ser Tyr Thr His Trp Val Leu Glu
        515                 520                 525
```

| | | | | | | | | | | |
|---|---|---|---|---|---|---|---|---|---|---|
|Val|Glu|Ala|Pro|Ile|Ile|Gly|Lys|Pro|Thr|Asp|Val|Ala|Gly|Ser|Thr|
| |530| | | |535| | | |540| |

Cys Thr Glu Val Glu Gly Leu Leu Ile Ser Pro Thr Thr Lys His
545                 550                 555                 560

Pro Arg His Arg Asp Gly Cys Thr Cys Ile Ile Cys Ile Gln Ser Pro
                565                 570                 575

Ser Gly Ile Gly Pro Lys His Asp Arg Cys Cys Ser Cys Ala Val Cys
            580                 585                 590

Asp Thr Asn Lys Arg Arg Arg Ser Leu Leu Leu Arg Arg Glu Lys
        595                 600                 605

Lys Gln Met Glu Lys Glu Asp Asn Ala Arg Lys Leu Leu Glu Gln Leu
    610                 615                 620

Asn Ser Asp Asn Gly Leu His Gln Ser Ala Asn Asn Ser Glu Asn His
625                 630                 635                 640

Glu Arg His Ala Ser Pro Leu Lys Val Gln Leu Asp Leu Asn Phe Lys
                645                 650                 655

Pro Glu Lys Asp Glu Glu Ser Leu Pro Gly Ser Asn Lys Thr Thr Lys
                660                 665                 670

Ser Glu Thr Leu Pro His Asp Asp Thr Val Lys Ser Ser Phe Thr Ser
            675                 680                 685

Pro Ser Ser Ser Ala His Ser Gln Asn Asn Lys Glu Asp Glu Gly
        690                 695                 700

Lys Leu Lys Thr Thr Thr Glu Ile Ala Asp Thr Thr Thr Ser Ser
705                 710                 715                 720

Met

<210> SEQ ID NO 47
<211> LENGTH: 987
<212> TYPE: DNA
<213> ORGANISM: Arabidopsis thaliana

<400> SEQUENCE: 47

```
atgaatcttg accaagaact cgccgagatc agagctagca gttccgacca caccaattac      60
ttctacagct cggagaggag agagcacatg ttcgacaaag tgttgacacc aagtgacgtc     120
ggtaaactaa accggctcgt gattccaaag caacatgcag agaacttctt cccttttagag   180
gacaatcaaa acggcacagt gttggatttc aagacaaaaa cggcaagat gtggaggttt     240
cgttactcgt attggaacag tagccaaagc tacgtgatga ccaaaggatg agccgtttc     300
gtcaaggaga gaaactcttc gccggagaca ccgtctcttt ctaccgtgg ctacatccct     360
gacgataacg cacaaccgga gagacgacgg aaaataatgt tcatcgattg gaggcctaga    420
gccgagataa acttcgtaca acacattaac aatcataact tcgttttcgg gtctccgaca    480
tatccaacgg ctaggtttta tccggtgacg ccggaatatt ccatgccata ccggagtttt    540
ccaccgtttt atcagaacca atttcaagaa cgggaatatt tagggtatgg ttatggtaga    600
gttgttaatg gtaatggagt gcgttactac gcaggatcac cgttggatca acatcatcag    660
tggaatcttg gtcgatctga gccgttggtt tatgactcgg ttccagtttt tccagcgggg    720
agggtacctc cgtcggcgcc tcctcagccg tcgacgacga agaagctgag gctgtttggg    780
gttgacgtgg aagagtcttc atcttcaggg gatacacgtg gcgaaatggg agtagcaggg    840
tactcttcct cgtctccggt tgtgatcaga gacgatgatc aatcattttg gaggtcgcca    900
cgtggcgaaa tggcatcgtc ttcttcggct atgcagctaa gtgatgatga agaatataag    960
```
aggaaaggga aatctttaga gctttga        987

<210> SEQ ID NO 48
<211> LENGTH: 328
<212> TYPE: PRT
<213> ORGANISM: Arabidopsis thaliana

<400> SEQUENCE: 48

Met Asn Leu Asp Gln Glu Leu Ala Glu Ile Arg Ala Ser Ser Ser Asp
1               5                   10                  15

His Thr Asn Tyr Phe Tyr Ser Ser Glu Arg Arg Glu His Met Phe Asp
            20                  25                  30

Lys Val Leu Thr Pro Ser Asp Val Gly Lys Leu Asn Arg Leu Val Ile
        35                  40                  45

Pro Lys Gln His Ala Glu Asn Phe Phe Pro Leu Glu Asp Asn Gln Asn
    50                  55                  60

Gly Thr Val Leu Asp Phe Gln Asp Lys Asn Gly Lys Met Trp Arg Phe
65                  70                  75                  80

Arg Tyr Ser Tyr Trp Asn Ser Ser Gln Ser Tyr Val Met Thr Lys Gly
                85                  90                  95

Trp Ser Arg Phe Val Lys Glu Lys Lys Leu Phe Ala Gly Asp Thr Val
            100                 105                 110

Ser Phe Tyr Arg Gly Tyr Ile Pro Asp Asp Asn Ala Gln Pro Glu Arg
        115                 120                 125

Arg Arg Lys Ile Met Phe Ile Asp Trp Arg Pro Arg Ala Glu Ile Asn
    130                 135                 140

Phe Val His Asn Ile Asn Asn His Asn Phe Val Phe Gly Ser Pro Thr
145                 150                 155                 160

Tyr Pro Thr Ala Arg Phe Tyr Pro Val Thr Pro Glu Tyr Ser Met Pro
                165                 170                 175

Tyr Arg Ser Phe Pro Pro Phe Tyr Gln Asn Gln Phe Gln Glu Arg Glu
            180                 185                 190

Tyr Leu Gly Tyr Gly Tyr Gly Arg Val Val Asn Gly Asn Gly Val Arg
        195                 200                 205

Tyr Tyr Ala Gly Ser Pro Leu Asp Gln His His Gln Trp Asn Leu Gly
    210                 215                 220

Arg Ser Glu Pro Leu Val Tyr Asp Ser Val Pro Val Phe Pro Ala Gly
225                 230                 235                 240

Arg Val Pro Pro Ser Ala Pro Pro Gln Pro Ser Thr Thr Lys Lys Leu
                245                 250                 255

Arg Leu Phe Gly Val Asp Val Glu Glu Ser Ser Ser Ser Gly Asp Thr
            260                 265                 270

Arg Gly Glu Met Gly Val Ala Gly Tyr Ser Ser Ser Pro Val Val
        275                 280                 285

Ile Arg Asp Asp Asp Gln Ser Phe Trp Arg Ser Pro Arg Gly Glu Met
    290                 295                 300

Ala Ser Ser Ser Ser Ala Met Gln Leu Ser Asp Asp Glu Glu Tyr Lys
305                 310                 315                 320

Arg Lys Gly Lys Ser Leu Glu Leu
                325

<210> SEQ ID NO 49
<211> LENGTH: 1059
<212> TYPE: DNA
<213> ORGANISM: Arabidopsis thaliana

<400> SEQUENCE: 49

```
atggacgaga tgagcaatgt agccaagaca acgacagaga cttcaggctt aactgactct      60
gtcttgagcc tcacgaaacg catgaaacct actgaggtta cgaccaccac aaaacctgcc     120
ttgtccaaca cgacgaaatt caaaggagtt gttcagcaac agaacggtca ttggggtgct     180
cagatttacg cagaccatcg aaggatttgg cttggaactt tcaaatccgc tcatgaagcc     240
gctgctgctt acgatagcgc atcgattaag cttcgaagct ttgatgctaa ctcgcaccgg     300
aacttccctt ggtctgattt taccctccat gaaccggact tcaagagtg ctacacgaca     360
gaagctgtgt tgaacatgat cagagacggt tcttatcaac acaagttcag agattttctc     420
agaatccggt ctcagattgt tgcgaatatc aacatcgtgg gatcaaaaca agtcttagga     480
ggaggagaag gtggtcaaga atcgaacaag tgtttctcgt gcacgcagct ttttcagaaa     540
gaactgacac cgagcgatgt agggaaactg aataggcttg tgatacctaa gaagtatgca     600
gtgaagtata tgcctttcat aagcgatgat caaagcgaga agagacgag tgaaggagta     660
gaagatgtgg aggttgtctt ttacgacaga gcaatgagac aatggaagtt taggtattgt     720
tactggagaa gtagccagag ctttgtcttc accagaggat ggaatggttt cgtgaaggag     780
aagaatctca aggagaaaga tattattgtc ttttacactt gcgatgtccc caacaatgtg     840
aagacattag aaggccaaag caagaccttc ttgatgattg atgttcatca cttttcaggc     900
aacggtttcg tggttcccga ggaagtaaac aagacggttc atgagatttc tgatgaagag     960
atgaaaacag aaaccctctt tacctcgaag gtagaagaag aaaccaaatc agaggagaag    1020
aaaggagggt ttatgctgtt tggtgttagg atccaatag                           1059
```

<210> SEQ ID NO 50
<211> LENGTH: 352
<212> TYPE: PRT
<213> ORGANISM: Arabidopsis thaliana

<400> SEQUENCE: 50

```
Met Asp Glu Met Ser Asn Val Ala Lys Thr Thr Glu Thr Ser Gly
1               5                   10                  15

Leu Thr Asp Ser Val Leu Ser Leu Thr Lys Arg Met Lys Pro Thr Glu
            20                  25                  30

Val Thr Thr Thr Thr Lys Pro Ala Leu Ser Asn Thr Thr Lys Phe Lys
        35                  40                  45

Gly Val Val Gln Gln Gln Asn Gly His Trp Gly Ala Gln Ile Tyr Ala
    50                  55                  60

Asp His Arg Arg Ile Trp Leu Gly Thr Phe Lys Ser Ala His Glu Ala
65                  70                  75                  80

Ala Ala Ala Tyr Asp Ser Ala Ser Ile Lys Leu Arg Ser Phe Asp Ala
                85                  90                  95

Asn Ser His Arg Asn Phe Pro Trp Ser Asp Phe Thr Leu His Glu Pro
            100                 105                 110

Asp Phe Gln Glu Cys Tyr Thr Thr Glu Ala Val Leu Asn Met Ile Arg
        115                 120                 125

Asp Gly Ser Tyr Gln His Lys Phe Arg Asp Phe Leu Arg Ile Arg Ser
    130                 135                 140

Gln Ile Val Ala Asn Ile Asn Ile Val Gly Ser Lys Gln Val Leu Gly
145                 150                 155                 160

Gly Gly Glu Gly Gly Gln Glu Ser Asn Lys Cys Phe Ser Cys Thr Gln
                165                 170                 175
```

Leu Phe Gln Lys Glu Leu Thr Pro Ser Asp Val Gly Lys Leu Asn Arg
                180                 185                 190

Leu Val Ile Pro Lys Lys Tyr Ala Val Lys Tyr Met Pro Phe Ile Ser
            195                 200                 205

Asp Asp Gln Ser Glu Lys Glu Thr Ser Glu Gly Val Glu Asp Val Glu
        210                 215                 220

Val Val Phe Tyr Asp Arg Ala Met Arg Gln Trp Lys Phe Arg Tyr Cys
225                 230                 235                 240

Tyr Trp Arg Ser Ser Gln Ser Phe Val Phe Thr Arg Gly Trp Asn Gly
                245                 250                 255

Phe Val Lys Glu Lys Asn Leu Lys Glu Lys Asp Ile Ile Val Phe Tyr
            260                 265                 270

Thr Cys Asp Val Pro Asn Asn Val Lys Thr Leu Glu Gly Gln Ser Lys
        275                 280                 285

Thr Phe Leu Met Ile Asp Val His His Phe Ser Gly Asn Gly Phe Val
        290                 295                 300

Val Pro Glu Glu Val Asn Lys Thr Val His Glu Ile Ser Asp Glu Glu
305                 310                 315                 320

Met Lys Thr Glu Thr Leu Phe Ser Lys Val Glu Glu Glu Thr Lys
                325                 330                 335

Ser Glu Glu Lys Lys Gly Gly Phe Met Leu Phe Gly Val Arg Ile Gln
                340                 345                 350

<210> SEQ ID NO 51
<211> LENGTH: 933
<212> TYPE: DNA
<213> ORGANISM: Arabidopsis thaliana

<400> SEQUENCE: 51
atgatgacag atttatctct cacgagagat gaagatgaag aagaagcaaa gcccttagca      60
gaagaagaag gagcgcgtga agtagcagac agagagcaca tgttcgacaa agttgtgact     120
ccaagtgatg tcggaaaact aaaccgactt gtgatcccaa agcaacacgc agagagattc     180
ttccctttag attcatcttc aaacgagaaa ggtttgcttt taaacttcga agatctcact     240
ggcaaatctt ggaggttccg ttactcttac tggaacagta gtcaaagcta tgtcatgact     300
aaaggttgga gcagattcgt taaagacaaa aagcttgacg ccggagatat tgtctctttc     360
caaagatgtg tcggagattc aggaagagat agccgtttgt ttattgattg gaggagaaga     420
cctaaagtcc ctgaccatcc tcatttcgcc gccggagcta tgttccctag gtttacagc      480 tttccttcga ccaattacag tctttataat catcagcagc aacgtcatca tcacagtggt     540
ggtggttata attatcatca aattccgaga gaatttggtt atggttactt cgttaggtca     600
gtggatcaga ggaacaatcc tgcggctgcg gtggctgatc cgttggtgat tgaatctgtg     660
ccggtgatga tgcacgggag agctaatcag gaacttgttg aacggccgg aagagactg      720 aggcttttg gagttgatat ggaatgcggc gagagcggaa tgaccaacag tacggaggag     780
gaatcatcat cttccggtgg aagtttgcca cgtggaggcg gtggtggtgc ttcatcttcc     840
tctttctttc agctgagact tggaagcagc agtgaagatg atcacttcac taagaaagga     900
aagtcttcat tgtctttga tttggatcaa taa                                  933

<210> SEQ ID NO 52
<211> LENGTH: 310
<212> TYPE: PRT
<213> ORGANISM: Arabidopsis thaliana

<400> SEQUENCE: 52

```
Met Met Thr Asp Leu Ser Leu Thr Arg Asp Glu Asp Glu Glu Ala
1               5                   10                  15

Lys Pro Leu Ala Glu Glu Gly Ala Arg Glu Val Ala Asp Arg Glu
            20                  25                  30

His Met Phe Asp Lys Val Val Thr Pro Ser Asp Val Gly Lys Leu Asn
        35                  40                  45

Arg Leu Val Ile Pro Lys Gln His Ala Glu Arg Phe Phe Pro Leu Asp
    50                  55                  60

Ser Ser Asn Glu Lys Gly Leu Leu Leu Asn Phe Gly Asp Leu Thr
65              70                  75                  80

Gly Lys Ser Trp Arg Phe Arg Tyr Ser Tyr Trp Asn Ser Ser Gln Ser
                85                  90                  95

Tyr Val Met Thr Lys Gly Trp Ser Arg Phe Val Lys Asp Lys Lys Leu
            100                 105                 110

Asp Ala Gly Asp Ile Val Ser Phe Gln Arg Cys Val Gly Asp Ser Gly
            115                 120                 125

Arg Asp Ser Arg Leu Phe Ile Asp Trp Arg Arg Pro Lys Val Pro
130                 135                 140

Asp His Pro His Phe Ala Ala Gly Ala Met Phe Pro Arg Phe Tyr Ser
145                 150                 155                 160

Phe Pro Ser Thr Asn Tyr Ser Leu Tyr Asn His Gln Gln Arg His
                165                 170                 175

His His Ser Gly Gly Tyr Asn Tyr His Gln Ile Pro Arg Glu Phe
            180                 185                 190

Gly Tyr Gly Tyr Phe Val Arg Ser Val Asp Gln Arg Asn Asn Pro Ala
        195                 200                 205

Ala Ala Val Ala Asp Pro Leu Val Ile Glu Ser Val Pro Val Met Met
210                 215                 220

His Gly Arg Ala Asn Gln Glu Leu Val Gly Thr Ala Gly Lys Arg Leu
225                 230                 235                 240

Arg Leu Phe Gly Val Asp Met Glu Cys Gly Glu Ser Gly Met Thr Asn
            245                 250                 255

Ser Thr Glu Glu Glu Ser Ser Ser Gly Gly Ser Leu Pro Arg Gly
            260                 265                 270

Gly Gly Gly Gly Ala Ser Ser Ser Phe Phe Gln Leu Arg Leu Gly
        275                 280                 285

Ser Ser Ser Glu Asp Asp His Phe Thr Lys Lys Gly Lys Ser Ser Leu
    290                 295                 300

Ser Phe Asp Leu Asp Gln
305                 310
```

<210> SEQ ID NO 53
<211> LENGTH: 1077
<212> TYPE: DNA
<213> ORGANISM: Arabidopsis thaliana

<400> SEQUENCE: 53

| | | | | | |
|---|---|---|---|---|---|
| atggatctat | ccctggctcc | gacaacaaca | acaagttccg | accaagaaca | agacagagac | 60 |
| caagaattaa | cctccaacat | cggagcaagc | agcagctccg | gtcccagcgg | aaacaacaac | 120 |
| aaccttccga | tgatgatgat | tccacctccg | gagaaagaac | acatgttcga | caaagtggta | 180 |
| acaccaagcg | acgtcggaaa | actcaacaga | ctcgtgatcc | ctaaacaaca | cgctgagagg | 240 |
| tatttccctc | tagactcctc | aaacaaccaa | aacggcacgc | ttttgaactt | ccaagacaga | 300 |

```
aacggcaaga tgtggagatt ccgttactcg tattggaact ctagccagag ctacgttatg    360
accaaaggat ggagccgttt cgtcaaagag aaaaagctcg atgcaggaga cattgtctct    420
ttccaacgag gcatcggaga tgagtcagaa agatccaaac tttacataga ttggaggcat    480
agacccgaca tgagcctcgt tcaagcacat cagtttggta attttggttt caatttcaat    540
ttcccgacca cttctcaata ttccaacaga tttcatccat gccagaata taactccgtc     600 ccgattcacc ggggcttaaa catcggaaat caccaacgtt cctattataa cacccagcgt    660
caagagttcg tagggtatgg ttatgggaat ttagctggaa ggtgttacta cacgggatca    720
ccgttggatc ataggaacat tgttggatca gagccgttgg ttatagactc agtccctgtg    780
gttcccggga gattaactcc ggtgatgtta ccgccgcttc ctccgcctcc ttctacggcg    840
ggaaagagac taaggctctt tggggtgaat atggaatgtg gcaatgacta taatcaacaa    900
gaagagtcat ggttggtgcc acgtggcgaa attggtgcat cttcttcttc ttcttcagct    960
ctacgactaa atttatcgac tgatcatgat gatgataatg atgatggtga tgatggcgat   1020
gatgatcaat tgctaagaa agggaagtct tcactttctc tcaatttcaa tccatga      1077
```

```
<210> SEQ ID NO 54
<211> LENGTH: 358
<212> TYPE: PRT
<213> ORGANISM: Arabidopsis thaliana

<400> SEQUENCE: 54
```

```
Met Asp Leu Ser Leu Ala Pro Thr Thr Thr Ser Ser Asp Gln Glu
1               5                   10                  15

Gln Asp Arg Asp Gln Glu Leu Thr Ser Asn Ile Gly Ala Ser Ser
            20                  25                  30

Ser Gly Pro Ser Gly Asn Asn Asn Leu Pro Met Met Met Ile Pro
        35                  40                  45

Pro Pro Glu Lys Glu His Met Phe Asp Lys Val Val Thr Pro Ser Asp
    50                  55                  60

Val Gly Lys Leu Asn Arg Leu Val Ile Pro Lys Gln His Ala Glu Arg
65                  70                  75                  80

Tyr Phe Pro Leu Asp Ser Ser Asn Asn Gln Asn Gly Thr Leu Leu Asn
                85                  90                  95

Phe Gln Asp Arg Asn Gly Lys Met Trp Arg Phe Arg Tyr Ser Tyr Trp
            100                 105                 110

Asn Ser Ser Gln Ser Tyr Val Met Thr Lys Gly Trp Ser Arg Phe Val
        115                 120                 125

Lys Glu Lys Lys Leu Asp Ala Gly Asp Ile Val Ser Phe Gln Arg Gly
    130                 135                 140

Ile Gly Asp Glu Ser Glu Arg Ser Lys Leu Tyr Ile Asp Trp Arg His
145                 150                 155                 160

Arg Pro Asp Met Ser Leu Val Gln Ala His Gln Phe Gly Asn Phe Gly
                165                 170                 175

Phe Asn Phe Asn Phe Pro Thr Thr Ser Gln Tyr Ser Asn Arg Phe His
            180                 185                 190

Pro Leu Pro Glu Tyr Asn Ser Val Pro Ile His Arg Gly Leu Asn Ile
        195                 200                 205

Gly Asn His Gln Arg Ser Tyr Tyr Asn Thr Gln Arg Gln Glu Phe Val
    210                 215                 220

Gly Tyr Gly Tyr Gly Asn Leu Ala Gly Arg Cys Tyr Tyr Thr Gly Ser
225                 230                 235                 240
```

```
Pro Leu Asp His Arg Asn Ile Val Gly Ser Glu Pro Leu Val Ile Asp
                245                 250                 255

Ser Val Pro Val Val Pro Gly Arg Leu Thr Pro Val Met Leu Pro Pro
            260                 265                 270

Leu Pro Pro Pro Pro Ser Thr Ala Gly Lys Arg Leu Arg Leu Phe Gly
        275                 280                 285

Val Asn Met Glu Cys Gly Asn Asp Tyr Asn Gln Gln Glu Glu Ser Trp
    290                 295                 300

Leu Val Pro Arg Gly Glu Ile Gly Ala Ser Ser Ser Ser Ser Ser Ala
305                 310                 315                 320

Leu Arg Leu Asn Leu Ser Thr Asp His Asp Asp Asn Asp Asp Asp Gly
                325                 330                 335

Asp Asp Gly Asp Asp Asp Gln Phe Ala Lys Lys Gly Lys Ser Ser Leu
            340                 345                 350

Ser Leu Asn Phe Asn Pro
        355

<210> SEQ ID NO 55
<211> LENGTH: 735
<212> TYPE: DNA
<213> ORGANISM: Arabidopsis thaliana

<400> SEQUENCE: 55
atgtcaataa accaatactc aagcgatttc cactaccatt ctctcatgtg gcaacaacag      60
cagcaacaac aacaacacca aaacgacgtc gtggaagaaa aagaagctct tttcgagaaa     120
cccttaaccc caagtgacgt cggaaaactc aaccgcctcg tcatcccaaa acagcacgcc     180
gagagatact tcccactagc ggccgccgcc gcagacgccg tggagaaagg acttctcctc     240
tgctttgagg acgaggaagg taaaccatgg agattcagat actcgtactg gaacagtagc     300
cagagttatg tcttgaccaa aggctggagc agatacgtca aggagaagca ccttgacgcc     360
ggagacgtcg ttctcttcca tcgacaccgt tcagacggcg gaagattctt cattggctgg     420
agaagacgcg gtgactcttc ttcctcctcc gactcttatc gccatgttca atccaatgcc     480
tcgctccaat attatcctca tgcaggggct caagcggtgg agagccaaag aggcaactcg     540
aagacattaa gactgttcgg agtgaacatg gagtgccagc tagattcgga ctggtccgag     600
ccatccacac ctgacggttc taacacatat acaaccaatc acgaccagtt tcatttctac     660
cctcaacaac aacactatcc tcctccgtac tacatggaca taagtttcac aggagatatg     720
aaccggacga gctag                                                      735

<210> SEQ ID NO 56
<211> LENGTH: 244
<212> TYPE: PRT
<213> ORGANISM: Arabidopsis thaliana

<400> SEQUENCE: 56

Met Ser Ile Asn Gln Tyr Ser Ser Asp Phe His Tyr His Ser Leu Met
1               5                   10                  15

Trp Gln Gln Gln Gln Gln Gln Gln His Gln Asn Asp Val Val Glu
            20                  25                  30

Glu Lys Glu Ala Leu Phe Glu Lys Pro Leu Thr Pro Ser Asp Val Gly
            35                  40                  45

Lys Leu Asn Arg Leu Val Ile Pro Lys Gln His Ala Glu Arg Tyr Phe
        50                  55                  60
```

```
Pro Leu Ala Ala Ala Ala Asp Ala Val Glu Lys Gly Leu Leu Leu
 65                  70                  75                  80

Cys Phe Glu Asp Glu Glu Gly Lys Pro Trp Arg Phe Arg Tyr Ser Tyr
                 85                  90                  95

Trp Asn Ser Ser Gln Ser Tyr Val Leu Thr Lys Gly Trp Ser Arg Tyr
            100                 105                 110

Val Lys Glu Lys His Leu Asp Ala Gly Asp Val Val Leu Phe His Arg
        115                 120                 125

His Arg Ser Asp Gly Gly Arg Phe Phe Ile Gly Trp Arg Arg Arg Gly
    130                 135                 140

Asp Ser Ser Ser Ser Ser Asp Ser Tyr Arg His Val Gln Ser Asn Ala
145                 150                 155                 160

Ser Leu Gln Tyr Tyr Pro His Ala Gly Ala Gln Ala Val Glu Ser Gln
                165                 170                 175

Arg Gly Asn Ser Lys Thr Leu Arg Leu Phe Gly Val Asn Met Glu Cys
            180                 185                 190

Gln Leu Asp Ser Asp Trp Ser Glu Pro Ser Thr Pro Asp Gly Ser Asn
        195                 200                 205

Thr Tyr Thr Thr Asn His Asp Gln Phe His Phe Tyr Pro Gln Gln Gln
    210                 215                 220

His Tyr Pro Pro Pro Tyr Tyr Met Asp Ile Ser Phe Thr Gly Asp Met
225                 230                 235                 240

Asn Arg Thr Ser

<210> SEQ ID NO 57
<211> LENGTH: 1014
<212> TYPE: DNA
<213> ORGANISM: Arabidopsis thaliana

<400> SEQUENCE: 57
atgagacttg atgacgaacc agaaaacgcc ctagtggttt cgtcttcacc aaagacggtt      60
gtggcttctg gcaatgtcaa gtacaaagga gtcgttcagc aacagaacgg tcattggggt     120
gcccagattt acgcagacca caaaggatt tggcttggaa ctttcaaatc cgctgatgaa      180
gccgccacgg cttacgatag tgcatctatc aaactccgaa gctttgacgc taactcgcac     240
cggaacttcc cttggtctac aatcactctc aacgaaccag actttcaaaa ttgctacaca     300
acagagactg tgttgaacat gatcagagac ggttcgtacc aacacaaatt cagagatttt     360
ctcagaatca gatctcagat tgttgcgagt atcaacatcg ggggaccaaa acaagcccga     420
ggagaagtga atcaagaatc agacaagtgt tttcttgca cacagctttt tcagaaggaa      480
ttgacaccga gcgatgtagg gaaactaaat aggcttgtga tacctaaaaa gtatgcagtg     540
aagtatatgc ctttcataag cgctgatcaa agcgagaaag aagagggtga atagtagga     600 tctgtggaag atgtggaggt tgtgttttac gacagagcaa tgagacaatg gaagtttagg     660
tattgttact ggaaaagtag ccagagcttt gtcttcacca gaggatggaa tagtttcgtg     720
aaggagaaga atctcaagga gaaggatgtt attgccttct acacttgcga tgtcccgaac     780
aatgtgaaga cattagaagg tcaaagaaag aacttcttga tgatcgatgt tcattgcttt     840
tcagacaacg gttccgtggt agctgaggaa gtaagtatga cggttcatga cagttcagtg     900
caagtaaaga aaacagaaaa cttggttagc tccatgttag aagataaaga aaccaaatca     960
gaggagaaca aaggagggtt tatgctgttt ggtgtaagga tcgaatgtcc ttag          1014

<210> SEQ ID NO 58
```

<211> LENGTH: 337
<212> TYPE: PRT
<213> ORGANISM: Arabidopsis thaliana

<400> SEQUENCE: 58

Met Arg Leu Asp Asp Glu Pro Glu Asn Ala Leu Val Val Ser Ser Ser
1               5                   10                  15
Pro Lys Thr Val Val Ala Ser Gly Asn Val Lys Tyr Lys Gly Val Val
            20                  25                  30
Gln Gln Gln Asn Gly His Trp Gly Ala Gln Ile Tyr Ala Asp His Lys
        35                  40                  45
Arg Ile Trp Leu Gly Thr Phe Lys Ser Ala Asp Glu Ala Ala Thr Ala
    50                  55                  60
Tyr Asp Ser Ala Ser Ile Lys Leu Arg Ser Phe Asp Ala Asn Ser His
65                  70                  75                  80
Arg Asn Phe Pro Trp Ser Thr Ile Thr Leu Asn Glu Pro Asp Phe Gln
                85                  90                  95
Asn Cys Tyr Thr Thr Glu Thr Val Leu Asn Met Ile Arg Asp Gly Ser
            100                 105                 110
Tyr Gln His Lys Phe Arg Asp Phe Leu Arg Ile Arg Ser Gln Ile Val
        115                 120                 125
Ala Ser Ile Asn Ile Gly Gly Pro Lys Gln Ala Arg Gly Glu Val Asn
    130                 135                 140
Gln Glu Ser Asp Lys Cys Phe Ser Cys Thr Gln Leu Phe Gln Lys Glu
145                 150                 155                 160
Leu Thr Pro Ser Asp Val Gly Lys Leu Asn Arg Leu Val Ile Pro Lys
                165                 170                 175
Lys Tyr Ala Val Lys Tyr Met Pro Phe Ile Ser Ala Asp Gln Ser Glu
            180                 185                 190
Lys Glu Glu Gly Glu Ile Val Gly Ser Val Glu Asp Val Glu Val Val
        195                 200                 205
Phe Tyr Asp Arg Ala Met Arg Gln Trp Lys Phe Arg Tyr Cys Tyr Trp
    210                 215                 220
Lys Ser Ser Gln Ser Phe Val Phe Thr Arg Gly Trp Asn Ser Phe Val
225                 230                 235                 240
Lys Glu Lys Asn Leu Lys Glu Lys Asp Val Ile Ala Phe Tyr Thr Cys
                245                 250                 255
Asp Val Pro Asn Asn Val Lys Thr Leu Glu Gly Gln Arg Lys Asn Phe
            260                 265                 270
Leu Met Ile Asp Val His Cys Phe Ser Asp Asn Gly Ser Val Val Ala
        275                 280                 285
Glu Glu Val Ser Met Thr Val His Asp Ser Ser Val Gln Val Lys Lys
    290                 295                 300
Thr Glu Asn Leu Val Ser Ser Met Leu Glu Asp Lys Glu Thr Lys Ser
305                 310                 315                 320
Glu Glu Asn Lys Gly Gly Phe Met Leu Phe Gly Val Arg Ile Glu Cys
                325                 330                 335
Pro

<210> SEQ ID NO 59
<211> LENGTH: 900
<212> TYPE: DNA
<213> ORGANISM: Arabidopsis thaliana

<400> SEQUENCE: 59

```
atgaatcaag aagataaaga gaagcctatt gaagaagctt cttcatcaat ggagagagaa      60
cacatgttcg acaaagtagt aacaccaagc gacgttggca aactaaaccg actcgtgatc     120
cctaagcaac acgcagagag atacttccca ttagataact ccacaacaaa cgacagcaac     180
aaaggtttgc ttctaaactt cgaagatcga agtggaaact catggaggtt ccgttactct     240
tactggaaca gtagtcaaag ctatgtcatg actaaaggtt ggagccgttt tgtcaaagac     300
aagaagcttg atgctggaga catcgttcct tttcagagag attcttgtaa taaagacaag     360
ctttacatcg attggaggag acgacctaag attcccgatc atcatcatca gcaattcgcc     420
ggagctatgt tccctaggtt ttacactttt cctcatcctc agatgccgac aaattacgaa     480
actcacaacc tttatcatcg atttcatcaa cgagatctag aattggata ctatgtgagg      540 tcaatggaga ggagtcatcc aacggctgtg attgaatctg tgccggtgat gatgcaaagg     600
agagcacaag tggcttcaat ggcttcgaga ggagagaagc ggttaaggct gtttggtgta     660
gatatggagt gcggaggagg aggagggagt gtgaatagta cggaggaaga gtcgtcgtct     720
tccggtggta gtataccacg tggcagagtt tctatggttg gtgctggttc tctcctccag     780
ttgaggttag tgagcagtga tgatgagtct ttagtagcaa tggaagctgc aagtcttgag     840
gatcatcact tctttacaaa gaaaggaaaa ccttctttgt cttttgattt ggataggtga     900
```

```
<210> SEQ ID NO 60
<211> LENGTH: 299
<212> TYPE: PRT
<213> ORGANISM: Arabidopsis thaliana

<400> SEQUENCE: 60
```

```
Met Asn Gln Glu Asp Lys Glu Lys Pro Ile Glu Glu Ala Ser Ser
1               5                   10                  15

Met Glu Arg Glu His Met Phe Asp Lys Val Val Thr Pro Ser Asp Val
            20                  25                  30

Gly Lys Leu Asn Arg Leu Val Ile Pro Lys Gln His Ala Glu Arg Tyr
        35                  40                  45

Phe Pro Leu Asp Asn Ser Thr Thr Asn Asp Ser Asn Lys Gly Leu Leu
    50                  55                  60

Leu Asn Phe Glu Asp Arg Ser Gly Asn Ser Trp Arg Phe Arg Tyr Ser
65                  70                  75                  80

Tyr Trp Asn Ser Ser Gln Ser Tyr Val Met Thr Lys Gly Trp Ser Arg
                85                  90                  95

Phe Val Lys Asp Lys Lys Leu Asp Ala Gly Asp Ile Val Ser Phe Gln
            100                 105                 110

Arg Asp Ser Cys Asn Lys Asp Lys Leu Tyr Ile Asp Trp Arg Arg Arg
        115                 120                 125

Pro Lys Ile Pro Asp His His His Gln Gln Phe Ala Gly Ala Met Phe
    130                 135                 140

Pro Arg Phe Tyr Thr Phe Pro His Pro Gln Met Pro Thr Asn Tyr Glu
145                 150                 155                 160

Thr His Asn Leu Tyr His Arg Phe His Gln Arg Asp Leu Gly Ile Gly
                165                 170                 175

Tyr Tyr Val Arg Ser Met Glu Arg Ser His Pro Thr Ala Val Ile Glu
            180                 185                 190

Ser Val Pro Val Met Met Gln Arg Arg Ala Gln Val Ala Ser Met Ala
        195                 200                 205

Ser Arg Gly Glu Lys Arg Leu Arg Leu Phe Gly Val Asp Met Glu Cys
    210                 215                 220
```

Gly Gly Gly Gly Gly Ser Val Asn Ser Thr Glu Glu Ser Ser Ser
225                 230                 235                 240

Ser Gly Gly Ser Ile Pro Arg Gly Arg Val Ser Met Val Gly Ala Gly
            245                 250                 255

Ser Leu Leu Gln Leu Arg Leu Val Ser Ser Asp Asp Glu Ser Leu Val
            260                 265                 270

Ala Met Glu Ala Ala Ser Leu Glu Asp His His Phe Phe Thr Lys Lys
            275                 280                 285

Gly Lys Pro Ser Leu Ser Phe Asp Leu Asp Arg
        290                 295

<210> SEQ ID NO 61
<211> LENGTH: 849
<212> TYPE: DNA
<213> ORGANISM: Arabidopsis thaliana

<400> SEQUENCE: 61
atgtcagtca accattactc cacagaccac caccacactc tcttgtggca gcaacagcaa      60
caccgccaca ccaccgacac atcggagaca accaccaccg ccacatggct ccacgacgac     120
ctaaaagagt cactcttcga gaagtctctc acaccaagcg acgtcgggaa actcaaccgc     180
ctcgtcatac aaaacaaca cgcagagaaa tacttccctc tcaatgccgt cctagtctcc      240
tctgctgctg ctgacacgtc atcttcggag aaagggatgc ttctaagctt tgaagacgag     300
tcaggcaagt catggaggtt cagatactct tactggaaca gcagtcaaag ctatgtcttg     360
actaaaggat ggagcagatt tgtcaaagac aaacagctcg atccaggcga cgttgttttc     420
ttccaacgac accgttctga ttctaggaga ctcttcattg ctggcgcag acgtggacaa      480
ggctcctcat cctccgtcgc ggccactaac tccgccgtga atacgagttc tatgggagct     540
cttctctatc atcaaatcca cgccactagt aattactcta atcctccctc tcactcagag     600
tattcccact atggagccgc cgtagcaaca gcggctgaga ctcacagcac accgtcgtct     660
tccgtcgtcg ggagctcaag gacggtgagg cttttcggtg tgaatctgga gtgtcaaatg     720
gatgaaaacg acggagatga ttctgttgca gttgccacca ccgttgaatc tcccgacggt     780
tactacggcc aaaacatgta ctattattac tctcatcctc ataacatggt aattttaact     840
ctttttataa                                                           849

<210> SEQ ID NO 62
<211> LENGTH: 282
<212> TYPE: PRT
<213> ORGANISM: Arabidopsis thaliana

<400> SEQUENCE: 62

Met Ser Val Asn His Tyr Ser Thr Asp His His Thr Leu Leu Trp
1               5                   10                  15

Gln Gln Gln Gln His Arg His Thr Thr Asp Thr Ser Glu Thr Thr Thr
            20                  25                  30

Thr Ala Thr Trp Leu His Asp Asp Leu Lys Glu Ser Leu Phe Glu Lys
        35                  40                  45

Ser Leu Thr Pro Ser Asp Val Gly Lys Leu Asn Arg Leu Val Ile Pro
    50                  55                  60

Lys Gln His Ala Glu Lys Tyr Phe Pro Leu Asn Ala Val Leu Val Ser
65                  70                  75                  80

Ser Ala Ala Ala Asp Thr Ser Ser Ser Glu Lys Gly Met Leu Leu Ser
            85                  90                  95

Phe Glu Asp Glu Ser Gly Lys Ser Trp Arg Phe Arg Tyr Ser Tyr Trp
            100                 105                 110

Asn Ser Ser Gln Ser Tyr Val Leu Thr Lys Gly Trp Ser Arg Phe Val
            115                 120                 125

Lys Asp Lys Gln Leu Asp Pro Gly Asp Val Val Phe Phe Gln Arg His
130                 135                 140

Arg Ser Asp Ser Arg Arg Leu Phe Ile Gly Trp Arg Arg Gly Gln
145                 150                 155                 160

Gly Ser Ser Ser Ser Val Ala Ala Thr Asn Ser Ala Val Asn Thr Ser
            165                 170                 175

Ser Met Gly Ala Leu Ser Tyr His Gln Ile His Ala Thr Ser Asn Tyr
            180                 185                 190

Ser Asn Pro Pro Ser His Ser Glu Tyr Ser His Tyr Gly Ala Ala Val
            195                 200                 205

Ala Thr Ala Ala Glu Thr His Ser Thr Pro Ser Ser Val Val Gly
            210                 215                 220

Ser Ser Arg Thr Val Arg Leu Phe Gly Val Asn Leu Glu Cys Gln Met
225                 230                 235                 240

Asp Glu Asn Asp Gly Asp Asp Ser Val Ala Val Ala Thr Thr Val Glu
                245                 250                 255

Ser Pro Asp Gly Tyr Tyr Gly Gln Asn Met Tyr Tyr Tyr Ser His
            260                 265                 270

Pro His Asn Met Val Ile Leu Thr Leu Leu
            275                 280

<210> SEQ ID NO 63
<211> LENGTH: 804
<212> TYPE: DNA
<213> ORGANISM: Arabidopsis thaliana

<400> SEQUENCE: 63
atgtcagtca accattacca caacactctc tcgttgcatc atcaccacca aaacgacgta      60
gctatagcac aacgagagtc tttgttcgag aaatcactca caccaagcga cgtcggaaag     120
ctaaaccgct tagtcatacc aaaacaacac gccgagaaat acttccctct caataataat     180
aataataatg gcggcagcgg agatgacgtg gcgacgacgg agaaagggat gcttcttagc     240
ttcgaggatg agtcaggcaa gtgttggaaa ttcagatact cttattggaa cagtagccaa     300
agctacgtgt tgaccaaagg atggagcagg tacgtcaaag acaaacacct cgacgcaggc     360
gacgttgttt tctttcaacg tcaccgtttt gatctccata gactcttcat tggctggcgg     420
agacgcggtg aagcttcttc ctctcccgct gtctccgttg tgtctcaaga gctctagtt     480 aatacgacgg cgtattggag cggcttgact acaccttatc gtcaagtaca cgcgtcaact     540
acttacccta atattcacca agagtattca cactatggcg ccgtcgttga tcatgctcag     600
tcgataccac cggtggtcgc aggtagctcg aggacggtga ggcttttgg cgtgaacctc     660 gaatgtcatg gtgatgccgt cgagccacca ccgcgtcctg atgtctataa tgaccaacac     720
atttactatt actcaactcc tcatcccatg aatatatcat ttgctgggga agcattggag     780
caggtaggag atggacgagg ttga                                            804

<210> SEQ ID NO 64
<211> LENGTH: 267
<212> TYPE: PRT
<213> ORGANISM: Arabidopsis thaliana

<400> SEQUENCE: 64

```
Met Ser Val Asn His Tyr His Asn Thr Leu Ser Leu His His His
1               5                   10                  15
Gln Asn Asp Val Ala Ile Ala Gln Arg Glu Ser Leu Phe Glu Lys Ser
            20                  25                  30
Leu Thr Pro Ser Asp Val Gly Lys Leu Asn Arg Leu Val Ile Pro Lys
        35                  40                  45
Gln His Ala Glu Lys Tyr Phe Pro Leu Asn Asn Asn Asn Asn Gly
    50                  55                  60
Gly Ser Gly Asp Asp Val Ala Thr Thr Glu Lys Gly Met Leu Leu Ser
65                  70                  75                  80
Phe Glu Asp Glu Ser Gly Lys Cys Trp Lys Phe Arg Tyr Ser Tyr Trp
                85                  90                  95
Asn Ser Ser Gln Ser Tyr Val Leu Thr Lys Gly Trp Ser Arg Tyr Val
            100                 105                 110
Lys Asp Lys His Leu Asp Ala Gly Asp Val Val Phe Phe Gln Arg His
        115                 120                 125
Arg Phe Asp Leu His Arg Leu Phe Ile Gly Trp Arg Arg Gly Glu
    130                 135                 140
Ala Ser Ser Ser Pro Ala Val Ser Val Val Ser Gln Glu Ala Leu Val
145                 150                 155                 160
Asn Thr Thr Ala Tyr Trp Ser Gly Leu Thr Thr Pro Tyr Arg Gln Val
                165                 170                 175
His Ala Ser Thr Thr Tyr Pro Asn Ile His Gln Glu Tyr Ser His Tyr
            180                 185                 190
Gly Ala Val Val Asp His Ala Gln Ser Ile Pro Pro Val Val Ala Gly
        195                 200                 205
Ser Ser Arg Thr Val Arg Leu Phe Gly Val Asn Leu Glu Cys His Gly
    210                 215                 220
Asp Ala Val Glu Pro Pro Arg Pro Asp Val Tyr Asn Asp Gln His
225                 230                 235                 240
Ile Tyr Tyr Tyr Ser Thr Pro His Pro Met Asn Ile Ser Phe Ala Gly
                245                 250                 255
Glu Ala Leu Glu Gln Val Gly Asp Gly Arg Gly
            260                 265
```

<210> SEQ ID NO 65
<211> LENGTH: 2082
<212> TYPE: DNA
<213> ORGANISM: Arabidopsis thaliana

<400> SEQUENCE: 65

```
atggagcaag agaaaagctt ggatccacaa ctatggcatg cttgtgcagg atcaatggtt      60
caaatccctt cactgaattc aacgtttttt tacttcgctc aaggccacac agagcacgct     120
cacgcgcctc ctgattttca cgcgccgcgc gttccacctc ttatcctctg tcgtgtcgtc     180
tccgtgaagt tcctcgccga cgctgaaaca gacgaagttt ttgctaaaat tacgcttttg     240
ccacttccgg gaaacgactt ggatctagaa acgacgccg ttttgggtct aactcctcct     300
tcttctgacg gtaacggtaa cggtaaagag aaaccggcgt cttcgctaa acgttaacg      360
cagtctgacg ctaataacgg cggtggtttc tccgttccac gttattgcgc cgagacgatt     420
ttcccgcggc ttgattactc ggcggagcca ccggttcaaa ccgtgattgc taaagacatc     480
cacggcgaga cttggaaatt ccggcatatt tacagaggaa cacctcgccg tcatctccta     540
```

```
accaccggtt ggagcacttt cgttaaccag aagaaactaa tcgccggaga ctcaatcgtc     600
ttcctccgtt ctgaatccgg tgacctctgc gtcggaatcc gccgcgctaa acgcggcggt     660
ctcggatcta acgcaggatc cgacaatcct accctggat  tctccggttt cctccgtgac     720
gacgagtcaa caacaacaac atcgaagcta atgatgatga aacgcaacgg aaacaacgac     780
ggaaacgccg cggctacagg gagggttaga gtagaagcag tagcggaagc ggtggcgcgt     840
gcagcgtgtg gacaagcgtt tgaggttgtt tattatccac gcgctagtac accggagttt     900
tgcgtaaaag cagctgatgt tagatcagca atgaggataa gatggtgtag tggtatgcgt     960
tttaaaatgg cgtttgaaac agaggattct tctagaatca gttggtttat gggtactgtc    1020
tccgccgttc aagtcgctga tccaattcgt tggcctaatt caccatggcg tctccttcag    1080
gtagcttggg acgaaccgga tttgttacaa aacgttaagc gggttagtcc gtggttagtc    1140
gaattggtat cgaacatgcc tacaatacat ttatctccat tctctccgag gaagaagatt    1200
aggattccgc agccatttga gtttccattc cacggtacta aattcccgat tttctccccg    1260
ggattcgcca acaatggcgg tggcgagtcc atgtgttatc tgtcaaacga caacaataat    1320
gctcctgcag gaatacaggg agccaggcaa gctcaacaac tcttcggatc accatctccg    1380
tctttgttgt ctgatctcaa tcttagtagt tacaccggta caacaagtt  acattctccg    1440
gcgatgtttc tatcgagttt caacccgagg catcatcatt atcaggctag ggatagtgag    1500
aatagtaata acatttcgtg ttctttaact atggggaatc ctgctatggt tcaggataag    1560
aagaagtctg ttggttcggt taagactcat cagttcgtgt tgttcggtca accgattta     1620
accgaacagc aagttatgaa ccgaaaacgg tttttggaag aagaggcgga agcggaggag    1680
gagaaaggtt tagtggctcg tgggttaaca tggaattata gtttgcaagg acttgagacg    1740
ggtcattgta aagtttcat  ggaatctgag gatgttggac gcacactcga tctctcggtt    1800
attggctcgt accaagaatt gtaccggaaa ttggctgaga tgtttcatat agaagagagg    1860
tcggatttgt tgactcatgt tgtgtaccgg gatgcaaatg gtgttatcaa acgtattgga    1920
gacgaacctt tcagtgattt catgaaagca actaaacggc taacaatcaa gatggatatt    1980
ggtggcgaca acgtgagaaa gacgtggata accggaatca ggactggtga aaatggtata    2040
gacgcttcta cgaagactgg tccgctcagc atcttcgctt ga                       2082
```

<210> SEQ ID NO 66
<211> LENGTH: 693
<212> TYPE: PRT
<213> ORGANISM: Arabidopsis thaliana

<400> SEQUENCE: 66

```
Met Glu Gln Glu Lys Ser Leu Asp Pro Gln Leu Trp His Ala Cys Ala
1               5                   10                  15

Gly Ser Met Val Gln Ile Pro Ser Leu Asn Ser Thr Val Phe Tyr Phe
            20                  25                  30

Ala Gln Gly His Thr Glu His Ala His Ala Pro Pro Asp Phe His Ala
        35                  40                  45

Pro Arg Val Pro Pro Leu Ile Leu Cys Arg Val Ser Val Lys Phe
    50                  55                  60

Leu Ala Asp Ala Glu Thr Asp Glu Val Phe Ala Lys Ile Thr Leu Leu
65                  70                  75                  80

Pro Leu Pro Gly Asn Asp Leu Asp Leu Glu Asn Asp Ala Val Leu Gly
                85                  90                  95

Leu Thr Pro Pro Ser Ser Asp Gly Asn Gly Asn Gly Lys Glu Lys Pro
```

-continued

```
                    100                 105                 110
Ala Ser Phe Ala Lys Thr Leu Thr Gln Ser Asp Ala Asn Asn Gly Gly
                115                 120                 125
Gly Phe Ser Val Pro Arg Tyr Cys Ala Glu Thr Ile Phe Pro Arg Leu
            130                 135                 140
Asp Tyr Ser Ala Glu Pro Pro Val Gln Thr Val Ile Ala Lys Asp Ile
145                 150                 155                 160
His Gly Glu Thr Trp Lys Phe Arg His Ile Tyr Arg Gly Thr Pro Arg
                165                 170                 175
Arg His Leu Leu Thr Thr Gly Trp Ser Thr Phe Val Asn Gln Lys Lys
                180                 185                 190
Leu Ile Ala Gly Asp Ser Ile Val Phe Leu Arg Ser Glu Ser Gly Asp
                195                 200                 205
Leu Cys Val Gly Ile Arg Arg Ala Lys Arg Gly Gly Leu Gly Ser Asn
            210                 215                 220
Ala Gly Ser Asp Asn Pro Tyr Pro Gly Phe Ser Gly Phe Leu Arg Asp
225                 230                 235                 240
Asp Glu Ser Thr Thr Thr Thr Ser Lys Leu Met Met Met Lys Arg Asn
                245                 250                 255
Gly Asn Asn Asp Gly Asn Ala Ala Ala Thr Gly Arg Val Arg Val Glu
                260                 265                 270
Ala Val Ala Glu Ala Val Ala Arg Ala Ala Cys Gly Gln Ala Phe Glu
            275                 280                 285
Val Val Tyr Tyr Pro Arg Ala Ser Thr Pro Glu Phe Cys Val Lys Ala
            290                 295                 300
Ala Asp Val Arg Ser Ala Met Arg Ile Arg Trp Cys Ser Gly Met Arg
305                 310                 315                 320
Phe Lys Met Ala Phe Glu Thr Glu Asp Ser Ser Arg Ile Ser Trp Phe
                325                 330                 335
Met Gly Thr Val Ser Ala Val Gln Val Ala Asp Pro Ile Arg Trp Pro
            340                 345                 350
Asn Ser Pro Trp Arg Leu Leu Gln Val Ala Trp Asp Glu Pro Asp Leu
        355                 360                 365
Leu Gln Asn Val Lys Arg Val Ser Pro Trp Leu Val Glu Leu Val Ser
    370                 375                 380
Asn Met Pro Thr Ile His Leu Ser Pro Phe Ser Pro Arg Lys Lys Ile
385                 390                 395                 400
Arg Ile Pro Gln Pro Phe Glu Phe Pro Phe His Gly Thr Lys Phe Pro
                405                 410                 415
Ile Phe Ser Pro Gly Phe Ala Asn Asn Gly Gly Glu Ser Met Cys
                420                 425                 430
Tyr Leu Ser Asn Asp Asn Asn Ala Pro Ala Gly Ile Gln Gly Ala
            435                 440                 445
Arg Gln Ala Gln Gln Leu Phe Gly Ser Pro Ser Pro Ser Leu Leu Ser
        450                 455                 460
Asp Leu Asn Leu Ser Ser Tyr Thr Gly Asn Asn Lys Leu His Ser Pro
465                 470                 475                 480
Ala Met Phe Leu Ser Ser Phe Asn Pro Arg His His Tyr Gln Ala
                485                 490                 495
Arg Asp Ser Glu Asn Ser Asn Asn Ile Ser Cys Ser Leu Thr Met Gly
            500                 505                 510
Asn Pro Ala Met Val Gln Asp Lys Lys Ser Val Gly Ser Val Lys
        515                 520                 525
```

```
Thr His Gln Phe Val Leu Phe Gly Gln Pro Ile Leu Thr Glu Gln Gln
    530                 535                 540

Val Met Asn Arg Lys Arg Phe Leu Glu Glu Glu Ala Glu Ala Glu Glu
545                 550                 555                 560

Glu Lys Gly Leu Val Ala Arg Gly Leu Thr Trp Asn Tyr Ser Leu Gln
                565                 570                 575

Gly Leu Glu Thr Gly His Cys Lys Val Phe Met Glu Ser Glu Asp Val
            580                 585                 590

Gly Arg Thr Leu Asp Leu Ser Val Ile Gly Ser Tyr Gln Glu Leu Tyr
        595                 600                 605

Arg Lys Leu Ala Glu Met Phe His Ile Glu Glu Arg Ser Asp Leu Leu
    610                 615                 620

Thr His Val Val Tyr Arg Asp Ala Asn Gly Val Ile Lys Arg Ile Gly
625                 630                 635                 640

Asp Glu Pro Phe Ser Asp Phe Met Lys Ala Thr Lys Arg Leu Thr Ile
                645                 650                 655

Lys Met Asp Ile Gly Gly Asp Asn Val Arg Lys Thr Trp Ile Thr Gly
            660                 665                 670

Ile Arg Thr Gly Glu Asn Gly Ile Asp Ala Ser Thr Lys Thr Gly Pro
        675                 680                 685

Leu Ser Ile Phe Ala
    690
```

<210> SEQ ID NO 67
<211> LENGTH: 35
<212> TYPE: DNA
<213> ORGANISM: Arabidopsis thaliana

<400> SEQUENCE: 67
cccaagcttg gatccaaagg gtctgattcg tttgt                    35

<210> SEQ ID NO 68
<211> LENGTH: 35
<212> TYPE: DNA
<213> ORGANISM: Arabidopsis thaliana

<400> SEQUENCE: 68
cggggtaccg ttaacgtcac atcttctcta tagct                    35

<210> SEQ ID NO 69
<211> LENGTH: 35
<212> TYPE: DNA
<213> ORGANISM: Arabidopsis thaliana

<400> SEQUENCE: 69
cccaagcttg gatcccccaa acgaagaacc aaaca                    35

<210> SEQ ID NO 70
<211> LENGTH: 35
<212> TYPE: DNA
<213> ORGANISM: Arabidopsis thaliana

<400> SEQUENCE: 70
cggggtaccg atatcttctt caaaattggt aactc                    35

<210> SEQ ID NO 71
<211> LENGTH: 35
<212> TYPE: DNA
<213> ORGANISM: Arabidopsis thaliana -continued

```
<400> SEQUENCE: 71
ccgctcgagg gatccgaagc ttgatcctcc tagtt                              35

<210> SEQ ID NO 72
<211> LENGTH: 35
<212> TYPE: DNA
<213> ORGANISM: Arabidopsis thaliana

<400> SEQUENCE: 72
cggggtaccg atatcagata caagataaat tcact                              35

<210> SEQ ID NO 73
<211> LENGTH: 35
<212> TYPE: DNA
<213> ORGANISM: Arabidopsis thaliana

<400> SEQUENCE: 73
cccaagcttg gatccgaaca agggttttag ggctt                              35

<210> SEQ ID NO 74
<211> LENGTH: 35
<212> TYPE: DNA
<213> ORGANISM: Arabidopsis thaliana

<400> SEQUENCE: 74
cggggtaccg atatcgttgc cactcttaag taata                              35

<210> SEQ ID NO 75
<211> LENGTH: 35
<212> TYPE: DNA
<213> ORGANISM: Arabidopsis thaliana

<400> SEQUENCE: 75
cccactagtg gatccatgga ttctcagagg ggtat                              35

<210> SEQ ID NO 76
<211> LENGTH: 35
<212> TYPE: DNA
<213> ORGANISM: Arabidopsis thaliana

<400> SEQUENCE: 76
cggggtaccg atatctcaga aaggagccga gcttg                              35

<210> SEQ ID NO 77
<211> LENGTH: 35
<212> TYPE: DNA
<213> ORGANISM: Arabidopsis thaliana

<400> SEQUENCE: 77
cccggtaccg gatccacagt ttctaaggca aaata                              35

<210> SEQ ID NO 78
<211> LENGTH: 35
<212> TYPE: DNA
<213> ORGANISM: Arabidopsis thaliana

<400> SEQUENCE: 78
cggaggcctg aattcacttg aactagtgtt tgtac                              35
```

TRANSCRIPTION FACTORS, DNA AND METHODS FOR INTRODUCTION OF VALUE-ADDED SEED TRAITS AND STRESS TOLERANCE

CROSS-REFERENCE TO RELATED APPLICATION

This is a continuation-in-part of pending U.S. application Ser. No. 10/629,907, filed Jul. 30, 2003, which is based upon Provisional Application No. 60/399,565 filed Jul. 30, 2002, both of which are incorporated fully herein by reference

BACKGROUND OF THE INVENTION

1. Field of the Invention

A variety of stress-related traits in plants are enhanced by the synergistic effects on abscisic acid (ABA)-inducible gene expression of co-expressed basic leucine zipper (bZIP)-domain transcription factors and B3-domain transcription factors. Additionally, two different B3-domain transcription factors may be used to synergistically regulate ABA-inducible gene expression.

2. Description of Related Art

The growth in the world's population combined with a general increase in global prosperity is creating an increasing demand for food, fiber and sustainable agriculture. It is estimated that the world's population will increase by 80% to 10.8 billion people by 2050, with a concomitant decrease in arable land of 20%. A worthwhile future can only be guaranteed through sustainable agriculture and a protective relationship with nature. For example, rice is the staple food for two-thirds of the world's population and is the primary cereal crop in the world, with worldwide production in 2000 of 600 million tons. 92% of the world's rice is produced in Asia, and 40% of the cultivated area is rain-fed and experiences environmental stress, with losses estimated at 200 million tons/yr. Another example is impacts of drought on maize production in the southwest United States. Based on data from the USDA National Agricultural Statistics Service (http://www.usda.gov/nass/), in 2003 the geographical region spanning southern CA, AZ, NM, TX High Plains and trans-Pecos regions produced 1.2% (127 mil bushels) of the nation's grain corn, valued at >$310 million. It is noteworthy that only 78% of grain corn planted in these regions of the Southwest were subsequently harvested, whereas on average 90% of the planted acreage was harvested throughout the United States. Significantly, for AZ and NM from 1999-2003, the percentages of grain corn harvested ranged from only 35-58%, while the national average over that time period was 90.2%. The basis for these differences between the southwest and the "Corn Belt" harvests, valued at >$48 million in losses last year alone, is due to reductions in yield due to drought stress typically experienced by crops in the southwest. Genetic engineering of maize for increased vegetative drought stress adaptation should result in increased yields and profits for producers. A third example is dryland cotton; estimates of the value-added worth of cotton with increased photosynthetic and water use efficiencies and improved seed qualities exceed $200 million/yr in west Texas, $1 billion/yr in the USA, and $5 billion/yr globally.

Yield enhancement to increase crop production is one of the essential strategies to meet the demand for food by the growing population. In order to supply the world's population in 20 years' time with enough to eat, today's food production will have to be doubled on a third less land and water. For example, due to traditional rice breeding advances, with which germplasm from wild relatives was transferred to cultivated strains, production of rice doubled between 1966 and 1990, but it is estimated that production must increase 60% by 2025 to meet demand. The rate at which growers have been able to further improve crop productivity has declined as improved farming practices have become more fully implemented around the world, as land in developed countries available for conversion to farming has declined, and as concerns about the environmental impact of farming have increased.

While the rate of yield increases from hybrids has slowed in the last two decades, the application of biotechnology and genomics is dramatically increasing innovation in the agricultural and seed industries. Biotechnology as a means of sustainable agriculture is a crucial component to meeting the challenges posed by the interrelated global issues of poverty, hunger, population growth, and environmental degradation in the twenty-first century. Biotechnology enables gene-by-gene analysis and enhancement of crops and is augmenting traditional breeding by enabling faster, targeted development of performance-enhancing traits. These traits currently are designed to create higher-quality animal feed and in the future are expected to include nutritional benefits for humans.

Growers have rapidly adopted the first generation of genetically engineered seed traits, with significant numbers of acres planted. The number of global planted acres of herbicide-tolerant and insect-resistant crops grew from less than 5 million acres in 1995 to approximately 120 million acres in 1999. Despite this rapid growth, the total number of acres covered currently represents only a small fraction of the approximately 3 billion acres of crops cultivated worldwide. Additional growth will come from further adoption of currently available traits and the development of new input and output traits.

Improvement of crop plants for a variety of traits, including disease and pest resistance, adaptation to abiotic stresses, and grain quality improvements such as oil, starch or protein composition, has been achieved by introducing new or modified genes into plant genomes. It has recently been shown that the "Green Revolution" of the 1960s that resulted in large increases in wheat yields was due to adoption of varieties that contain a dominant allele of a gene that controls transcription factor expression by modulating microRNAs, a newly discovered mechanism of gene regulation in mesozoans. Transcription factors control virtually all significant plant traits, including yield, disease resistance, freezing and drought protection, as well as the production of chemicals and proteins used as pharmaceuticals, nutriceuticals and consumer products, by coordinate regulation of multiple target genes whose functions in many cases are not yet known.

The expression of target transgenes and endogenous genes is controlled through a complex set of protein/DNA and protein/protein interactions. Promoters and enhancers can impart patterns of expression that are either constitutive or limited to specific tissues or times during development, or in response to environmental stimuli. There are limitations in the types of expression achievable using existing promoters for transgene expression. One limitation is in the expression level achievable. It is difficult to obtain traits that require relatively high expression of an introduced gene, due to limitations in promoter strength. A second limitation is that the pattern of expression conferred by the particular promoter employed is inflexible in that the same promoter-dependent pattern of expression is conferred from generation to generation. It is desirable to have the ability to regulate trait-conferring transgene expression differently in successive generations. One example would be a trait that has a side effect of being detrimental to seed quality, but which is desired for use in fodder. In this case, it would be desirable to carry the trait-conferring transgene in an inactive state in separate breeding stocks.

Plants are sessile and therefore must perpetually develop in response to their changing environment. Plants have evolved complex, integrated, and overlapping signaling pathways to maintain a plastic growth habit in response to stresses such as drought, salt, cold, as well as hormonal cues such as abscisic acid (ABA). ABA mediates a myriad of physiological processes in growth and development, including cell division, water use efficiency, and gene expression during seed development and in response to environmental stresses such as drought, chilling, salt, pathogen attack, and UV light. Despite the complex multitude of physiological, molecular, genetic, biochemical, and pharmacological data that implicate ABA in stress responses, the adaptive responses to ABA and stresses, and the pathways that trigger them, are largely unknown. Seed maturation and freezing/drought/salt tolerance may have certain protective mechanisms in common, since they share the common phenomenon of dehydration stress.

It would be advantageous for genetic engineering of plants with environmental stress resistance to regulate multiple genes in a particular metabolic or response pathway via a single transgene. Cloning and overexpression of Drought Response Element Binding (DREB)/Cold Binding Factor (CBF) subfamily of the AP2-domain family of transcription factors responsible for cold-inducible gene expression has demonstrated the practical benefits of coordinated activation of uncharacterized gene sets that can confer non-specific protection to transgenic plants by up-regulation or pre-activation of stress-response pathways. The ABA-INSENSITIVE-4 gene (ABI4) is most closely related to the DREB/CBF subfamily of the AP2-domain family. Transgenic overexpression of the transcription factor ALFIN1 enhances expression of the endogenous MsPRP2 gene in alfalfa and improves salinity tolerance of the plants. Over-expression of a single $Ca^{2+}$-dependent protein kinase confers both cold and salt/drought tolerance on rice plants. A multi-component transcription factor/target promoter system that regulates hormone and stress responses could be used to address the limitations of single transgene expression and tap into the natural defense systems of crop plants.

Although hundreds of ABA-regulated genes have been identified to date, many of them homologs from a broad range of species, these are likely to represent a somewhat anecdotal sampling of the full spectrum of ABA-responsive genes. Preliminary genome profiling in *Arabidopsis* has allowed estimation of the number of plant genes modulated by ABA, with current estimates at about 2000-6000 genes. A number of plant gene products have been identified that may function in desiccation tolerance. The COR genes are cold-, drought-, salt-, and ABA-responsive genes whose protein products are heat stable and hydrophilic; some COR genes have structural similarities to the late embryogenesis-abundant (LEA) proteins. LEA homologues in wheat, maize, barley, carrot, and the resurrection plant *Craterostigma plantagineum* are induced by ABA and dehydration stress. The exact roles of COR and LEA genes in cold and desiccation tolerance are not yet known, but there is strong evidence that they have an adaptive function in desiccation, freezing, and salt tolerance. Altered expression of ABA signal transduction genes can have beneficial effects on stress adaptation of plants.

The RY-G-box-RY regulatory element is commonly found in seed storage protein gene promoters and is necessary for seed-specific expression of the β-phaseolin and Em promoters. The sequences of the RY-G-box-RY elements that are found in different natural promoters have variations, but can be recognized by the presence of particular nucleotide sequences: CATGCAW (the "RY" feature) and CACGTG (the "G-box"). There is substantial diversity in the cis sequences shown to confer ABA-inducible expression. The smallest promoter units (called ABA-Response Elements; ABREs) that are both necessary and sufficient for ABA induction of gene expression appear to consist of at least two essential cis elements, one of which is usually a G-box and the other a "coupling" element.

A seed-specific regulatory factor, Viviparous-1 (VP1), was first described in 1931 and was cloned by transposon tagging in 1989. The ABA-INSENSITIVE3 (ABI3) gene of *Arabidopsis* is the genetic equivalent of maize VP1 and was cloned by chromosome walking. VP1/ABI3 is expressed in developing seeds and precedes ABA-inducible storage protein and late-embryogenesis-abundant (LEA) gene expression. Rice and maize protoplasts that transiently overexpress the VP1 cDNA can transactivate ABA-inducible promoters from numerous species. Similar transactivation results have been obtained in homologous transient gene expression systems with the rice VP1 and bean Pv-ALF orthologs. Remarkably, VP1 also has repressor activity towards the germination-specific alpha-amylase genes, but repression is non-cell-autonomous and requires embryo-specific factors other than ABA and VP1.

Structure/function studies with VP1 and PvALF in transient gene expression assays demonstrate that the highly conserved N-terminal acidic domain (A1, VP1 amino acids [aa] 51-163) functions as a transcriptional activator and acts in synergy with ABA. The acidic domain of VP1 is not required for germination-specific alpha-amylase gene repression. The conserved basic B2 region (aa 508-544 of VP1) is required for transactivation of the ABA-inducible Em promoter and for enhancing the in vitro binding of various basic leucine zipper (bZIP) factors to their cognate targets, but not for alpha-amylase gene repression. The B3 domain (aa 632-760) binds specifically to promoter sequences required for transactivation but not to ABA-responsive cis-elements. Furthermore, the B3 domain is not required for synergistic effects of transactivation with ABA or for alpha-amylase gene repression. Pv-ALF facilitates chromatin modification of the ABA-inducible β-Phas promoter, which in turn potentiates ABA-mediated transcription. Carrot and Arabidopsis Pv-ALF orthologs can also direct ABA-inducible seed storage protein expression in leaves when expressed ectopically. The exact molecular mechanisms of ABI3/VP1/Pv-ALF are not known, but the predicted FUS3 and LEAFY COTYLEDON-2 class of regulators that control embryo maturation have a continuous stretch of more than 100 amino acids showing significant sequence similarity to the conserved B3 domains of ABI3/VP1/Pv-ALF. Taken together with genetic results that show FUSCA3 and LEC2 interact with ABI3, these correlations suggest that ABI3, LEC2, and FUS3 may act in partially redundant pathways. The *Arabidopsis* genome encodes 43 members of the B3-domain family, 19 of them within the ABI3/VP1-related subfamily, and their functions are largely unknown.

There are 81 predicted bZIP factor genes in *Arabidopsis*, but only one bZIP subfamily has been genetically or functionally linked to ABA response: that composed of ABI5 and its homologs, including the ABRE Binding Factors (ABFs and AREBs), Enhanced Em Level (EEL/AtbZIP12), and AtbZIP13-15, 27, and 67, which include the AtDPBFs (*Arabidopsis thaliana* Dc3 Promoter Binding Factors). Homologs of these genes have been characterized in sunflower and rice, where they are also correlated with ABA-, seed- or stress-induced gene expression. However, studies of bZIPs from other species have shown that in vitro binding of ABREs need not reflect action in ABA signaling in vivo. A rice homolog of ABI5, TRAB1, was identified by a yeast two-hybrid screen using the basic domains of OsVP1 as "bait" and shown to interact with ABREs in vitro and activate ABA-inducible transcription in rice protoplasts. AREBs and ABFs both share with ABI5 three conserved charged domains (C1-C3) in their amino-halves as well as the bZIP domain and another conserved (C4) domain at the C-terminus. In vitro studies with the DPBFs and other ABI5-family members have demonstrated that this subfamily binds to G-box promoter elements (ABREs) required for ABA regulation. However, the ABI5/DPBF/ABF/AREB subfamily has a broader consensus sequence for its binding site than the other bZIP proteins in that its members tolerate variability in the ACGT core element essential to the ABRE G-box. ABI5 and its homolog DPBF4/EEL were shown to compete for the same binding sites in the AtEm1 promoter and a model was proposed, based on single and double mutant phenotypes of altered gene expression, that EEL directly antagonized ABI5 transactivation. Analyses of transcript accumulation in abi5 mutants suggest that, similar to ABI3, ABI5 has both activator and repressor functions, but that ABI5 and ABI3 may have either synergistic or antagonistic effects on gene expression, depending on the gene. ABI5 protein accumulation is further enhanced by ABA-induced phosphorylation and resulting stabilization of the protein, at least during the early phases of germination.

As indicated above, it has been previously shown that maize VP1 is functionally redundant with ABI3 and that other orthologues of VP1/ABI3 could substitute for VP1 in a multi-component heterologous transactivation system. Consistent with this, expression of an *Arabidopsis* GIBBERELLIN-INSENSITIVE (GAI) orthologue (the same gene responsible for the "Green Revolution" in wheat; see above) in transgenic rice resulted in desirable dwarfing traits, suggesting that heterologous regulatory genes can be used to affect traits in a wide range of crop species. Transgenic rice plants that express the maize phosphoenolpyruvate carboxylase (PEPC) and pyruvate orthophosphate dikinase (PPDK) exhibit a higher photosynthetic capacity (up to 35%) than untransformed plants, mainly associated with an enhanced stomatal conductance and a higher internal $CO_2$ concentration. An additional benefit of using heterologous genes is that they may minimize artifacts such as co-suppression and posttranscriptional transgene silencing.

Coordinated regulation of multiple endogenous genes is important for stress adaptation. New methods which genetically engineer value-added vegetative traits for stress adaptation and seed qualities by directed expression of ABA-related transcription factors would be beneficial to supply the world with the increased amounts of food needed by future generations. By overcoming the limitations of targeted gene expression and by transactivation of endogenous plant stress adaptation pathways, the volume and quality of plant products, especially from environments under stress, will be improved.

BRIEF SUMMARY OF THE INVENTION

Transgenic plants that ectopically express a B3-domain transcription factor, preferably VP1, ABI3, RAV2 and homologues from various species, in combination with at least one different B3-domain transcription factor or a bZIP-domain transcription factor, preferably ABI5 and ABI5-like family members ABF1 and ABF3 and homologues from various species, will respond to abiotic stressors such as salt, drought, and cold by activating ABA-inducible target promoters as well as endogenous promoters that coordinate expression of genes involved in stress adaptation, such as LEA and COR genes. In preferred embodiments, the B3-domain transcription factor and the bZIP-domain transcription factor are those found in members of the genus *Arabidopsis* and *Zea mays*. This multi-component expression system may be expanded by modifying the regulatory sequences of the target promoter or the promoter driving the transcription factor effectors to include tissue-specific enhancer elements or stress-response elements to further direct the expression of the target gene of interest. It is known in animal systems that targeting of some combinations of transcription factors to the same promoter may produce synergistic effects on the expression level. The strategy disclosed herein amplifies the expression level from an ABA-inducible promoter. For example, recent results have shown that grain-filling in rice is critically dependent on water status and ABA levels, suggesting that amplification of ABA response pathways by ectopic transcription factor expression in appropriate tissues and at critical times during development could have beneficial effects. The multi-component benefits of transcription factor synergy may be realized by genetic crossing of two lines harboring separate transcription factor components.

Abscisic acid (ABA) signaling pathways are highly conserved among monocots and dicots (See Gampala et al., *J. Biol. Chem.* 277: 1689 (2002)). Therefore, a multi-component transgenic approach to engineering stress tolerance with effectors from diverse plant species is practical. Evidence presented herein with overexpressed *Arabidopsis* bZIP domain transcription factors called ABFs, AREB3, DPBF4/EEL, ABI5 and maize B3 domain transcription factor VP1 in rice embryonic and maize mesophyll protoplasts further extends this claim. Since it has been shown that maize VP1 is functionally redundant with ABI3, other orthologues of VP1/ABI3 from various species could substitute for VP1 in a multi-component heterologous transactivation system. Further, evidence is presented herein that a VP1/ABI3-related B3 domain homologue from *Arabidopsis*, RAV2, functions in synergy with VP1 and the bZIPs ABI5 and ABF3 in maize mesophyll protoplasts, demonstrating a novel combinatorial phenomenon of synergy that extends the scope of this invention.

One potential drawback to overexpressing regulatory factors that confer stress tolerance to transgenic crops is reduced yields through pleiotropic "knock on" effects that indeed may be the direct consequence of stress adaptation mechanisms triggered by the transgene effector. In this scenario, the present invention would still find application in horticultural plants like turfgrasses where yields, per se, may be less important. Likewise, in ornamental species the slow-growth, stress-adapted phenotype would be a value-added trait.

Some novel activities of ABI5-like family members and ABI5 alone and in combination with maize VP1 have been demonstrated. Ectopic or controlled, e.g. inducible, expression of these and related effectors in any plant species should result in conditionally altered stress responses and higher levels of engineered target gene expression than otherwise possible. The present invention also relates to polynucleotides which contain the complete gene with the polynucleotide sequence corresponding to SEQ ID NO:.1, SEQ ID NO.:3, or SEQ ID NO: 5 or fragments thereof, and which can be obtained by screening by means of the hybridization of a corresponding gene bank with a probe which contains the sequence of said polynucleotide corresponding to SEQ ID NO:.1, SEQ ID NO.:3, or SEQ ID NO: 5 or a fragment thereof, and isolation of said DNA sequence.

Given the efficacy of ABA in regulating such basic processes as seed development, dormancy vs. germination, transpiration and stress responses, the present invention can pave the way to important biotechnological applications.

BRIEF DESCIPTION OF THE DRAWINGS

The features and advantages of the present invention will become apparent from the following detailed description of a preferred embodiment thereof, taken in conjunction with the accompanying drawings, in which:

FIG. 1. depicts two graphs showing that A) the overexpression of ABF3 and ABF4 in rice protoplasts is sufficient to transactivate ABA-inducible Em-GUS expression; and B) that overexpressed ABF3 interacts synergistically with ABA and VP1, but not ABI5.

Figure 2:
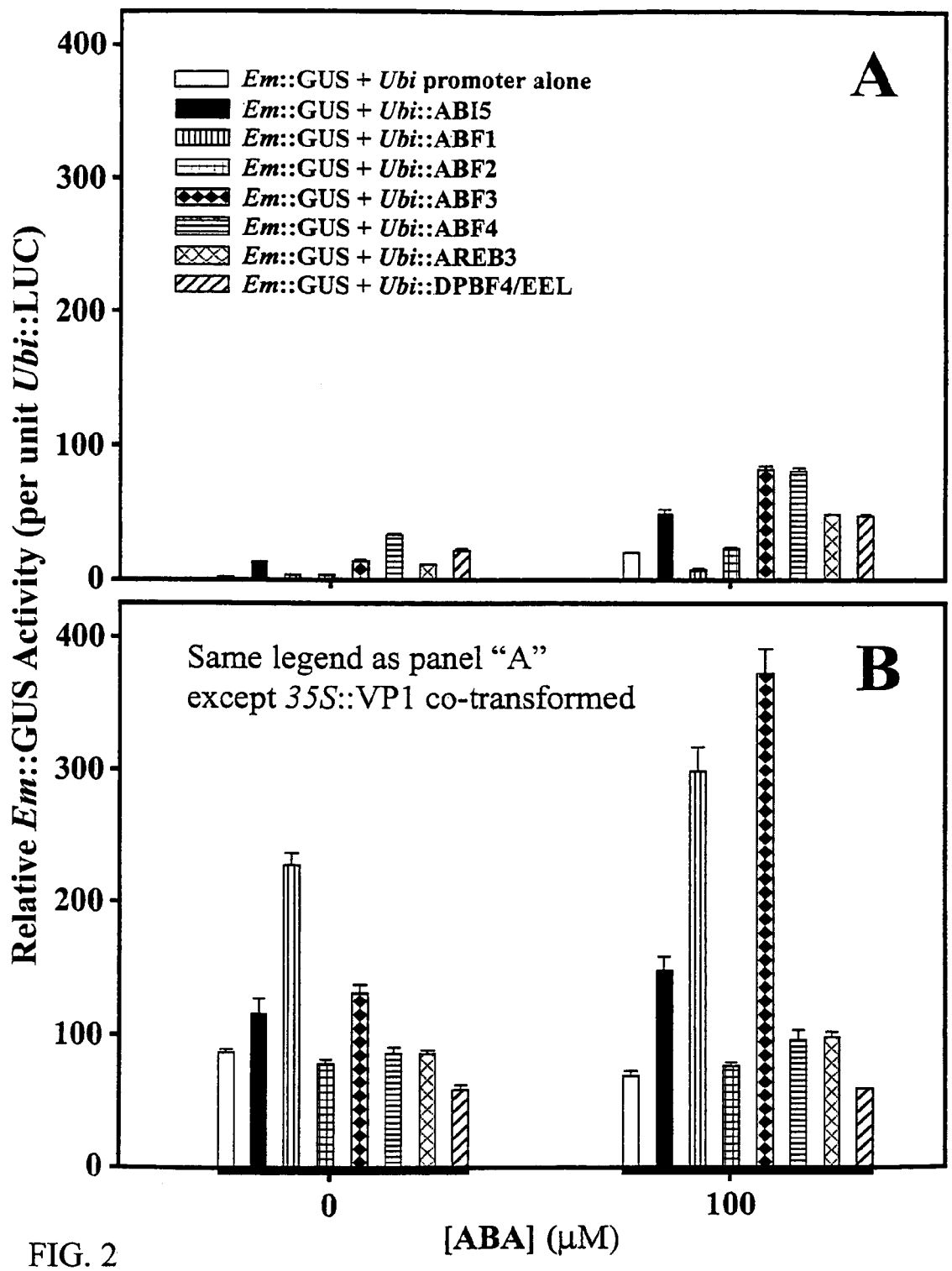
Figure 3:
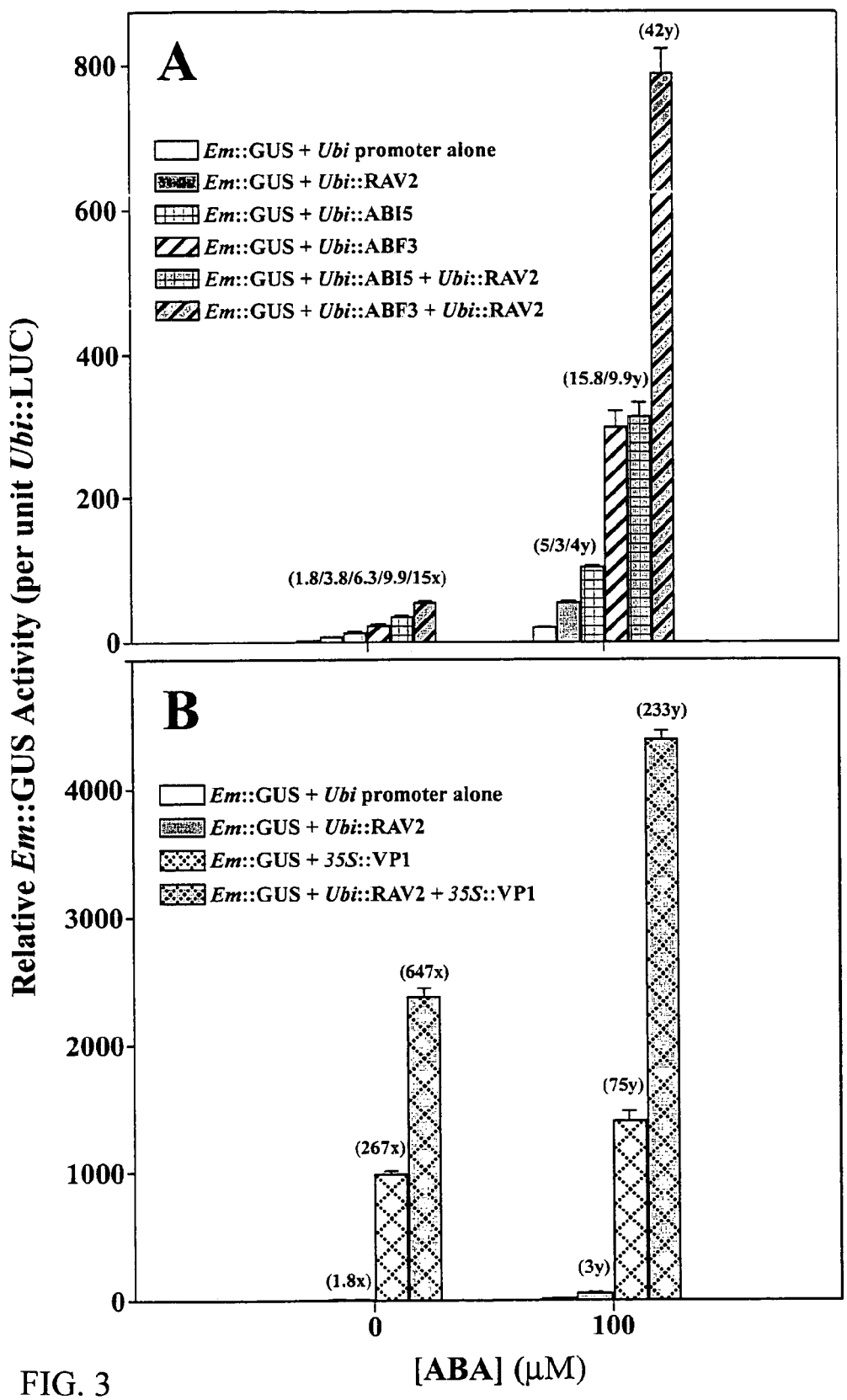

FIG. 2 depicts two graphs showing that A) ABI5, ABF3, ABF4, AREB3, or DPBF4/EEL overexpression in maize mesophyll protoplasts is sufficient to transactivate Em-GUS expression, while B) ABI5, ABF1, and ABF3 but not ABF2, AREB3, ABF4, or DPBF4/EEL can synergize with co-transformed VP1; and FIG. 3 is a graph in two parts showing that A) RAV2 interacts synergistically with the bZIP transcription factors ABI5 and ABF3; and B) that RAV2 interacts synergistically with VP1 in maize mesophyll protoplasts.

DETAILED DESCRIPTION OF THE INVENTION

DEFINITIONS

Unless otherwise indicated, all technical and scientific terms used herein have the same meaning as they would to one of ordinary skill in the art of the present invention. It is to be understood that this invention is not limited to the particular methodology, protocol, and reagents described, as these may vary.

All publications cited herein are expressly incorporated herein by reference for the purpose of describing and disclosing compositions and methodologies which might be used in connection with the invention.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) lo for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 39%, 45%, 50%, 55%, 60%, 65%, 70%, 75%, 80%, 85%, 90%, 95%, or 99% compared to a reference sequence using the programs described herein; preferably BLAST using standard parameters, as described below.

Accordingly, "B3-domain transcription factors" are transcription factors that include a polynucleotide sequence having a B3 domain which is at least 25% identical to the B3 domain of SEQ ID NO:1. More preferably, the B3-domain transcription factor is a transcription factor that includes a polynucleotide sequence having a B3 domain which is at least 45% identical to the B3 domain of SEQ. ID.NO.: 1. Additionally, the B3-domain transcription factors are transcription factors that include a polypeptide sequence having a B3 domain which is at least 40% identical to the B3 domain of SEQ ID NO:2. More preferably, the B3-domain transcription factor is a transcription factor that includes a polypeptide sequence having a B3 domain which is at least 50% identical to the B3 domain of SEQ. ID.NO.: 2. The B3-domain transcription factors also include transcription factors that include a polynucleotide sequence having a B3 domain which is at least 25% identical to the B3 domain of SEQ ID NO:3. More preferably, the B3-domain transcription factor is a transcription factor that includes a polynucleotide sequence having a B3 domain which is at least 45% identical to the B3 domain of SEQ. ID.NO.: 3. Additionally, the B3-domain transcription factors include transcription factors that include a polypeptide sequence having a B3 domain which is at least 40% identical to the B3 domain of SEQ ID NO: 4. More preferably, the B3-domain transcription factor is a transcription factor that includes a polypeptide sequence having a B3 domain which is at least 50% identical to the B3 domain of SEQ. ID.NO.: 4. The "bZIP domain transcription factors" include transcription factors that include a polynucleotide sequence having a bZIP domain which is at least 25% identical to the bZIP domain of SEQ ID NO:5. More preferably, the bZIP domain transcription factor is a transcription factor that includes a polynucleotide sequence having a bZIP domain which is at least 45% identical to the bZIP domain of SEQ. ID.NO.: 5. Additionally, the bZIP domain transcription factors include transcription factors that include a polypeptide sequence having a bZIP domain that is at least 40% identical to the bZIP domain of SEQ ID NO: 6. More preferably, the bZIP domain transcription factor is a transcription factor that includes a polypeptide sequence having a bZIP domain which is at least 60% identical to the bZIP domain of SEQ. ID.NO.: 6. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%. Preferred percent identity of polypeptides can be any integer from 40% to 100%. More preferred embodiments include at least 50%, 55%, 60%, 65%, 70%, 75%, 80%, 85%, 90%, 95%, or 99%. Most preferred embodiments include at least 60% polypeptide identity.

The phrase "nucleic acid" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "polynucleotide sequence" or "nucleic acid sequence" includes both the sense and antisense strands of a nucleic acid as either individual single strands or in the duplex. It includes, but is not limited to, self-replicating plasmids, chromosomal sequences, and pharmacological application of polymers of DNA or RNA. For example, see "Therapeutic silencing of an endogenous gene by systemic administration of modified siRNAs" Nature 432: 173-178 (Nov. 11, 2004). The present invention also includes small interfering RNAs (siRNAs) homologous to the bZIP domain transcription factors and B3 domain transcription factors.

The phrase "nucleic acid sequence encoding" refers to a nucleic acid which directs the expression of a specific protein or peptide. The nucleic acid sequences include, but are not limited to, both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, in planta techniques, and the like. Such a plant containing the exogenous nucleic acid is referred to here as an $R_1$ generation transgenic plant. Transgenic plants which arise from sexual cross or by selfing are descendants of such a plant.

A "B3 domain polynucleotide" is a nucleic acid sequence comprising a coding region of about 100 to about 900 nucleotides, sometimes from about 200 to about 630 nucleotides, lo which hybridizes to SEQ ID NO:1 or 3 under stringent conditions, preferably as defined below, or which encodes a B3 domain polypeptide. B3 domain polynucleotides can also be identified by their ability to hybridize under low stringency conditions (e.g., Tm about 40° C.) to nucleic acid probes having a sequence from position 559 to 885 in SEQ ID NO:3 or from position 1560 to 1929 in SEQ ID NO:1.

A "B3 domain polypeptide" is a sequence of about 100 to about 130 amino acid residues encoded by a B3 domain polynucleotide. A full length B3 domain polypeptide can act as a subunit of a protein capable of acting as a transcription factor in plant cells.

A "bZIP domain polynucleotide" is a nucleic acid sequence comprising a coding region of about 190 nucleotides which hybridizes to SEQ ID NO:5 under stringent conditions, preferably as defined below, or which encodes a bZIP domain polypeptide. bZIP domain polynucleotides can also be identified by their ability to hybridize under low stringency conditions (e.g., Tm about 40° C.) to nucleic acid probes having a sequence from position 1057 to 1251 in SEQ ID NO:5.

A "bZIP domain polypeptide" is a sequence of about 60 amino acid residues encoded by a bZIP domain polynucleotide. A full length bZIP domain polypeptide can act as a subunit of a protein capable of acting as a transcription factor in plant cells.

As used herein, a "homolog" of a particular gene (e.g., SEQ ID NO:1) is a second gene in the same plant type or in a different plant type, which has a polynucleotide sequence of at least 50 contiguous nucleotides which are substantially identical (determined as described herein) to a sequence in the first gene. It is believed that, in general, homologs share a common evolutionary past.

"Increased or enhanced B3 domain activity or expression of a B3 domain gene" refers to an augmented change in B3 domain activity. Examples of such increased activity or expression include the following. B3 domain activity or expression of the B3 domain gene is increased above the level of that in wild-type, non-transgenic control plants (i.e. the quantity of B3 domain activity or expression of the B3 domain gene is increased). B3 domain activity or expression of the B3 domain gene is in an organ, tissue or cell where it is not normally detected in wild-type, non-transgenic control plants (i.e. spatial distribution of B3 domain activity or expression of the B3 domain gene is increased). B3 domain activity or expression is increased when B3 domain activity or expression of the B3 domain gene is present in an organ, tissue or cell for a longer period than in a wild-type, non-transgenic controls (i.e. duration of B3 domain activity or expression of the B3 domain gene is increased).

"Increased or enhanced bZIP domain activity or expression of a bZIP domain gene" refers to an augmented change in bZIP domain activity. Examples of such increased activity or expression include the following. bZIP domain activity or expression of the bZIP domain gene is increased above the level of that in wild-type, non-transgenic control plants (i.e. the quantity of bZIP domain activity or expression of the bZIP domain gene is increased). bZIP domain activity or expression of the bZIP domain gene is in an organ, tissue or cell where it is not normally detected in wild-type, non-transgenic control plants (i.e. spatial distribution of bZIP domain activity or expression of the bZIP domain gene is increased). bZIP domain activity or expression is increased when bZIP domain activity or expression of the bZIP domain gene is present in an organ, tissue or cell for a longer period than in a wild-type, non-transgenic controls (i.e. duration of bZIP domain activity or expression of the bZIP domain gene is increased).

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

An "isolated polynucleotide" or an "isolated DNA segment" having a sequence which encodes a plant transcription factor is a polynucleotide which contains the coding sequence of the plant transcription factor (i) in isolation, (ii) in combination with additional coding sequences, such as fusion protein or signal peptide, in which the plant transcription factor coding sequence is the dominant coding sequence, (iii) in combination with non-coding sequences, such as control elements, such as promoter and terminator elements, effective for expression of the coding sequence in plant cells, and/or (iv) in a vector or host environment in which the plant transcription factor coding sequence is a heterologous gene.

As used herein, the term "plasmid" refers to a circular double-stranded (ds) DNA construct used as a cloning vector, and which forms an extrachromosomal self-replicating genetic element in many bacteria and some eukaryotes.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "promoter" refers to a nucleic acid sequence that functions to direct transcription of a distal gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, enhancer or activator sequences, and regulatory small RNA target-binding sequences. The term "promoter" also refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention. As used herein, the term "promoter" refers to a sequence of DNA that functions to direct transcription of a gene which is operably linked thereto. A promoter may or may not include additional control sequences (also termed "transcriptional and translational regulatory sequences"), involved in expression of a given gene product. In general, transcriptional and translational regulatory sequences include, but are not limited to, promoter sequences, ribosomal binding sites, transcriptional start and stop sequences, translational start and stop sequences, enhancer or activator sequences, and regulatory small RNA target-binding sequences. The promoter may be homologous or heterologous to the cell in which it is found.

A nucleic acid sequence is "heterologous" with respect to a control sequence (i.e. promoter or enhancer) when it does not function in nature to regulate the same gene the expression of which it is currently regulating. Generally, heterologous nucleic acid constructs are introduced into the cell or part of the genome in which they are present, and have been added to the cell by transfection, microinjection, electroporation, or the like. The sequences may contain a control sequence/DNA coding sequence combination that is the same as, or different from, a control sequence/DNA coding sequence combination found in the native plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons). The term "gene" may be used interchangeably herein with the term "nucleic acid coding sequence", and the term "structural gene" which means a DNA coding region.

As used herein, the term "fragment," when referring to a gene sequence means a polynucleotide having a nucleic acid sequence which is the same as part of, but not all of, the nucleic acid sequence of the full length gene. The fragment preferably includes at least 15 contiguous bases of the gene, preferably at least 20-30 bases. With reference to interaction with a transcription factor, the sequence must be of sufficient length to interact with the transcription factor.

As used herein, the terms "transformed", "stably transformed" or "transgenic" with reference to a plant cell means the plant cell has a non-native (heterologous) nucleic acid sequence integrated into its genome which is maintained through one or more generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "effector" refers to plant transcription factors that "effect" the transcription of genes having the appropriate response sequence.

As used herein, the terms "regulatable promoter" and "inducible promoter" may be used interchangeably and refer to any promoter the activity of which is affected by a cis- or trans-acting factor.

As used herein, the terms "transcriptional regulatory protein", "transcriptional regulatory factor" and "transcription factor" may be used interchangeably and refer to a cytoplasmic or nuclear protein that binds a DNA response element and thereby transcriptionally regulates the expression of an associated gene or genes. Transcription factors generally bind directly to a DNA response sequence or element, however in some cases may bind indirectly to another protein, which in turn binds to or is bound to the DNA response element.

As used herein, the terms "response sequence" and "response element" refer to the binding site or sequence for a transcriptional regulatory protein (transcription factor) which may be the part of, overlapping, or adjacent to, a promoter sequence.

As used herein, a "plant cell" refers to any cell derived from a plant, including undifferentiated tissue (e.g., callus) as well as plant seeds, pollen, progagules and embryos.

As used herein, the term "mature plant" refers to a fully differentiated plant.

As used herein, the terms "native" and "wild-type" relative to a given plant trait or phenotype refers to the form in which that trait or phenotype is found in the same variety of plant in nature.

As used herein, the term "plant" includes reference to whole plants, shoot vegetative organs/structures (for example, leaves, stems, tubers, etc.), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of the same. Plant cell, as used herein includes, without limitation, seeds, suspension cultures, embryos, meristematic regions, callus tissue, leaves roots shoots, gametophytes, sporophytes, pollen, and microspores. The class of plants which can be used in the methods of the present invention is generally as broad as the class of higher and lower plants amenable to transformation techniques, including angiosperms (both monocotyledenous and dicotyledenous plants), gymnosperms, ferns, and multicellular algae. It includes plants of a variety of ploidy levels, including aneuploid, polyploid, diploid, haploid and hemizygous.

As used herein, the term "transgenic plant" refers to a plant comprising within its genome a heterologous DNA segment. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

As used herein, the term "enhancement" means increasing the intracellular activity of one or more enzymes in a plant cell and/or plant which are encoded by the corresponding DNA. Enhancement can be achieved with the aid of various manipulations of the cell. In order to achieve enhancement, particularly over-expression, the number of copies of the corresponding gene can be increased, a strong promoter can be used, or the promoter and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in *Methods in Plant Molecular Biology*, Maliga et al, Eds., Cold Spring Harbor Laboratory Press, New York (1995).

Method and Composition of the Invention

The invention provides transgenic plant cells and transgenic plants which express at least two transcription factors that interact synergistically: 1) a first B3-domain transcription factor and 2) a second B3-domain transcription factor or a bZIP domain transcription factor. Expression of the transcription factors is correlated with increased expression of a gene under the control of a promoter with which the transcription factors interact. The two transcription factors are expressed in the same cell and act in concert to modulate expression of the gene to which they are operably linked. Expression of two transcription factors in the same plant results in a level of transgene expression which is greater than the expression of each transcription factor alone, when the transgene is under the control of a promoter with which the transcription factors interact. In other words, as exemplified herein, the level of expression observed when a transgene is expressed under the control of a promoter with which both 1) the B3-domain transcription factor and 2) the bZIP and/or B3-domain transcription factors interact is greater than the expression level observed due to the additive effects of each individual transcription factor.

The invention provides expression cassettes comprising a promoter operably linked to a heterologous polynucleotide sequence or complement thereof, encoding a B3 or bZIP domain-containing polypeptide comprising a sequence which is at least 50% identical to the B3 domain of SEQ ID NO:2 or SEQ ID NO:4 and 60% identical to SEQ ID NO 6. In some embodiments, the polynucleotide sequence is heterologous to any element in the expression cassette. In a preferred embodiment, the B3 domain comprises a polypeptide between about amino acid residue 496 and amino acid residue 619 of SEQ ID NO:2. In a more preferred embodiment, the B3 domain comprises a polypeptide sequence between about amino acid residue 187 and amino acid residue 295 of SEQ ID NO:4. In yet another preferred embodiment, the bZIP domain comprises a polypeptide between about amino acid residue 353 and amino acid residue 417 of SEQ. ID NO: 6.

In particularly preferred embodiments, the B3 domain polypeptide is shown in SEQ ID NO:2, 4, 30, 32, 34, 36, 38, 40, 42, 44, 46, 48, 50, 52, 54, 56, 58, 60, 62, 64 or 66. Such B3 domain polypeptides can be encoded by the polynucleotide sequences shown in SEQ ID NO:1, 3, 31, 33, 35, 37, 39, 41, 43, 45, 47, 49, 51, 53, 55, 57, 59, 61, 63 or SEQ ID NO:65, respectively. In another embodiment the B3 domain polypeptide is a fusion between two or more B3 domain polypeptides or polypeptide subsequences. The polynucleotide sequence can be heterologous to any element in the expression cassette. Such expression cassettes can encode fusions of two or more B3 domain polypeptides or polypeptide subsequences.

In particularly preferred embodiments, the bZIP domain polypeptide is shown in SEQ ID NO: 6, 8, 10, 12, 14, 16, 18, 20, 22, 24, 26 or 28. Such bZIP domain polypeptides can be encoded by the polynucleotide sequences shown in SEQ ID NO: 5, 7, 9 11, 13, 15, 17, 19, 21, 23, 25 or 27. In another embodiment the bZIP domain polypeptide is a fusion between two or more bZIP domain polypeptides or polypeptide subsequences. The polynucleotide sequence can be heterologous to any element in the expression cassette. Such expression cassettes can encode fusions of two or more bZIP domain polypeptides or polypeptide subsequences.

The invention also provides an isolated nucleic acid or complement thereof, encoding a B3 domain polypeptide comprising a sequence at least 50% identical to the B3 domain of SEQ ID NO: 2 or 4. In a preferred embodiment, the B3 domain comprises a polypeptide sequence from about amino acid 187 to about amino acid 295 of SEQ ID NO:4. In another embodiment, the B3 domain polypeptide comprises a polypeptide sequence at least 50% identical to the B3 domain of SEQ ID NO:2 Such B3 domain polypeptides can be encoded by polynucleotide sequences at least 39% identical to B3 domain sequences shown in SEQ ID NO:1 (nucleotide position 1560 to 1929) or SEQ ID NO:3 (nucleotide position 559-885), respectively. In another embodiment, the B3 domain polypeptide is a fusion between two or more B3 domain polypeptides or polypeptide subsequences.

The invention also provides an isolated nucleic acid or complement thereof, encoding a bZIP domain polypeptide comprising a subsequence at least 60% identical to the bZIP domain of SEQ ID NO: 6. In a preferred embodiment, the bZIP domain comprises a polypeptide sequence between about amino acid residue 353 and amino acid residue 417 of SEQ ID NO:6. Such bZIP domain polypeptides can be encoded by the polynucleotide at least 39% identical to sequences shown in SEQ ID NO:5 (nucleotide position 1057 to 1251). In another embodiment, the bZIP domain polypeptide is a fusion between two or more bZIP domain polypeptides or polypeptide subsequences.

In one embodiment, it may be advantageous for propagating or expressing the polynucleotide to carry it in a bacterial or fungal strain with the appropriate vector suitable for the cell type. Common methods of propagating polynucleotides and producing proteins in these cell types are known in the art and are described, for example, in Maniatis et al., *Molecular Cloning: A Laboratory Manual*, Cold Spring Harbor Laboratory Press, New York (1982) and Sambrook et al., *Molecular Cloning: A Laboratory Manual*, Cold Spring Harbor Laboratory Press, New York (1989).

The invention also provides isolated polypeptides comprising amino acid sequences at least 50% identical to the B3 domain of SEQ ID NO:2 or 4 and capable of exhibiting at least one of the biological activities of the polypeptides encoded in SEQ ID NO:2, SEQ ID NO:4 or a fragment thereof. Antibodies capable of binding the above described polypeptides are also provided.

The invention also provides isolated polypeptides comprising amino acid sequences at least 60% identical to the bZIP domain of SEQ ID NO:6 and capable of exhibiting at least one of the biological activities of the polypeptides encoded in SEQ ID NO:6 or a fragment thereof. Antibodies capable of binding the above described polypeptides are also provided. The invention also provides transgenic plant cells or plants comprising an expression cassette comprising a promoter operably linked to a heterologous polynucleotide sequence, or complement thereof, encoding a B3 domain polypeptide comprising a sequence which is at least 50% identical to the B3 domain of SEQ ID NO:2 or 4. Such B3 domain polypeptides can be encoded by the polynucleotide sequences shown in SEQ ID NO:1 or SEQ ID NO:3 respectively. The invention also provides plants that are regenerated from the plant cells discussed above.

The invention also provides transgenic plant cells or plants comprising an expression cassette comprising a promoter operably linked to a heterologous polynucleotide sequence, or complement thereof, encoding a bZIP domain polypeptide comprising a sequence which is at least 60% identical to the bZIP domain of SEQ ID NO:6. Such bZIP domain polypeptides can be encoded by the polynucleotide sequences shown in SEQ ID NO:5. The invention also provides plants that are regenerated from the plant cells discussed above.

In activating transcription of a nucleic acid coding sequence, the transcription factors described herein may interact with (1) a native promoter or (2) a non-native, recombinant or heterologous promoter. In either case, all or part of the promoter sequence is operably linked to a native nucleic acid coding sequence or a heterologous nucleic acid coding sequence (e.g., a transgene) and may be from the same or a different species from that of the plant in which it is present. The transgene may be a reporter gene, such as luciferase (LUC) or β-glucuronidase (GUS), or a gene encoding a recombinant protein that is expressed in the plant.

In practicing the invention, a plant cell may be transformed with one or more vectors, each comprising the coding sequence for one or more plant transcription factors, each operably linked to a tissue specific promoter, wherein the tissue specific promoters may be the same or different. It will be understood by those of skill in the art that once expressed a recombinant transcription factor may act on the promoter which is regulating expression of the transcription factor itself, one or more heterologous target promoters, in addition to acting on multiple native promoters.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular B3 and/or bZIP domain gene. In addition, the term specifically includes sequences (e.g., full length sequences) substantially identical (determined as described below) with a B3 and/or bZIP domain gene sequence and that encode proteins that retain the function of a B3 and/or bZIP domain polypeptide.

In the case of polynucleotides used to inhibit expression of an endogenous or heterologous gene, the introduced sequence need not be perfectly identical to a sequence of the target gene. The introduced polynucleotide sequence will typically be at least substantially identical (as determined below) to the target sequence.

Polynucleotide sequences according to the invention are suitable as hybridization probes for RNA, cDNA and DNA, in order to isolate those cDNAs or genes which exhibit a high degree of similarity to the sequence of the B3 and/or bZIP domain gene.

Polynucleotide sequences according to the invention are also suitable as primers for polymerase chain reaction (PCR) for the production of DNA which encodes a protein having activity of a B3 and/or bZIP domain polypeptide.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The polypeptides according to the invention include polypeptides corresponding to SEQ ID NO. 2 or 4, particularly those with the biological activity of a B3 domain protein, and also includes those, at least 50% of which, preferably at least 60% of which, are homologous with the B3 domain of the polypeptides corresponding to SEQ ID NO. 2 and 4 and which have the cited activity.

The polypeptides according to the invention include polypeptides corresponding to SEQ ID No. 6, particularly those with the biological activity of a bZIP domain protein, and also includes those, at least 60% of which are homologous with the bZIP domain of the polypeptide corresponding to SEQ ID NO. 6 and which have the cited activity.

Another indication that nucleotide sequences are substantially identical is if two molecules hybridize to each other, or a third nucleic acid, under stringent conditions. In the present invention, mRNA encoded by B3 and/or bZIP domain genes of the invention can be identified in RNA blots under stringent conditions using cDNAs of the invention or fragments of at least about 100 nucleotides. Genomic DNA or cDNA comprising genes of the invention can be identified using the same cDNAs specified in SEQ ID NO 1, 3, or 5 (or fragments of at least about 100 nucleotides) under low stringency conditions for heterologous probing of samples.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, *Anal. Biochem.,* 138:267-284 (1984): Tm=81.5° C.+16.6(log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in *Current Protocols in Molecular Biology*, Chapter 2, Ausubel, et al., Eds., Greene Publishing and Wiley-Interscience, New York (2000). Thus, with the foregoing information, the skilled artisan can identify and isolate polynucleotides which are substantially similar to the present polynucleotides. In so isolating such a polynucleotide, the polynucleotide can be used as the present polynucleotide in, for example, increasing the stress tolerance of a plant.

The invention also relates to coding DNA sequences which result from SEQ ID NO. 1, SEQ ID NO: 3 and SEQ ID NO: 5 by degeneration of the genetic code. In the same manner, the invention further relates to DNA sequences which hybridize with SEQ ID NO. 1, 3, or 5 or with parts of SEQ ID NOs. 1, 3, or 5. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function.

In the same manner, the present invention also relates to DNA sequences which hybridize with SEQ ID NO. 1, 3, or 5 or with parts of SEQ ID NOs. 1, 3, or 5. Finally, the present invention relates to DNA sequences which are produced by polymerase chain reaction (PCR) using oligonucleotide primers which result from SEQ ID NOs. 1, 3, or 5. Oligonucleotides of this type typically have a length of at least 15 nucleotides.

In one preferred embodiment, the plant transcription factor is operably linked to a tissue-specific promoter, preferably an inducible promoter.

In a preferred embodiment the polynucleotides of the present invention are in a vector and/or a host cell. Preferably, the polynucleotides are in a plant cell or transgenic plant. In a preferred embodiment, transgenic plant lines, e.g., rice, wheat, corn, barley, oat, rape, cotton, peanut, and soybean are developed and genetic crosses carried out using conventional plant breeding techniques. In one exemplary approach, a first stable transgenic plant line is generated where the plants express two transcription factors, e.g. 1) a B3-domain transcription factor and a bZIP domain transcription factors, or 2) two different B3-domain transcription factors, under the control of a tissue-specific promoter. A number of such lines may be generated with varying levels of transcription factor expression. In practicing the method, these plants may be crossed with a parental transgenic rice, wheat, corn, barley, oat, rape, cotton, peanut, or soybean line that expresses a heterologous protein coding sequence (e.g., a recombinant protein) under the control of a tissue-specific promoter that is responsive to the transcription factors expressed in the first plant line. Plants derived from the resulting cross (F2) have a higher expression level of the heterologous protein in one or more particular seed tissues, than a corresponding non-transgenic plant. In a preferred embodiment, the B3 domain transcription factor(s) and/or bZIP domain transcription factor may be incorporated into the same (original) plant or into two separate transcription factor-expressing lines that are crossed together to make a double transcription factor line wherein the transcription factors will synergize with each other to control the expression of endogenous genes and/or a third recombinant "target". The "target" can also be crossed in and selected for "triple-expressing" lines.

In another preferred embodiment, the present invention provides methods of increasing the stress tolerance of a plant in need thereof, comprising introducing the polynucleotides of the invention into said plant.

In another preferred embodiment, the present invention provides an isolated polypeptide comprising the amino acid sequence in SEQ ID NO:2 or 4 or 6 or those proteins that are at least 40%, preferably 50%, preferably 60% and preferably 95% identity to SEQ ID NO:2, 4, or 6. Preferably, the polypeptides have B3 domain or bZIP activity to effect expression driven by an ABA-inducible promoter.

In another preferred embodiment, the present invention provides a method for making B3 or bZIP domain proteins, comprising culturing the host cell carrying the polynucleotides of the invention for a time and under conditions suitable for expression of the B3 or bZIP, and collecting the B3 or bZIP protein.

In another preferred embodiment the present invention provides a process for screening for polynucleotides which encode a B3 domain and bZIP domain proteins comprising hybridizing the polynucleotide of the invention to the polynucleotide to be screened; expressing the polynucleotide to produce a protein; and detecting the presence or absence of B3 domain activity in said protein.

One embodiment of the present invention is methods of screening for polynucleotides in a sample which have substantial homology to the polynucleotides of the present invention, preferably those polynucleotides encoding a protein having B3 domain activity. The method comprises providing an isolated B3 domain nucleic acid molecule comprising a polynucleotide sequence, or complement thereof, encoding a B3 domain polypeptide with a subsequence at least 50% identical to the B3 domain of SEQ ID NO:2 or 4, contacting the isolated nucleic acid molecule with a sample under conditions which permit a comparison of the sequence of the isolated nucleic acid molecule with the sequence of DNA in the sample; and analyzing the result of the comparison. In some embodiments, the isolated nucleic acid molecule and the sample are contacted under conditions which permit the formation of a duplex between complementary nucleic acid sequences.

One embodiment of the present invention is methods of screening for polynucleotides in a sample which have substantial homology to the polynucleotides of the present invention, preferably those polynucleotides encoding a protein having bZIP domain activity. The method comprises providing an isolated bZIP domain nucleic acid molecule comprising a polynucleotide sequence, or complement thereof, encoding a bZIP domain polypeptide with a subsequence at least 60% identical to the bZIP domain of SEQ ID NO:6, contacting the isolated nucleic acid molecule with a sample under conditions which permit a comparison of the sequence of the isolated nucleic acid molecule with the sequence of DNA in the sample; and analyzing the result of the comparison. In some embodiments, the isolated nucleic acid molecule and the sample are contacted under conditions which permit the formation of a duplex between complementary nucleic acid sequences.

In a preferred embodiment the B3 domain polypeptide and the bZIP domain polypeptide have B3 or bZIP trans-acting activities on ABA-inducible gene expression in a functional transient assay.

In another preferred embodiment, the present invention includes a process for screening in a transient functional assay for polynucleotides which encode a protein having B3 or bZIP trans-acting activity on ABA-inducible gene expression comprising hybridizing the polynucleotides of the invention to the polynucleotide to be screened; expressing the polynucleotide to produce a protein; and detecting the presence or absence of B3 or bZIP trans-acting activity on ABA-inducible gene expression in said functional assay. In another preferred embodiment, the present invention provides a method for making B3 or bZIP proteins, comprising culturing the host cell carrying the polynucleotides of the invention for a time and under conditions suitable for expression of B3 or bZIP proteins, and collecting the B3 or bZIP proteins.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In another preferred embodiment, the present invention provides a method for detecting a nucleic acid with at least 48% homology to the B3 domain nucleotide SEQ ID NO:1 or 3 or 5, sequences which are complimentary to SEQ ID NO:1 or 3 or 5 and/or which encode a protein having substantial identity with the amino acid sequence in SEQ ID NO:2, 4 or 6 respectively, comprising contacting a nucleic acid sample with a probe or primer comprising at least 15 consecutive nucleotides of the nucleotide sequences of SEQ ID NO:1, 3, or 5 or at least 15 consecutive nucleotides of the complement thereof.

Thus, in one embodiment of the present invention, the stress tolerance of a plant can be enhanced or increased by increasing the amount of protein available in the plant, preferably by the enhancement of the B3 and/or bZIP domain gene expression in the plant.

Thus, one embodiment of the present invention are plant cells carrying the polynucleotides of the present invention, and preferably transgenic plants carrying the isolated polynucleotides of the present invention.

Plant Transcription Factors

Transcription factors are capable of sequence-specific interaction with a gene sequence or gene regulatory sequence. The interaction may be direct sequence-specific binding in that the transcription factor directly contacts the gene or gene regulatory sequence, or indirect sequence-specific binding mediated by interaction of the transcription factor with other proteins. In these cases, the binding and/or effect of the B3-domain transcription factor is influenced in a synergistic manner by another B3-domain transcription factor or a bZIP-domain transcription factor.

The gene or gene regulatory region and transcription factor may be derived from the same type of plant (e.g., the same species or genus) or a different type of plant.

The transcription factors used herein produce synergistic results related to the ability of the plant to respond to stress. The B3-domain transcriptions factors and the bZIP transcriptions factors are described in detail above.

Constructs for Expression of a Transcription Factor in a Plant Cell

A heterologous nucleic acid construct or expression vector designed for operation in plants comprising the coding sequence for a plant transcription factor may be used to transiently or stably transform a plant, e.g. a monocot plant. An exemplary heterologous nucleic acid construct or expression vector designed for operation in plants, includes (i) a promoter (transcriptional regulatory region) induced in particular tissue ("tissue-specific"), (ii) the coding sequence for a plant transcription factor operably linked to the promoter, (iii) companion sequences upstream and downstream which are of plasmid or viral origin and provide necessary characteristics to the vector to permit the vector to move the DNA from bacteria to the desired plant host; (iv) a selectable marker sequence; and (v) a transcriptional termination region generally at the opposite end of the vector from the transcription initiation regulatory region. Suitable transformation vectors for the preparation of such constructs are known in the art and many are commercially available.

Vector components may also include a signal sequence. The desired recombinant protein or polypeptide may be produced directly, or as a fusion polypeptide with a heterologous polypeptide, which may be a signal sequence or other polypeptide having a specific cleavage site at the N-terminus of the mature protein or polypeptide. Included in heterologous nucleic acid constructs for use in the methods of the invention are signal sequences that allow processing and translocation of the protein, as appropriate.

In some cases, the recombinant protein may be produced as a precursor protein, which may be further processed in the plant cell culture or following extraction from the plant.

Tissue-Specific Promoters

The transcription regulatory or promoter region of the chimeric gene or heterologous nucleic acid construct is preferably a tissue-specific promoter, for example, a promoter capable of directing expression of a gene product under its control, which is specific to the seed embryo, aleurone, outer layer of the endosperm, mesophyll cells, vascular cells, guard cells, and the like.

Promoter sequences for regulating transcription of operably linked coding sequences include naturally-occurring promoters, or regions thereof capable of directing tissue-specific transcription, and hybrid promoters, which combine elements of more than one promoter. Methods for construction of hybrid promoters are well known in the art.

In some cases, the promoter is derived from the same plant species as the plant in which the nucleic acid construct is to be introduced. Promoters for use in the invention are typically derived from crops such as rice, barley, wheat, corn, sunflower, carrot, bean, rape, and model species such as *Arabidopsis*.

Alternatively, a tissue-specific promoter from one type of monocot may be used to regulate transcription of a gene coding sequence from a different monocot or dicot. Numerous types of appropriate expression vectors, and suitable regulatory sequences are known in the art for a variety of plant host cells. In general, the transcriptional and translational regulatory sequences may include, but are not limited to, promoter sequences, ribosomal binding sites, transcriptional start and stop sequences, translational start and stop sequences, and enhancer or activator sequences.

Effective inducible or tissue-specific transcriptional initiation regions, e.g., promoters, may be isolated from various tissues and/or at various stages of development by a variety of techniques routinely used by those of skill in the art, including, but not limited to: (1) conventional hybridization techniques using known coding sequences from a different species, tissue and/or developmental stage, followed by characterizing the region 5' of the homologous gene to identify the associated transcriptional initiation sequence; (2) subtractive hybridization, (3) differential display, and (4) selective amplification via biotin- and restriction-mediated enrichment, SABRE.

Expression Vector Components

Expression vectors or heterologous nucleic acid constructs, designed for operation in plants, comprise companion sequences upstream and downstream from the expression cassette. The companion sequences are of plasmid or viral origin and provide necessary characteristics to the vector to permit the vector to move DNA from bacteria to the plant host, such as, sequences containing an origin of replication and a selectable marker. Typical secondary hosts include bacteria and yeast.

The transcriptional termination region may be taken from a gene where it is normally associated with the transcriptional initiation region or may be taken from a different gene.

The particular marker gene employed is one that allows for selection of transformed cells as compared to cells lacking the DNA that has been introduced. Preferably, the selectable marker gene is one that facilitates selection at the tissue culture or seedling stages.

In general, a selected nucleic acid sequence is inserted into an appropriate restriction endonuclease site or sites in the vector. Standard methods for cutting, ligating and *E. coli* transformation, known to those of skill in the art, are used in constructing vectors for use in the present invention. Generally, vectors for use in practicing the present invention are constructed using methods known to those skilled in the art.

Plants

The plants used in practicing the invention are of both monocot and dicot origin. The Graminaceae family includes all members of the grass family of which the edible varieties are known as cereals or grains. The cereals include a wide variety of species such as wheat (*Triticum* sps.), rice (*Oryza* sps.), barley (*Hordeum* sps.), oats (*Avena* sps.), rye (*Secale* sps.), corn (*Zea* sps.), and millet (*Pennisettum* sps.). In one embodiment of the invention, preferred family members are rice, wheat, corn, barley, oat, rape, cotton, peanut, and soybean.

Plant cells or tissues derived from the members of the family may be transformed with expression vectors (i.e., plasmid DNA into which the gene of interest has been inserted) using a variety of standard techniques (e.g., microparticle bombardment, electroporation, protoplast fusion or infection with *Agrobacterium*).

Transgenic plant cells obtained as a result of such transformation express the coding sequence for one or more plant transcription factor, e.g. a B3-domain transcription factor and bZIP or B3-domain transcription factors. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art.

In one embodiment of the invention, transgenic plant lines, e.g., rice, wheat, corn, barley, oat, rape, cotton, peanut, and soybean are developed and genetic crosses carried out using conventional plant breeding techniques. In one example of this approach, a first stable transgenic plant line is generated where the plants express two of the transcription factors under the control of a tissue-specific promoter. A number of such lines may be generated with varying levels of transcription factor expression. The plants are crossed with a second transgenic plant line that expresses a heterologous protein coding sequence (e.g., a recombinant protein) under the control of a tissue-specific promoter that is responsive to the transcription factors expressed in the first plant line. The resulting cross (F2) has a higher expression level of the heterologous protein in one or more particular tissues, dependent upon the promoter used.

Transformation of Plant Cells

Vectors useful in the practice of the present invention may be microinjected directly into plant cells by use of micropipettes to mechanically transfer the nucleic acid construct or cassette. Such nucleic acid constructs or cassettes may also be transferred into the plant cell using polyethylene glycol. In addition, high velocity ballistic penetration by small particles with the nucleic acid either within the matrix of small beads or particles, or on the surface may also be used for introduction of nucleic acid sequences into plant cells.

Additional methods for introduction of nucleic acid sequences into plant cells include fusion of protoplasts with other entities, either minicells, cells, lysosomes or other fusible forms for introduction of nucleic acid sequences into plant cells with lipid surfaces; and electroporation. In this technique, electrical impulses of high field strength reversibly permeabilize biomembranes allowing the introduction of plasmids into plant cells or protoplasts. Electroporated plant protoplasts will reform the cell wall, divide, and form plant callus.

Another preferred method of introducing a nucleic acid construct into plant cells is to infect a plant cell, explant, meristem or seed with *Agrobacterium*, in particular *Agrobacterium tumefaciens*. A nucleic acid construct comprising such a sequence of interest can be introduced into appropriate plant cells.

Standard *Agrobacterium* binary vectors are known to those of skill in the art and many are commercially available. Expression vectors typically include polyadenylation sites, translation regulatory sequences (e.g., translation start sites), introns and splice sites, enhancer sequences (which can be inducible, tissue-specific or constitutive), and may further include 5' and 3' regulatory and flanking sequences.

Suitable selectable markers for selection in plant cells are described above and the particular marker gene employed is one which allows for selection of transformed cells as compared to cells lacking the DNA which has been introduced. Preferably, the selectable marker gene is one which facilitates selection at the tissue culture or seedling stages.

Transformed explant cells are screened for the ability to be cultured in selective media having a threshold concentration of selective agent. Explants that can grow on the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plant cells with expression of modified native or non-native plant genes and regeneration of transgenic plants, which can produce a recombinant protein or polypeptide of interest.

The expression of a recombinant protein or polypeptide can be confirmed using any of a number of standard analytical techniques such as Western blot, ELISA, PCR, HPLC, NMR, or mass spectroscopy.

Preferred Emdodiment

Strong and novel activities in rice embryonic and maize mesophyll protoplasts of the transcription factors VP1 (see SEQ. ID. NO: 1 and SEQ. ID. NO.:2), RAV2 (see SEQ. ID. NO.:3 and SEQ. ID. NO.:4), ABI5 (see SEQ. ID. NO.:5 and SEQ. ID.NO.: 6), ABF1, ABF3, ABF4, AREB3 and DPBF4 genes from maize (VPI) and *Arabidopsis* (all others) are demonstrated herein. As shown in the Examples below, the ABA INSENSITIVE-5 (ABI5) basic leucine zipper (bZIP) domain transcription factor and closely related ABI-5-like homologues have been tested for transactivation of the ABA-inducible wheat Em promoter in transiently transformed rice and maize protoplasts. The functional interactions of co-expressed ABI5 and the ABI5-like ABA-Response Element-Binding Factors, such as ABF1, ABF2, ABF3, ABF4, AREB3, and DPBF4/EEL, which have highly conserved domains (C1-C3, bZIP), were tested with each other and with co-expressed maize VIVIPAROUS-I (VP1) B3-domain transcription factor. Overexpressed *Arabidopsis ABI5*, ABF3, ABF4, AREB3, DPBF4, and maize VP1, but not ABF1 and ABF2, individually show synergy with ABA in rice embryonic and/or maize mesophyll protoplasts. However, when ABI5 and ABF3 are co-expressed in rice protoplasts, they show no synergistic interactions with each other, in contrast to strong synergy observed with ABI5, or ABF3 co-expressed with VP1 in rice or maize. Furthermore, AREB3, DPBF4/EEL, and ABF4 do not work in synergy with co-transformed maize VP1, whereas ABI5, ABF3 and ABF1 can synergize with VP1 in maize mesophyll protoplasts. This latter result is in contrast to the observation that ABF1 does not appear to interact with ABA alone. Taken together, these functional data provide several examples to support the claim that formulations of bZIP domain transcription factors with B3-domain transcription factors will provide novel and useful means to effect stress- and ABA-inducible gene expression that in turn will enhance valuable traits such as productivity, yields, and stress tolerance of commercial varieties of plants. The data provides strong evidence that expression of these and homologous transgenes from, and into, various plant partly dependent on increased ABI5 expression. Taken together, these results show that these transcription factors participate in combinatorial control of gene expression, possibly by forming a regulatory complex mediating seed-specific and/or ABA-inducible expression.

Table 1 documents the polypeptide and nucleotide similarities of the bZIP domains of select *Arabidopsis* genes compared to ABI5. Significant functional effects have been shown on transactivation of the Em promoter for most of these family members. The percentage identity and similarity results for polypeptides are relative, since the BLASTP alignment algorithm does not necessarily take into account all residues of the bZIP. The E values are directly comparable measures of significant homologies between and among pairs of genes. (Altschul et al., Gapped BLAST and PSI-BLAST: a new generation of protein database search programs. *Nucleic Acids Res.* 25:3389-3402 (1997)). For example, the difference in E values between ABF3.2 and ABF3.1 is 1000-fold relatively higher homology of ABF3.2 to ABI5 than ABF3.1.

TABLE 1

Pairwise comparison of polypeptide and nucleotide homologies between ABI5-Like Family members and ABI5 bZIP domains.

| AGI | Annotation | Percent Identity of ABI5bZIP (aa 353-417, SEQ. ID NO. 6) | Percent Similarity ABI5 bZIP | E | % n.t. Identity with ABI5 bZIP (n.t. 1057-1251, SEQ ID NO. 5) | SEQ. ID. NO. 1) nucleotides 2) protein |
|---|---|---|---|---|---|---|
| At2g36270 | ABI5 | 100 | — | 4.E−30 | 100 | 1)SEQ. ID. NO. 5<br>2)SEQ. ID. NO.: 6 |
| At1g49720 | ABF1 | 62 | 72 | 1.E−14 | 52 | 1)SEQ. ID. NO.: 7<br>2)SEQ. ID. NO.: 8 |
| At5g42910 | ABF2-Like | 50 | 69 | 6.E−10 | 53 | 1)SEQ. ID. NO.: 9<br>2)SEQ. ID. NO.: 10 |
| At1g45249 | ABF2 | 71 | 81 | 3.E−17 | 62 | 1)SEQ. ID. NO.: 11<br>2)SEQ. ID. NO.: 12 |
| At4g34000 | ABF3.2 | 66 | 80 | 8.E−18 | 56 | 1)SEQ. ID. NO.: 13<br>2)SEQ. ID. NO.: 14 |
| At4g34000 | ABF3.1 | 80 | 93 | 8.E−15 | 52 | 1)SEQ. ID. NO.: 15<br>2)SEQ. ID. NO.: 16 |
| At3g19290 | ABF4 | 63 | 80 | 1.E−16 | 58 | 1)SEQ. ID. NO.: 17<br>2)SEQ. ID. NO.: 18 |
| At3g56850 | AREB3 | 61 | 73 | 3.E−13 | 39 | 1)SEQ. ID. NO.: 19<br>2)SEQ. ID. NO.: 20 |
| At3g44460 | DPBF2 | 67 | 80 | 6.E−18 | 52 | 1)SEQ. ID. NO.: 21<br>2)SEQ. ID. NO.: 22 |
| At2g41070 | DPBF4/EEL | 69 | 87 | 1.E−13 | 48 | 1)SEQ. ID. NO.: 23<br>2)SEQ. ID. NO.: 24 |
| At1g03970 | GBF4 | 60 | 72 | 4.E−12 | 48 | 1)SEQ. ID. NO.: 25<br>2)SEQ. ID. NO.: 26 |
| At5g44080 | GBF4-Like | 63 | 73 | 1.E−12 | 54 | 1)SEQ. ID. NO.: 27<br>2)SEQ. ID. NO.: 28 | species in target tissues such as leaves or seeds will render transgenic horticultural and ornamental plants and crops to be better able to withstand environmental stress via coordinated regulation of multiple endogenous gene sets in stress tolerance pathways.

In the Examples and previously published results, it has been demonstrated that over-expression of maize VP1, *Arabidopsis* ABI5, or several ABI5-related family members transactivate various ABA-inducible promoters from both monocots and dicots in rice or maize protoplasts, proving that these transcription factors are key targets of a conserved ABA signaling pathway in plants. Others have shown that ectopic expression of ABI3, ABI4, or ABI5 transcription factors results in ABA hypersensitivity of vegetative tissues which is Table 2 documents that the VP1 B3-domain protein sequence can be used to claim *Arabidopsis* ABI3, LEC2, FUS3, and At4g21550(=AB3L3), whereas the RAV2 protein and/or its B3 domain can be used to claim "more preferred embodiments" (>50% identity or similarity) with At1g13260=RAV1, At3g25730=RAV1-Like, At1g25560=RAV2-Like, 2g30470=B3L1At4g32010=AB3L2, At4g01500=AB3L4, At1g51120=AB3L5, At2g46870=AB3L6, At1g01030=AB3L7, At2g36080=AB3L8, At1g50680=AB3L9, At3g61970=AB3L10, At5g06250=AB3L11, At3g11580=AB3L12, and At2g28350=AB3L16.

The AGI indications in both Table 1 and Table 2 can be used to obtain additional information about the specific proteins and polynucleotides on the website www.arabidopsis.org.

TABLE 2

Pairwise homologies between *Arabidopsis* ABI3-Like family members and the VIVIPAROUS1 B3 domain or RAV2 protein.*

| AGI number | Annotation | Percent Identity with VP1b3 (aa496-619 SEQ ID NO: 2) | Percent Similar VP1b3 | E | Percent Identity with RAV2 (SEQ. ID NO. 4) | Percent Similar with RAV2 | E | Percent Identity with RAV2b3 (aa187-295, SEQ ID NO. 4) | Percent Similar with RAV2b3 | E | % n.t. identity with RAV2 B3 domain (nt. 559-885 SEQ ID. NO. 3) | SEQ. ID. NO: 1) nucleotides 2) protein |
|---|---|---|---|---|---|---|---|---|---|---|---|---|
| At3g24650 | ABI3 | 84 | 90 | 2.E-56 | | | | | 49 | 3.E-10 | 48 | 1)SEQ. ID. NO.: 29 2)SEQ. ID. NO.: 30 |
| At3g26790 | FUS3 | 57 | 74 | 7.E-32 | | | | 39 | 58 | 1.E-10 | 47 | 1)SEQ. ID. NO.: 31 2)SEQ. ID. NO.: 32 |
| At1g28300 | LEC2 | 52 | 70 | 1.E-29 | | | | 34 | 50 | 1.E-09 | 49 | 1)SEQ. ID. NO.: 33 2)SEQ. ID. NO.: 34 |
| At1g13260 | RAV1 | 36 | 54 | 2.E-09 | 67 | 78 | 1.E-111 | 86 | 92 | 3.E-50 | 65 | 1)SEQ. ID. NO.: 35 2)SEQ. ID. NO.: 36 |
| At3g25730 | RAV1-Like | 35 | 51 | 2.E-09 | 62 | 75 | 1.E-101 | 73 | 85 | 6.E-43 | 62 | 1)SEQ. ID. NO.: 37 2)SEQ. ID. NO.: 38 |
| At1g68840 | RAV2 | 33 | 46 | 6.E-11 | 100 | — | 0.E+00 | 100 | — | 4.E-61 | 100 | 1)SEQ. ID. NO.: 3 2)SEQ. ID. NO.: 4 |
| At1g25560 | RAV2-Like | 35 | 50 | 9.E-10 | 75 | 83 | 1.E-135 | 83 | 86 | 2.E-50 | 66 | 1)SEQ. ID. NO.: 39 2)SEQ. ID. NO.: 40 |
| At2g30470 | AB3L1 | 42 | 60 | 2.E-17 | 43 | 65 | 1.E-13 | 43 | 65 | 1.E-14 | 61 | 1)SEQ. ID. NO.: 41 2)SEQ. ID. NO.: 42 |
| at4g32010 | AB3L2 | 40 | 60 | 6.E-17 | 40 | 65 | 5.E-13 | 40 | 65 | 5.E-14 | 50 | 1)SEQ. ID. NO.: 43 2)SEQ. ID. NO.: 44 |
| At4g21550 | AB3L3 | 38 | 62 | 6.E-14 | | | | | 59 | 4.E-11 | 56 | 1)SEQ. ID. NO.: 45 2)SEQ. ID. NO.: 46 |
| At4g01500 | AB3L4 | 31 | 51 | 2.E-09 | 60 | 73 | 2.E-33 | 59 | 73 | 1.E-33 | 74 | 1)SEQ. ID. NO.: 47 2)SEQ. ID. NO.: 48 |
| At1g51120 | AB3L5 | 34 | 51 | 2.E-08 | 39 | 58 | 3.E-39 | 51 | 67 | 6.E-22 | 68 | 1)SEQ. ID. NO.: 49 2)SEQ. ID. NO.: 50 |
| At2g46870 | AB3L6 | 32 | 52 | 2.E-09 | 65 | 80 | 4.E-39 | 68 | 83 | 6.E-39 | 78 | 1)SEQ. ID. NO.: 51 2)SEQ. ID. NO.: 52 |
| At1g01030 | AB3L7 | 32 | 55 | 9.E-08 | 54 | 70 | 3.E-40 | 69 | 82 | 3.E-39 | 59 | 1)SEQ. ID. NO.: 53 2)SEQ. ID. NO.: 54 |
| At2g36080 | AB3L8 | 31 | 48 | 4.E-07 | 66 | 79 | 6.E-38 | 68 | 79 | 5.E-37 | 58 | 1)SEQ. ID. NO.: 55 2)SEQ. ID. NO.: 56 |

TABLE 2-continued

Pairwise homologies between *Arabidopsis* ABI3-Like family members and the VIVIPAROUS1 B3 domain or RAV2 protein.*

| AGI number | Annotation | Percent Identity with VP1b3 (aa496-619 SEQ ID NO. 2) | Percent Similar VP1b3 | E | Percent Identity with RAV2 (SEQ. ID NO. 4) | Percent Similar with RAV2 | E | Percent Identity with RAV2b3 (aa187-295, SEQ ID NO. 4) | Percent Similar with RAV2b3 | E | % n.t. identity with RAV2 B3 domain (nt. 559-885 SEQ ID. NO. 3) | SEQ. ID. NO: 1) nucleotides 2) protein |
|---|---|---|---|---|---|---|---|---|---|---|---|---|
| At1g50680 | AB3L9 | 32 | 47 | 3.E-07 | 39 | 56 | 7.E-41 | 50 | 65 | 8.E-22 | 68 | 1)SEQ. ID. NO.: 57 2)SEQ. ID. NO.: 58 |
| At3g61970 | AB3L10 | 31 | 49 | 1.E-07 | 67 | 83 | 3.E-38 | 67 | 83 | 2.E-38 | 76 | 1)SEQ. ID. NO.: 59 2)SEQ. ID. NO.: 60 |
| At5g06250 | AB3L11 | 29 | 45 | 3.E-07 | 63 | 77 | 8.E-37 | 64 | 77 | 3.E-37 | 74 | 1)SEQ. ID. NO.: 61 2)SEQ. ID. NO.: 62 |
| At3g11580 | AB3L12 | 28 | 43 | 3.E-07 | 57 | 71 | 2.E-38 | 62 | 77 | 8.E-36 | 48 | 1)SEQ. ID. NO.: 63 2)SEQ. ID. NO.: 64 |
| At2g28350 | AB3L16 | 29§ | 38§ | 0.42 | 35 | 53 | 7.E-10 | 36 | 54 | 1.E-10 | 51 | 1)SEQ. ID. NO.: 65 2)SEQ. ID. NO.: 66 |

*Altschul S F, Madden T L, Schaffer A A, Zhang J, Zhang Z, Miller W, Lipmann D J (1997) Gapped BLAST and PSI-BLAST: a new generation of protein database search programs. Nucleic Acids Res 25: 3389-3402. See http://www.arabidopsis.org/
†Higgins D, Thompson J, Gibson T, Thompson J D, Higgins D G, Gibson T J (1994) CLUSTAL W: improving the sensitivity of progressive multiple sequence alignment through sequence weighting, position-specific gap penalties and weight matrix choice. Nucleic Acids Res. 22: 4673-4680. See European Bioinformatics Institute http://www.ebi.ac.uk/clustalw
‡Compared to ABI3 B3 domain (aa551-674, SEQ ID NO. 30).

EXAMPLE 1

Materials and Methods

Plant Materials. Maize mesophyll protoplasts were isolated from 20-hr illuminated leaves of 10 day old maize seedlings that had been kept in the dark at 25° C. The middle part of the second leaves (about 6 cm in length) was cut into 0.5 mm strips with a razor blade and digested in an enzyme solution containing 1% (w/v) cellulose RS, 0.1% (w/v) macerozyme R10 (Yakult Honsha, Nishinomiya, Japan), 0.6 M mannitol, 10 mM MES (pH 5.7), 1 mM $CaCl_2$, 1 mM $MgCl_2$, 10 mM β-mercaptoethanol, and 0.1% BSA (w/v) for 3 hr at room temperature. Protoplasts were released by shaking on a rotary shaker at 80 rpm for 10 min and were filtered through a 70 μm nylon filter. Protoplasts were collected by centrifugation at 100 g for 2 min, washed in cold 0.6 M mannitol solution, centrifuged, and resuspended at $2 \times 10^6$/mL in cold 0.6 M mannitol. Electroporation conditions were 400 V/cm, 200 μF, 10 msec, and two pulses with a Biorad GenePulser apparatus. Each sample contained $5 \times 10^4$ protoplasts and about 50 μg DNA in 0.3 mL of 0.6 M mannitol and 20 mM KCl.

Embryonic rice (Oryza sativa) callus cultures (Radon 6 from the International Rice Research Institute, Los Baños, Phillipines) were obtained. Embryonic rice callus cultures were grown as suspensions in liquid culture as well as on phytagel plates containing MS medium supplemented with 2.0 mg/L 2,4-D. Cultures were propagated and digested for making protoplasts as previously described except that 10 mM HEPES (Sigma, St. Louis, Mo., USA), pH 5.6, was substituted for phosphate in the Krens' F medium, and 2% (weight/volume; w/v) cellulase YC, 0.35% (w/v) macerozyme, and 0.1% (w/v) pectolyase Y23 were used for overnight digestion (Karlan Research Products, Santa Rosa, Calif., USA). Protoplasts were transformed with various mixtures of DNA reporter and effector constructs using polyethylene glycol precipitation. Transformed protoplasts were incubated with or without 100 μM ABA for 16h in the dark in Krens solution before quantifying β-glucuronidase (GUS) and luciferase (LUC) reporter enzyme activities as previously described. ABA was dissolved and stored in absolute ethanol at −20° C. as a 0.1 M stock solution. Prior to use, required dilutions of ABA were made in Krens solution, and control samples received the same volume of solvent as in ABA treatments.

Plasmid Constructs

Plasmid pBM207 contains the wheat (Triticum aestivum) Early Methionine-labeled (Em) promoter driving the expression of GUS, encoded by uidA from Escherichia coli. Plasmid pDH359 contains ABI5 cDNA driven by Ubiquitin promoter. Plasmid pCR349.13S contains the 35S promoter driving the VP1 sense cDNA. Plasmid pDirect2.6 contains the Ubi promoter in a reverse orientation and was used as control construct to balance the total amount of input plasmid DNA between various treatments. Plasmid pAHC18 contains the Ubi promoter driving firefly (Photinus pyralis) LUC cDNA and was included in transformations to provide an internal reference for non-ABA-inducible transient transcription in reporter enzyme assays. ABF1-ABF4, AREB3, and DPBF4 were amplified by PCR using gene-specific primers from an Arabidopsis cDNA library (Minet et al. Plant J. 2:417 (1992)) and were cloned into plasmid pDH349 (Gampala et al. J. Biol. Chem. 277: 1689 (2002)) containing the maize Ubiquitin promoter and nopaline synthase 3' termination signals. Primers used for PCR amplification are listed in Table 3.

TABLE 3

Gene-specific PCR primers used to clone Arabidopsis ABI5-like cDNAs used herein.

| Gene | | Primer sequence (5'->3'; F = forward, R = reverse) |
|---|---|---|
| ABF1 | | |
| SEQ ID NO | 67 | F: cccaagcttggatccaaagggtctgattcgtttgt |
| SEQ ID NO | 68 | R: cggggtaccgttaacgtcacatcttctctatagct |
| ABF2 | | |
| SEQ ID NO | 69 | F: cccaagcttggatcccccaaacgaagaaccaaaca |
| SEQ ID NO | 70 | R: cggggtaccgatatcttcttcaaaattggtaactc |
| ABF3 | | |
| SEQ ID NO | 71 | F: ccgctcgagggatccgaagcttgatcctcctagtt |
| SEQ ID NO | 72 | R: cggggtaccgatatcagatacaagataaattcact |
| ABF4 | | |
| SEQ ID NO | 73 | F: cccaagcttggatccgaacaagggttttagggctt |
| SEQ ID NO | 74 | R: cggggtaccgatatcgttgccactcttaagtaata |
| AREB3 | | |
| SEQ ID NO | 75 | F: cccactagtggatccatggattctcagaggggtat |
| SEQ ID NO | 76 | R: cggggtaccgatatctcagaaaggagccgagcttg |
| DPBF4 | | |
| SEQ ID NO | 77 | F: cccggtaccggatccacagtttctaaggcaaaata |
| SEQ ID NO | 78 | R: cggaggcctgaattcacttgaactagtgtttgtac |

Results

Previous results demonstrated that overexpressed ABF1 and ABF3 had positive effects on ABA-inducible Em-GUS reporter gene expression in transiently transformed rice protoplasts, providing functional evidence for the involvement of these proteins in ABA- and stress signal transduction. Simultaneously, it has been shown that ABF2, ABF3 and ABF4 overexpression in transgenic *Arabidopsis* results in ABA hypersensitivity and other ABA-associated phenotypes such as altered ABA-inducible gene expression and glucose signaling, reduced transpiration, and enhanced drought tolerance. The functional roles of the ABI5-like family members ABF1-ABF4 in regulation of ABA-inducible gene expression in rice protoplasts were tested and the results are shown in FIG. 1. FIG. 1A shows that the overexpression of ABF3 and ABF4 is sufficient to transactivate ABA-inducible Em-GUS expression in rice protoplasts. Protoplasts were transformed with Em-GUS and a "dummy" effector construct (pD2.6 containing only the *Ubiquitin* promoter used to drive effector expression) or co-transformed with a Ubi-ABF construct and treated with or without 100 μM ABA. The values shown in FIG. 1A are the average (±S.E.M.) of four replicate transformations. Consistent with previous results, overexpressed ABF1 and ABF3 had slight and strong synergy with exogenous ABA, respectively. However, overexpression of ABF2 had no effect on Em-GUS expression (see FIG. 1A). Interestingly, overexpression of ABF3 or ABF4 was sufficient for transactivation of the Em promoter. These results are consistent with those of previous researchers who showed that overexpressed ABF3 or ABF4 resulted in accumulation of the LEA genes rd29A and rab18.

FIG. 1B displays the results of an ABA-inducible reporter gene expression experiment with transiently-transformed rice protoplasts overexpressing ABI5, ABF3, and VP1 transcription factors alone and in pairwise co-transformations. FIG. 1B shows that the overexpressed ABF3 interacts synergistically with ABA and VP1, but not with ABI5. Rice protoplasts were transformed with either Em-GUS alone or in pairwise combinations of Ubi-ABF3, Ubi-ABI5, or 35S-VP1. The values in FIG. 1B are the average (±S.E.M.) of four replicate transformations. ABF3 is a related member of the ABI5-family of bZIP transcription factors. As previously reported, ABI5, ABF3, and VP1 transactivated the Em promoter and acted in synergy with ABA. More importantly, ABF3 and VP1 synergized with each other and with ABA when co-expressed. This activity was about twice the synergistic activity seen between ABI5 and VP1. However, paired expression of ABF3 and ABI5 bZIPs in protoplasts did not result in synergy, see FIG. 1B. Based on these two examples of ABI5-family member synergy with maize VP1, it is proposed that most members of the ABI5 bZIP family can have functional interactions with VP1 and ABI3, including homologues from various species.

To provide evidence to support the claim that transcriptional regulation of ABA signaling is highly conserved among higher plants and in different tissue types, various ABI5-like homologues from *Arabidopsis* were tested for their ABA signaling activities and functional interactions with VP1 in maize mesophyll protoplasts. The results are shown in FIG. 2. FIG. 2A shows that AREB3 or DPBF4/EEL overexpression in maize mesophyll protoplasts is sufficient to transactivate Em-GUS expression. Furthermore, ABF1 and ABF3, but not ABF2, AREB3, ABF4, or DPBF4/EEL, can synergize with co-transformed VP1 (FIG. 2B). The values in FIG. 2 are the average (±S.E.M.) of four replicate transformations. As previously shown for rice embryonic protoplasts (see FIG. 1), ABI5, ABF3 and ABF4 synergize with exogenous ABA and are sufficient for transactivation of the Em promoter when overexpressed in maize mesophyll protoplasts (FIG. 2A). ABF1 and ABF2 have lower levels of ABA synergy compared to ABF3 and ABF4 in maize (FIG. 2A), similar to activities observed in rice (see FIG. 1). Furthermore, the ABI5-like family members AREB3 and DPBF4/EEL synergize with exogenous ABA and are sufficient when overexpressed to transactivate the Em promoter (see FIG. 2A). This finding demonstrates that ABI5-like family members can function in ABA signaling and suggests they may have novel/unique functions and activities including interactions with VP1 and VP1-like homologues. Indeed, ABF1 showed a strong synergy with VP1 in maize protoplasts despite showing little synergy with ABA (compare FIG. 2B with FIG 2A), unlike ABI5 and ABF3, which showed similar interactions with ABA and VP1 as seen in rice, (compare FIG. 1 and FIG. 2). Interestingly, ABF4 and AREB3 showed no functional interactions with VP1 in maize mesophyll protoplasts, while DPBF4/EEL showed some antagonism of ABA inducible Em-GUS expression when co-expressed with VP1 (see FIG. 2B). This latter result is consistent with the published genetic and biochemical evidence in *Arabidopsis* that DPBF4/EEL competes directly with ABI5 for functional interactions with ABI3 in transactivating ABA inducible promoters. Therefore, both similarities and differences are seen in the functional interactions of *Arabidopsis* ABI5-like genes with VP1. It is proposed that other VP1-like family members of *Arabidopsis*, of which there are over 20, may be the cognate partners of ABI5-like family members such as ABF2 and ABF4 that may regulate distinct, or tissue-specific aspects of ABA and stress signaling.

EXAMPLE 2

To test the involvement of ABI3-Like B3 domain transcription factors in ABA signaling, ABA-inducible reporter gene transactivation by the B3 domain-containing RAV2 was assayed in maize mesophyll protoplasts transiently co-transformed with a full length cDNA under transcriptional control of the *Ubiquitin* promoter. Activation of Em-GUS reporter gene expression by RAV2, relative to non-ABA inducible Ubi-LUC reference reporter as internal control, and functional interactions of RAV2 with VP1, ABI5, and the ABI5-Like ABF3 were compared in protoplasts treated with or without 100 uM ABA (see FIG. 3). The results in FIG. 3A show that: 1) the novel B3 domain transcription factor RAV2, ABI5, and ABF3 are sufficient for specific Em-GUS transactivation; and 2) RAV2 synergizes with ABI5 and ABF3, similar to the results in FIGS. 1 and 2 provided above. Furthermore, results shown in FIG. 3B demonstrate that maize VP1 and *Arabidopsis* RAV2, a ABI3-Like B3 domain transcription factor, act synergistically to activate Em-GUS expression, demonstrating that these novel interactions involve mechanisms conserved between monocots and dicots. Furthermore, this synergism is enhanced by ABA, as shown in FIG. 3B. RAV2 transactivation is antagonized by co-transformation of the ABA-INSENSITIVE-1 dominant negative allele (data not shown), which support the notion that the RAV2 mechanism reported here is specific to ABA signaling.

Although the present invention has been disclosed in terms of a preferred embodiment, it will be understood that numerous additional modifications and variations could be made thereto without departing from the scope of the invention as defined by the following claims:

What is claimed is:

1. A method of producing a transgenic plant comprising a) transforming a plant cell with an expression vector comprising i) a polynucleotide sequence encoding B3-domain transcription factor having a polynucleotide sequence with a B3 domain sequence which is at least 73% identical to the B3 domain sequence of SEQ. ID. NO.: 3 and ii) a polynucleotide sequence encoding a bZIP transcription factor having a polynucleotide sequence with a bZIP domain sequence which is at least 66% identical to the bZIP domain sequence of SEQ. ID. NO. 13, and b) generating from the plant cell a transgenic plant with a synergistic transactivation of ABA-inducible promoters providing increased tolerance to environmental stress as compared to a wild type variety of the plant.

2. The method of claim 1, wherein said B3-domain transcription factor is RAV2 having a polynucleotide sequence as defined by SEQ. ID.NO: 3.

3. The method of claim 2, wherein said bZIP domain transcription factor is ABF3 having a polynucleotide sequence as defined by SEQ. ID.NO.: 13.

4. The method of claim 1, wherein said bZIP domain transcription factor is ABF3 having a polynucleotide sequence as defined by SEQ.ID.NO.: 13.

5. The method of claim 1, wherein said transgenic plant is a monocot plant or a dicot plant.

6. The method of claim 1, wherein said expression vector is a tissue-specific expression vector.

7. A method of producing a transgenic plant comprising a) transforming a plant cell with an expression vector comprising i) a polynucleotide sequence that encodes a B3-domain transcription factor having a polypeptide sequence with a B3 domain which is at least 58% identical to the B3 domain of SEQ. ID. NO.: 4 and ii) a polynucleotide sequence that encodes a bZIP transcription factor having a polypeptide sequence with a bZIP domain which is at least 66% identical to the bZIP domain of SEQ. ID. NO: 14, and b) generating from the plant cell a transgenic plant with a synergistic transactivation of ABA-inducible promoters providing increased tolerance to environmental stress as compared to a wild type variety of the plant.

8. The method of claim 7, wherein said B3-domain transcription factor is RAV 2 having a polypeptide sequence as defined by SEQ. ID.NO.: 4.

9. The method of claim 8, wherein said bZIP domain transcription factor is ABF3 having a polypeptide sequence as defined by SEQ. ID.NO.: 14.

10. The method of claim 7, wherein said bZIP domain transcription factor is ABF3 having a polypeptide sequence as defined by SEQ.ID.NO.: 14.

11. The method of claim 7, wherein said transgenic plant is a monocot plant or a dicot plant.

12. The method of claim 7, wherein said expression vector is a tissue-specific expression vector.

13. A transgenic plant, comprising a) a polynucleotide sequence encoding a B3-domain transcription factor having a polynucleotide sequence with a B3 domain sequence which is at least 73% identical to the B3 domain sequence of SEQ. ID. NO.:3 operably linked to a tissue specific promoter, said transgenic plant is transformed with said polynucleotide sequence with said B3 domain sequence and b) a polynucleotide sequence encoding a bZIP domain transcription factor having a polynucleotide sequence with a bZIP-domain sequence which is at least 66% identical to the bZIP domain sequence of SEQ. ID. NO.13: operably linked to a tissue specific promoter, said transgenic plant is transformed with said polynucleotide sequence with said bZIP domain sequence, wherein expression of the B3-domain transcription factor and the bZIP domain transcription factor in the tissue of said plant is effective to synergistically activate transcription of a gene operably linked to a promoter with which said transcription factor functionally interacts.

14. The transgenic plant of claim 13, wherein said B3-domain transcription factor is RAV2 having a polynucleotide sequence as defined by SEQ. ID.NO: 3.

15. The transgenic plant of claim 14, wherein said bZIP domain transcription factor is ABF3 having a polynucleotide sequence as defined by SEQ. ID.NO.: 13.

16. The transgenic plant of claim 13, wherein said bZIP domain transcription factor is ABF3 having a polynucleotide sequence as defined by SEQ.ID.NO.: 13.

17. The transgenic plant of claim 13, wherein said transgenic plant is a monocot plant or a dicot plant.

18. A transgenic plant, comprising a) a B3-domain transcription factor having a polypeptide sequence with a B3 domain which is at least 58% identical to the B3 domain of SEQ. ID. NO. 4 operably linked to a tissue specific promoter, said transgenic plant includes a plant cell that is transformed with a polynucleotide that encodes said B3-domain transcription factor and b) a bZIP domain transcription factor having a polypeptide sequence with a bZIP domain which is at least 66% identical to the bZIP domain of SEQ. ID. NO.: 14 operably linked to a tissue-specific promoter, said transgenic plant includes a plant cell that is transformed with a polynucleotide that encodes said bZIP transcription factor, wherein expression of the B3-domain transcription factor and the bZIP domain transcription factor in the tissue of said plant is effective to synergistically activate transcription of a gene operably linked to a promoter with which said transcription factor functionally interacts.

19. The transgenic plant of claim 18, wherein said B3-domain transcription factor is RAV2 having a polypeptide sequence as defined by SEQ. ID.NO.: 4.

20. The transgenic plant of claim 19, wherein said bZIP domain transcription factor is ABF3 having a polypeptide sequence as defined by SEQ. ID.NO.: 14.

21. The transgenic plant of claim 18, wherein said bZIP domain transcription factor is ABF3 having a polypeptide sequence as defined by SEQ.ID.NO.: 14.

22. The transgenic plant of claim 18, wherein said transgenic plant is a monocot plant or a dicot plant.

23. A vector comprising an isolated polynucleotide having a polynucleotide sequence encoding a B3 domain transcription factor having a polynucleotide sequence with a B3 domain sequence which is at least 73% identical to the B3 domain sequence of SEQ. ID. NO.: 3 and an isolated polynucleotide having a polynucleotide sequence encoding a bZIP domain transcription factor having a polynucleotide sequence with a bZIP domain sequence which is at least 62% identical to the bZIP domain sequence of SEQ. ID. NO.: 13, said vector transforms a plant cell to synergistically transactivate ABA-inducible promoters.

24. The vector of claim 23, wherein said B3-domain transcription factor is RAV2 having a polynucleotide sequence as defined by SEQ.ID.NO.: 3.

25. The vector of claim 24, wherein bZIP domain transcription factor is ABF3 having a polynucleotide sequence as defined by SEQ. ID. NO. 13.

26. The vector of claim 23, wherein said bZIP domain transcription factor is ABF3 having a polynucleotide sequence as defined by is SEQ. ID. NO. 13.

27. A host cell comprising an isolated polynucleotide having a polynucleotide sequence encoding a B3 domain transcription factor having a polynucleotide sequence with a B3 domain sequence which is at least 73% identical to the B3 domain sequence of SEQ. ID. NO.: 3 and an isolated polynucleotide having a polynucleotide sequence encoding a bZIP domain transcription factor having a polynucleotide sequence with a bZIP domain sequence which is at least 62% identical to the bZIP domain sequence of SEQ. ID. NO.: 13, wherein said transcription factors synergistically transactivate ABA-inducible promoters.

28. The host cell of claim 27, wherein said B3-domain transcription factor is RAV2 having a polynucleotide sequence as defined by SEQ.ID.NO.: 3.

29. The host cell of claim 28, wherein said bZIP domain transcription factor is ABF3 having a polynucleotide sequence as defined by is SEQ. ID. NO. 13.

30. The host cell of claim 27, wherein said bZIP domain transcription factor is ABF3 having a polynucleotide sequence as defined by SEQ. ID. NO. 13.

31. A vector comprising an isolated polynucleotide having a polynucleotide sequence that encodes a B3 domain transcription factor having a polypeptide sequence with a B3 domain which is at least 58% identical to the B3 domain of SEQ.ID.NO.:4 and an isolated polynucleotide having a polynucleotide sequence that encodes a bZIP transcription factor having a polypeptide sequence with a bZIP domain which is at least 66% identical to the bZIP domain of SEQ. ID. NO.: 14, wherein said transcription factors synergistically transactivate ABA-inducible promoters.

32. The vector of claim 31, wherein said B3 domain transcription factor is RAV2 as defined by SEQ.ID.NO.: 4.

33. The vector of claim 32, wherein said bZIP domain transcription factor is ABF3 as defined by SEQ. ID. NO. 14.

34. The vector of claim 31, wherein said bZIP domain transcription factor is ABF3 as defined by SEQ. ID. NO. 14.

35. A host cell comprising an isolated polynucleotide having a polynucleotide sequence that encodes a B3-domain transcription factor having a polypeptide sequence with a B3 domain which is at least 58% identical to the B3 domain of SEQ. ID. NO.: 4 and an isolated polynucleotide having a polynucleotide sequence that encodes a bZIP-domain transcription factor having a polypeptide sequence with a bZIP domain which is at least 66% identical to the bZIP domain of SEQ. ID. NO.: 14, wherein said transcription factors synergistically transactivate ABA-inducible promoters.

36. The host cell of claim 35, wherein said B3-domain transcription factor is RAV2 as defined by SEQ.ID.NO.: 4.

37. The host cell of claim 36, wherein said bZIP domain transcription factor is ABF3 as defined by SEQ. ID. NO. 14.

38. The host cell of claim 35, wherein said bZIP domain transcription factor is ABF3 as defined by SEQ. ID. NO. 14.

39. The method of claim 1, wherein said transgenic plant is a member of the genus *Arabidopsis* or *Zea mays*.

40. The method of claim 7, wherein said transgenic plant is a member of the genus *Arabidopsis* or *Zea mays*.

41. The transgenic plant of claim 13, wherein said transgenic plant is a member of the genus *Arabidopsis* or *Zea mays*.

42. The transgenic plant of claim 18, wherein said transgenic plant is a member of the genus *Arabidopsis* or *Zea mays*.

43. The method of claim 1, wherein said B3-domain transcription factor has a polynucleotide sequence with a B3 domain sequence which is identical to the B3 domain sequence of SEQ. ID.NO: 3.

44. The method of claim 43, wherein said bZIP domain transcription factor has a polynucleotide sequence with a bZIP domain sequence which is identical to the bZIP domain sequence of SEQ. ID.NO.: 13.

45. The method of claim 1, wherein said bZIP domain transcription factor has a polynucleotide sequence with a bZIP domain sequence which is identical to the bZIP domain sequence of SEQ. ID.NO.: 13.

46. The method of claim 7, wherein said B3-domain transcription factor has a polypeptide sequence with a B3 domain sequence which is identical to the B3 domain sequence of SEQ. ID.NO.: 4.

47. The method of claim 46, wherein said bZIP domain transcription factor has a polypeptide sequence with a bZIP domain sequence which is identical to the bZIP domain sequence of SEQ. ID.NO.: 14.

48. The method of claim 7, wherein said bZIP domain transcription factor has a polypeptide sequence with a bZIP domain sequence which is identical to the bZIP domain sequence of SEQ. ID.NO.: 14.

49. The transgenic plant of claim 13, wherein said B3-domain transcription factor has a polynucleotide sequence with a B3 domain sequence which is identical to the B3 domain sequence of SEQ. ID.NO: 3.

50. The transgenic plant of claim 49, wherein said bZIP domain transcription factor has a polynucleotide sequence with a bZIP domain sequence which is identical to the bZIP domain sequence of SEQ. ID.NO.: 13.

51. The transgenic plant of claim 13, wherein said bZIP domain transcription factor has a polynucleotide sequence with a bZIP domain sequence which is identical to the bZIP domain sequence of SEQ. ID.NO.: 13.

52. The transgenic plant of claim 18, wherein said B3-domain transcription factor has a polypeptide sequence with a B3 domain sequence which is identical to the B3 domain sequence of SEQ. ID.NO.: 4.

53. The transgenic plant of claim 52, wherein said bZIP domain transcription factor has a polypeptide sequence with a bZIP domain sequence which is identical to the bZIP domain sequence of SEQ. ID.NO.: 14.

54. The transgenic plant of claim 18, wherein said bZIP domain transcription factor has a polypeptide sequence with a bZIP domain sequence which is identical to the bZIP domain sequence of SEQ. ID.NO.: 14.

55. The vector of claim 23, wherein said B3-domain transcription factor has a polynucleotide sequence with a B3 domain sequence which is identical to the B3 domain sequence of SEQ. ID.NO: 3.

56. The vector of claim 55, wherein said bZIP domain transcription factor has a polynucleotide sequence with a bZIP domain sequence which is identical to the bZIP domain sequence of SEQ. ID.NO.: 13.

57. The vector of claim 23, wherein said bZIP domain transcription factor has a polynucleotide sequence with a bZIP domain sequence which is identical to the bZIP domain sequence of SEQ. ID.NO.: 13.

58. The host cell of claim 27, wherein said B3-domain transcription factor has a polynucleotide sequence with a B3 domain sequence which is identical to the B3 domain sequence of SEQ. ID.NO: 3.

59. The host cell of claim 58, wherein said bZIP domain transcription factor has a polynucleotide sequence with a bZIP domain sequence which is identical to the bZIP domain sequence of SEQ. ID.NO.: 13.

60. The host cell of claim 27, wherein said bZIP domain transcription factor has a polynucleotide sequence with a bZIP domain sequence which is identical to the bZIP domain sequence of SEQ. ID.NO.: 13.

61. The vector of claim 31, wherein said B3-domain transcription factor has a polypeptide sequence with a B3 domain sequence which is identical to the B3 domain sequence of SEQ. ID.NO.: 4.

62. The vector of claim 61, wherein said bZIP domain transcription factor has a polypeptide sequence with a bZIP domain sequence which is identical to the bZIP domain sequence of SEQ. ID.NO.: 14.

63. The vector of claim 31, wherein said bZIP domain transcription factor has a polypeptide sequence with a bZIP domain sequence which is identical to the bZIP domain sequence of SEQ. ID.NO.: 14.

64. The host cell of claim 35, wherein said B3-domain transcription factor has a polypeptide sequence with a B3 domain sequence which is identical to the B3 domain sequence of SEQ. ID.NO.: 4.

65. The host cell of claim 64, wherein said bZIP domain transcription factor has a polypeptide sequence with a bZIP domain sequence which is identical to the bZIP domain sequence of SEQ. ID.NO.: 14.

66. The host cell of claim 35, wherein said bZIP domain transcription factor has a polypeptide sequence with a bZIP domain sequence which is identical to the bZIP domain sequence of SEQ. ID.NO.: 14.

* * * * *